(12) United States Patent
Džakula

(10) Patent No.: US 10,844,424 B2
(45) Date of Patent: Nov. 24, 2020

(54) REDUCTION OF BIAS IN GENOMIC COVERAGE MEASUREMENTS

(71) Applicant: BioNano Genomics, Inc., San Diego, CA (US)

(72) Inventor: Željko Džakula, San Diego, CA (US)

(73) Assignee: Bionano Genomics, Inc., San Diego, CA (US)

(*) Notice: Subject to any disclaimer, the term of this patent is extended or adjusted under 35 U.S.C. 154(b) by 342 days.

(21) Appl. No.: 15/117,689

(22) PCT Filed: Feb. 24, 2015

(86) PCT No.: PCT/US2015/017356
§ 371 (c)(1),
(2) Date: Aug. 9, 2016

(87) PCT Pub. No.: WO2015/130696
PCT Pub. Date: Sep. 3, 2015

(65) Prior Publication Data
US 2016/0355873 A1    Dec. 8, 2016

Related U.S. Application Data

(60) Provisional application No. 62/101,291, filed on Jan. 8, 2015, provisional application No. 61/944,465, filed on Feb. 25, 2014.

(51) Int. Cl.
| G01N 33/48 | (2006.01) |
| G01N 33/50 | (2006.01) |
| C12Q 1/6809 | (2018.01) |

(52) U.S. Cl.
CPC .................. *C12Q 1/6809* (2013.01)

(58) Field of Classification Search
None
See application file for complete search history.

(56) References Cited

U.S. PATENT DOCUMENTS

| 8,628,919 B2 | 1/2014 | Xiao et al. |
| 8,722,327 B2 | 5/2014 | Cao et al. |
| 9,310,376 B2 | 4/2016 | Cao et al. |
(Continued)

FOREIGN PATENT DOCUMENTS

| WO | WO2008079169 | 7/2008 |
| WO | WO 2008/121828 A2 * | 10/2008 |
(Continued)

OTHER PUBLICATIONS

U.S. Appl. No. 61/713,862, filed Oct. 15, 2012, Saghbini et al.
(Continued)

*Primary Examiner* — Russell S Negin
(74) *Attorney, Agent, or Firm* — Sheppard, Mullin, Richter & Hampton LLP

(57) ABSTRACT

Methods are provided for detecting and quantitating molecules using fluidics. In some embodiments, the methods comprise minimizing or eliminating biases caused by label density, or minimizing or eliminated biases caused by factors other than label density. In some embodiments, the methods comprise automated identification of genetic structural variation. In some embodiments, the methods comprise analyzing blood to detect the presence of circulating DNA or cells from a fetus or tumor.

20 Claims, 57 Drawing Sheets

(56) References Cited

U.S. PATENT DOCUMENTS

| | | | |
|---|---|---|---|
| 9,809,855 B2* | 11/2017 | Cao | G01N 33/5091 |
| 10,000,804 B2 | 6/2018 | Cao et al. | |
| 2003/0104428 A1* | 6/2003 | Branton | C12Q 1/68 |
| | | | 435/6.11 |
| 2004/0197843 A1 | 10/2004 | Chou et al. | |
| 2006/0063184 A1* | 3/2006 | Felix | C12Q 1/6876 |
| | | | 435/6.14 |
| 2008/0242556 A1 | 10/2008 | Cao et al. | |
| 2009/0305273 A1 | 12/2009 | Cao et al. | |
| 2010/0285082 A1 | 11/2010 | Fernandez | |
| 2011/0117577 A1 | 5/2011 | Reboud et al. | |
| 2011/0171634 A1 | 7/2011 | Xiao et al. | |
| 2011/0229888 A1 | 9/2011 | Hengen et al. | |
| 2011/0296903 A1 | 12/2011 | Cao et al. | |
| 2011/0306504 A1 | 12/2011 | Xiao et al. | |
| 2012/0095697 A1 | 4/2012 | Halpern et al. | |
| 2012/0097835 A1 | 4/2012 | Sharonov | |
| 2012/0100600 A1 | 4/2012 | Slepnev | |
| 2012/0108920 A1 | 5/2012 | Bly et al. | |
| 2012/0237936 A1 | 9/2012 | Xiao et al. | |
| 2012/0244635 A1 | 9/2012 | Austin et al. | |
| 2013/0034546 A1 | 2/2013 | Rava et al. | |
| 2013/0036860 A1 | 3/2013 | Xiao et al. | |
| 2013/0055817 A1 | 3/2013 | Maeda et al. | |
| 2013/0072386 A1 | 3/2013 | Xiao et al. | |
| 2013/0085681 A1 | 4/2013 | Deciu et al. | |
| 2013/0103320 A1 | 4/2013 | Dzakula et al. | |
| 2013/0150253 A1 | 6/2013 | Deciu et al. | |
| 2013/0261983 A1 | 10/2013 | Dzakula et al. | |
| 2013/0309666 A1 | 11/2013 | Deciu et al. | |
| 2013/0325360 A1 | 12/2013 | Deciu et al. | |
| 2013/0338933 A1 | 12/2013 | Deciu et al. | |
| 2014/0014497 A1 | 1/2014 | Druz et al. | |
| 2014/0099642 A1 | 4/2014 | Jiang et al. | |
| 2016/0046992 A1 | 2/2016 | Cao et al. | |

FOREIGN PATENT DOCUMENTS

| | | |
|---|---|---|
| WO | WO2008121828 | 10/2008 |
| WO | WO2009149362 | 12/2009 |
| WO | WO2010002883 | 1/2010 |
| WO | WO2010059731 | 5/2010 |
| WO | WO2010135323 | 11/2010 |
| WO | WO2011038327 | 3/2011 |
| WO | WO2011050147 | 4/2011 |
| WO | WO2012054735 | 4/2012 |
| WO | WO2012108920 | 8/2012 |
| WO | WO2013000100 | 1/2013 |
| WO | WO2013036860 | 3/2013 |
| WO | WO2013052907 | 4/2013 |
| WO | WO2013052913 | 4/2013 |
| WO | WO2013055817 | 4/2013 |
| WO | WO2013109981 | 7/2013 |
| WO | WO 2013/166517 A1 * | 11/2013 |
| WO | WO2013166517 | 11/2013 |
| WO | WO2013177086 | 11/2013 |
| WO | WO2013192562 | 12/2013 |
| WO | WO2014014497 | 1/2014 |
| WO | WO2014123822 | 8/2014 |
| WO | WO2014130589 | 8/2014 |

OTHER PUBLICATIONS

U.S. Appl. No. 61/734,327, filed Dec. 6, 2012, Saghbini et al.
Chao & Tammi, "CNV-seq, a new method to detect copy number variation using high-throughput sequencing," BMC Bioinformatics 2009, 10(80), doi:10.1186/1471-2105-10-80, in 9 pages.
Examination Report dated Apr. 26, 2018 in European Patent Application No. 14753475.4.
Examination Report dated Mar. 7, 2019 in European Patent Application No. 14753475.4.
Extended European Search Report dated Jul. 14, 2016 in European Patent Application No. 14753475.4.
International Preliminary Report on Patentability dated Aug. 30, 2016 in PCT Application No. PCT/US2015/017356.
International Preliminary Report on Patentability dated Apr. 10, 2015 in PCT Application No. PCT/US2014/017226.
International Search Report and Written Opinion dated Jun. 10, 2015 in PCT Application No. PCT/US2015/017356.
International Search Report and Written Opinion dated May 30, 2014 in PCT Application No. PCT/US2014/017226.
Jensen et al., "Detection of Microdeletion 22q11.2 in a Fetus by Next-Generation Sequencing of Maternal Plasma," Clinical Chemistry 2012, 58(7), 1148-1151.
Jensen et al., "High-Throughput Massively Parallel Sequencing for Fetal Aneuploidy Detection from Maternal Plasma," PLoS One 2013, 8(3), e57381, in 8 pages.
Kidd et al., "Mapping and sequencing of structural variation from eight human genomes," Nature 2008, 453, 56-64.
Lam et al., "Genome mapping on nanochannel arrays for structural variation analysis and sequence assembly," Nature Biotechnology 2012, 30(8), 771-776.
Mazloom et al., "Noninvasive prenatal detection of sex chromosomal aneuploidies by sequencing circulating cell-free DNA from maternal plasma," Prenatal Diagnosis 2013, 33, 591-597.
Nord et al., "Accurate and exact CNV identification from targeted high-throughput sequence data," BMCGenomics2011, 12(184), 1-10.
Notification of Reasons for Refusal dated Oct. 16, 2018 in Japanese Patent Application No. 2015-558929.
Notification of Reasons for Refusal dated Jan. 30, 2018 in Japanese Patent Application No. 2015-558929.
Notice of Allowance dated Apr. 30, 2020 in Chinese Patent Application No. 201580016272.3.
Notice of Allowance dated Apr. 17, 2020 in Chinese Patent Application No. 201480009730.6.
Notice of Allowance dated May 18, 2020 in European Patent Application No. 14753475.4.
Notice of Allowance dated Apr. 26, 2019 in Japanese Patent Application No. 2015-558929.
Notice of Allowance dated Jul. 6, 2017 in U.S. Appl. No. 14/768,422.
Notice of Allowance dated Jan. 23, 2020 in U.S. Appl. No. 15/795,847.
Office Action dated Oct. 26, 2016 in U.S. Appl. No. 14/768,422.
Office Action dated Dec. 11, 2018 in U.S. Appl. No. 15/795,847.
Office Action dated Jul. 16, 2019 in U.S. Appl. No. 15/795,847.
Office Action dated Oct. 24, 2016 in Chinese Patent Application No. 201480009730.6.
Office Action dated Jun. 14, 2018 in Chinese Patent Application No. 201480009730.6.
Office Action dated Sep. 20, 2017 in Chinese Patent Application No. 201480009730.6.
Office Action dated Mar. 29, 2019 in Chinese Patent Application No. 201580016272.3.
Office Action dated Jan. 2, 2020 in Chinese Patent Application No. 201580016272.3.
Office Action dated Jan. 27, 2020 in Canadian Patent Application No. 2,901,460.
Oldridge et al., "Optimizing copy number variation analysis using genome-wide short sequence oligonucleotide arrays," Nucleic Acids Research 2010, 38(10), 3275-3286.
Schouten et al., "Platform comparisons for identification of breast cancers with a BRCA-like copy number profile," Breast Cancer Research and Treatment 2013, 139, 317-327.
Stavis et al., "Single-molecule mobility and spectral measurements in submicrometer fluidic channels," Journal of Applied Physics 2005, 98(044903), in 5 pages.
Yahya-Graison et al., "Classification of Human Chromosome 21 Gene-Expression Variations in Down Syndrome: Impact on Disease Phenotypes," The American Journal of Human Genetics 2007, 81, 475-491.

* cited by examiner

Coverage Distribution for Chromosome 1

Coverage Distribution for Chromosome X

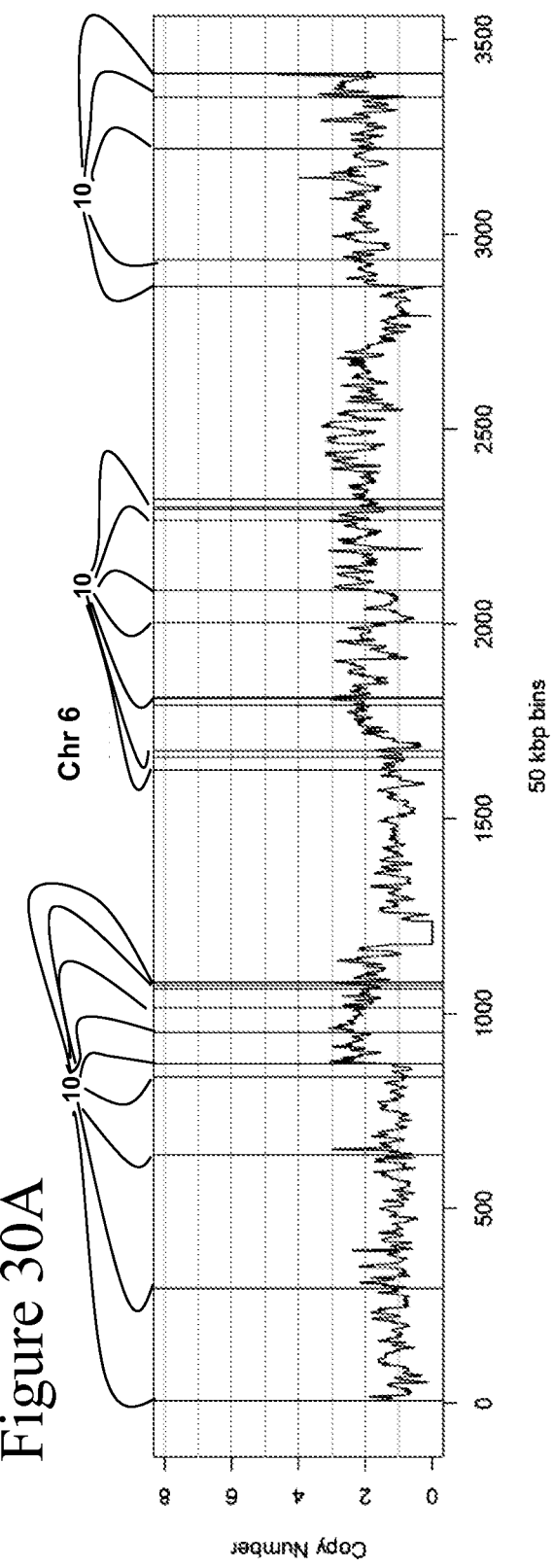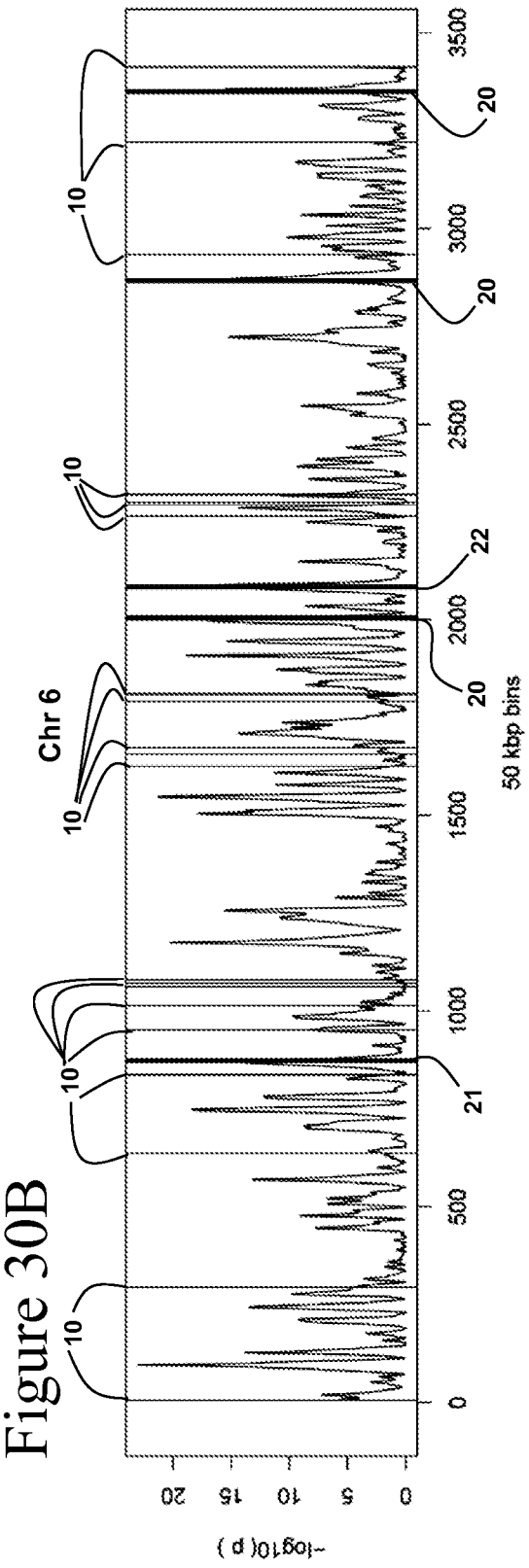

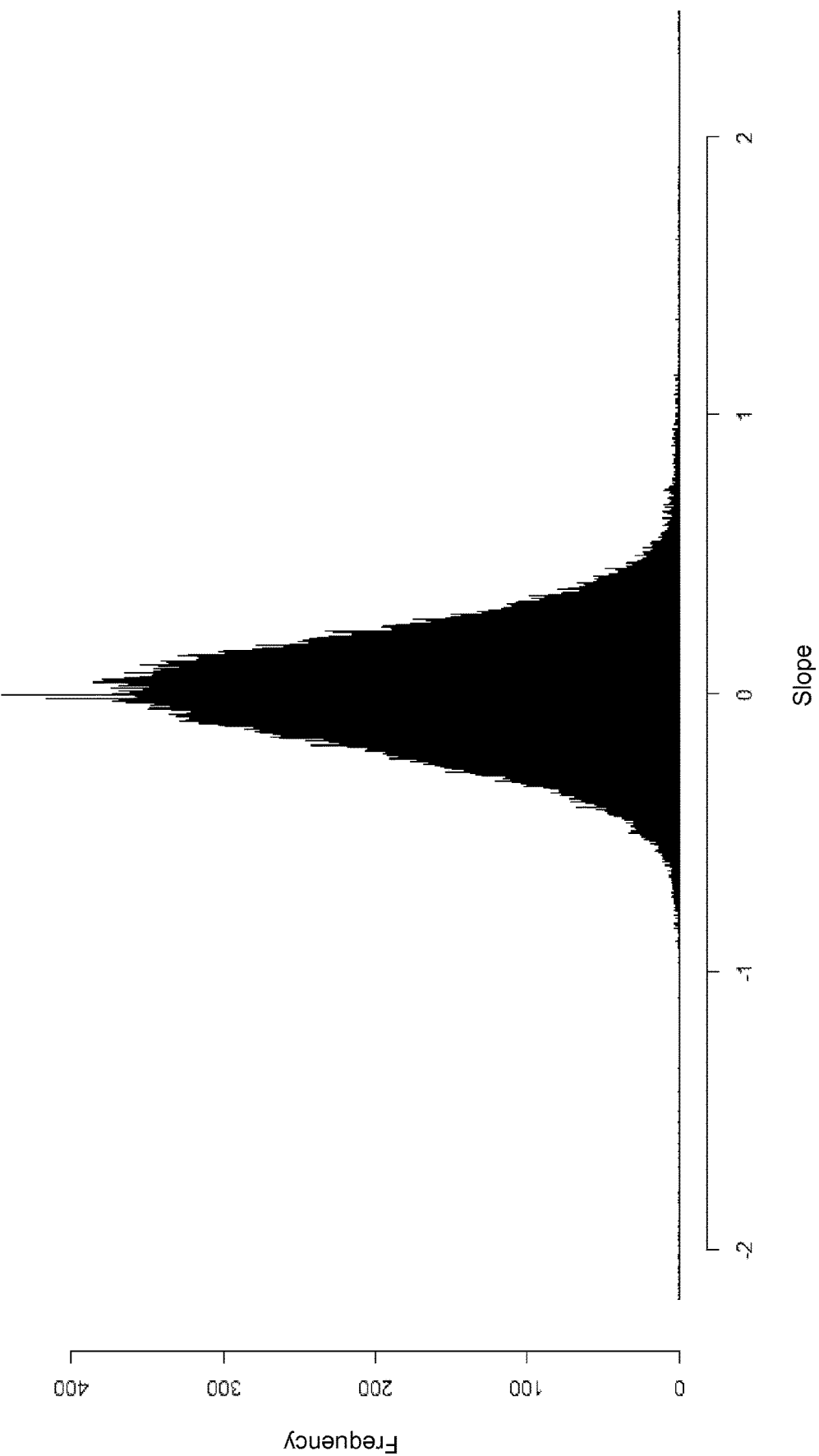

REDUCTION OF BIAS IN GENOMIC COVERAGE MEASUREMENTS

CROSS-REFERENCE TO RELATED APPLICATIONS

This application is a U.S. national phase under 35 U.S.C. § 371 of International Application No. PCT/US2015/017356, entitled REDUCTION OF BIAS IN GENOMIC COVERAGE MEASUREMENTS, filed Feb. 24, 2015, and published on Sep. 3, 2015 as WO/2015/130696, which claims the benefit of U.S. Provisional Application No. 61/944,465 filed Feb. 25, 2014 and U.S. Provisional Application No. 62/101,291 filed Jan. 8, 2015 each of these related applications is hereby incorporated by reference in its entirety. This Application is related to U.S. Provisional Application No. 61/767,219, filed Feb. 20, 2013, and PCT Application No. PCT/US2014/017226 filed Feb. 19, 2014, each of which is hereby incorporated by reference in its entirety.

SUMMARY

In some embodiments, a method of characterizing sample in provided. The method can comprise labeling a plurality of sample molecules with a first label, in which the sample molecules comprise a genome or genomic fragment. The method can comprise translocating the plurality of labeled sample molecules though a fluidic channel. The method can comprise detecting counts of signals from the labeled sample molecules so as to ascertain a pattern or plurality of patterns characteristic of the genome or genomic fragment. The method can comprise correlating signals from the labeled sample molecules to a reference to ascertain coverage of one or more regions of the genome or genomic fragment by the sample molecules. The method can comprise scaling the coverage depths of signals to a subset of coverage depths of signals corresponding to regions of the genome or genomic fragment that does not comprise a sex chromosome or a fragment thereof, thereby providing scaled coverage depths. The method can comprise normalizing the scaled coverage depths by one, two, or three of: (i) characteristic molecular length of the plurality of labeled sample molecules, or (ii) characteristic number of labels per interval for a plurality of intervals of the reference, in which the reference comprises a plurality of intervals, or (iii) characteristic number of labels per molecule or characteristic number of labels within a segment of predetermined length per molecule, thus generating a copy number profile of the sample molecules in which bias due to label density and bias due to factors other than label density in the copy number profile are minimized or eliminated. In some embodiments, the scaled coverage depths comprise normalizing the scaled coverage depths by characteristic molecular length of the plurality of labeled sample molecules. In some embodiments, the method further comprises generating a histogram of molecular lengths of the plurality of sample molecules. In some embodiments, normalizing the scaled coverage depths comprises obtaining normalized label coverage depths as provided by the formula: $n=Q/[E+GC(1/\lambda-1/\lambda_0)]$, wherein n represents normalized label coverage depths. Q represents scaled label coverage depths, G and E respectively represent gradient and zero-order coefficient of a linear regression of scaled label coverage depths versus abscissa for a plurality of samples in a training set, $\lambda$ represents characteristic sample-specific molecule length, and $\lambda_0$ represents median characteristic molecule length for the plurality of samples of the training set. In some embodiments, normalizing the scaled coverage depths comprises: generating a raw coverage depth profile per label, transforming the raw coverage depth profile to the corresponding scaled label coverage depth profile, generating a sample-specific characteristic molecular length, parameterization comprising gradient and zero-order coefficient values, label filtering based on relative errors, base error, or magnitude of the zero-order coefficient; and normalizing scaled label coverage depths with respect to the sample-specific characteristic molecular length. In some embodiments, normalizing the scaled coverage depths comprises performing SIngle MOlecule NormalIzation to Detect Aberrations (SIMONIDA). In some embodiments, normalizing the scaled coverage depths also comprises Sex Chromosome Normalization. In some embodiments, Sex Chromosome Normalization comprises: scaling the scaled label coverage depths for a training sample based on the number of sex chromosomes in the training sample; and normalizing scaled label coverage depths with respect to characteristic molecular length of the plurality of labeled sample molecules, and further comprises dividing normalized label coverage depths by a median of normalized coverage depths for a plurality of sex chromosomes of a training set. In some embodiments, normalized label coverage depths for an X chromosome are divided by the median normalized coverage depths for a plurality of euploid female and Klinefelter samples of a training set. In some embodiments, normalized label coverage depths for a Y chromosome are divided by the median normalized coverage depths for a plurality of male samples of a training set and are further divided by two. In some embodiments. Sex Chromosome Normalization comprises robust linear regression of scaled label coverage depths. In some embodiments, Sex Chromosome Normalization comprises generating a copy number profile only from labels that satisfy at least one label exclusion criterion. In some embodiments, the copy number profile is generated only from labels of labeled sample molecules that comprise a ratio of a base error for a given label in a given sample to an zero-order coefficient for the label, wherein the ratio is in a 95% quantile for base error for a plurality of samples from the same chromosome as the label. In some embodiments a Y chromosome copy number profile is generated only from labels of labeled sample molecules for which the median normalized coverage depth of the label for all male samples of a training set is significantly greater than a median normalized coverage depth for all female samples of a training set, relative to the combined median absolute deviations for all male and all female samples of a training set.

In some embodiments, the scaled coverage depths comprises normalizing the scaled coverage depths by characteristic number of labels per interval for a plurality of intervals of the reference. In some embodiments, normalizing the scaled coverage depths comprises obtaining normalized label coverage depths as provided by the formula $n=(c-GL)/E$, wherein n represents normalized label coverage depths, c represents scaled coverage depth, L represents gradient of a linear regression of scaled coverage depth vs. the number of labels per interval for a plurality of samples in a training set, and G and E respectively represent gradient and zero-order coefficient of a linear regression of scaled coverage depth versus abscissa for a plurality of samples in a training set. In some embodiments, normalizing coverage depths of the signals comprises performing GROM. In some embodiments, the plurality of intervals of the reference comprise intervals of a predetermined size. In some embodiments, the plurality of intervals of the reference are of equal size. In some embodiments, the plurality of intervals of the reference are not of equal size. In some embodiments, each of the plurality of intervals comprises about 10,000 to about 90,000 base pairs. In some embodiments, each of the plurality of intervals comprises about 40,000 to about 60,000 base pairs. In some embodiments, generating a copy number profile comprises generating a raw coverage depth profile per interval from the detected signals, transforming the raw coverage depth profile to a corresponding scaled coverage depth profile per interval, generating a sample-specific label density bias coefficient (L) representing gradient of a linear regression of scaled coverage depth vs. the number of labels per interval for a plurality of samples in a training set, and parameterizing intervals, in which the interval parameters comprise gradient and zero-order coefficient values, filtering intervals based on at least on measurement of error, normalizing scaled coverage depth with respect to L, and generating a plurality of copy number profiles from the normalized coverage depth profiles. In some embodiments, normalizing the scaled coverage depths comprises normalizing the scaled coverage depths by characteristic number of labels per molecule or characteristic number of labels within a segment of predetermined length per molecule. In some embodiments, normalizing the scaled coverage depths comprises normalizing the scaled coverage depths by characteristic number of labels per molecule. In some embodiments, normalizing the scaled coverage depths comprises normalizing the scaled coverage depths by characteristic number of labels within a segment of predetermined length per molecule. In some embodiments, the segment of predetermined length per molecule comprises 100 kb of nucleic acid. In some embodiments, the segment of predetermined length per molecule comprises at least 20 kb of nucleic acid, for example 20 kb, 30 kb, 40 kb, 50 kb, 100 kb, 150 kb, 200 kb, 250 kb, 300 kb, 350 kb, 400 kb, or 500 kb, including ranges between any two of the listed values.

In some embodiments, the subset of coverage depths of signals corresponding to regions of the genome or genomic fragment that does not comprise sex chromosomes comprises the coverage depths of signals corresponding to autosomal regions of the genome. In some embodiments, the pattern or plurality of patterns comprise patterns of genomic sequences. In some embodiments, the pattern or plurality of patterns comprise an epigenetic pattern. In some embodiments, the method is repeated for a plurality of samples in a training set. In some embodiments, the method further comprises measurement of error comprising relative errors. In some embodiments, the method further comprises storing a raw coverage depth profile in a computer readable medium, wherein the raw coverage depth profile comprises detected coverage depths of the signals from the labeled sample molecules. In some embodiments, the reference comprises a reference genome. In some embodiments, the reference comprises hg19 or GRCh38. In some embodiments, the reference comprises digital digested in silico barcodes derived from a reference genome. In some embodiments, the reference comprises a labeled reference molecule. In some embodiments, the reference comprises an optically stored value or set of values or electronically stored value or set of values. In some embodiments, the reference comprises an optically stored value or set of values. In some embodiments, the reference comprises an electronically stored value or set of values. In some embodiments, the first label comprises a sequence-specific label. In some embodiments, the first label comprises an epigenetic label. In some embodiments, the first label comprises an optical label. In some embodiments, the first label comprises a non-optical label. In some embodiments, the first label comprises at least one of a fluorescent label, a radioactive label, a magnetic label, or a transcriptional terminator. In some embodiments, labeling comprises contacting the sample molecules with at least one of a non-cutting restriction enzyme, a zinc finger protein, an antibody, a transcription factor, a transcription activator like domain, a DNA binding protein, a polyamide, a triple helix forming oligonucleotide, and a peptide nucleic acid, and a methyltransferase. In some embodiments, an elevation or depletion of the copy number profile represents an aneuploidy. In some embodiments, the method further comprises automatically determining a presence or absence of aneuploidy of a chromosome of the genome or genomic fragment. In some embodiments, the method further comprises automatically determining a presence or absence of possible structural variation in of the genome or genomic fragment. In some embodiments, automatically determining a presence or absence of possible regional structural variation comprises identifying possible breakpoints in the copy number profile, wherein an interval in the copy number profile with a significantly different copy number than a neighboring interval comprises a possible breakpoint. In some embodiments, automatically determining a presence or absence of possible regional structural variation comprises determining GROM copy number breakpoints. In some embodiments, automatically determining a presence or absence of possible regional structural variation comprises determining SIMONIDA copy number breakpoints. In some embodiments, the method further comprises identifying overlap between GROM copy number breakpoints and SIMONIDA copy number breakpoints. In some embodiments, the method further comprises determining a plurality of possible structural variants using a second method; and identifying overlap between the GROM copy number breakpoints or SIMONIDA copy number breakpoints and the plurality of possible structural variants determined by the second method. In some embodiments, the method further comprises, for each of the copy number breakpoints: identifying a first region of a reference sequence on a first side of the breakpoint, and masking a second region of the reference sequence on a second side of the breakpoint, wherein the second side is opposite the first side; and scoring only single molecule alignments that align with the reference in the first region. In some embodiments, the method further comprises clustering single molecule alignments to the second region; and aligning each cluster to a reference sequence. In some embodiments, the copy number profile is generated in real-time. In some embodiments, the copy number profile is generated in less than five minutes after the signals are detected. In some embodiments, the copy number profile is generated in less than 60 seconds after the signals are detected. In some embodiments, the copy number profile is generated by a processor in data communication with a detector to detect signals from the labeled sample molecules and labeled reference molecules. In some embodiments, the genomic fragment or fragments comprises an autosome or at least one fragment thereof, selected from the group consisting of: human chromosome 21, human chromosome 13, human chromosome 14, human chromosome 15, human chromosome 16, human chromosome 18, and human chromosome 22, and fragments thereof. In some embodiments, the genomic fragment or fragments comprises an autosome or at least one fragment thereof, selected from the group consisting of: human chromosome 1, human chromosome 2, human chromosome 3, human chromosome 4, human chromosome 5, human chromosome 6, human chromosome 7, human chromosome 8, human chromosome 9, human chromosome 10, human chromosome 11, human chromosome 12, human chromosome 13, human chromosome 14, human chromosome 15, human chromosome 16, human chromosome 17, human chromosome 18, human chromosome 19, human chromosome 20, human chromosome 21, human chromosome 22, human chromosome X, human chromosome Y, and fragments thereof. In some embodiments, the sample molecules are from a sample comprising a possible genomic abnormality. In some embodiments, the genetic abnormality comprises at least one of a duplication, deletion, or translocation. In some embodiments, labeling comprises labeling the sample molecules with the label, and further comprises labeling the sample molecules with a second label that is different from the first label. In some embodiments, labeling comprises nicking one strand of a double-stranded DNA at a first sequence motif with a nicking endonuclease, and labeling the DNA with the first label. In some embodiments, the method further comprises repairing at least some of the nicks on the DNA. In some embodiments, the nicks are not repaired. In some embodiments, labeling comprises tagging at least one sequence motif of the sample molecules with a DNA binding entity selected from the group consisting of: a non-cutting restriction enzyme, a zinc finger protein, an antibody, a transcription factor, a transcription activator like domain, a DNA binding protein, a polyamide, a triple helix forming oligonucleotide, and a peptide nucleic acid, and a methyltransferase. In some embodiments, labeling with the first label comprises tagging at least one sequence motif of the sample molecules with a methyltransferase. In some embodiments, the method further comprises labeling the sample molecule with a non-sequence-specific label. In some embodiments, the non-sequence-specific label comprises a backbone dye (e.g. YOYO, POPO, and the like).

In some embodiments, a method of characterizing a sample is provided. The method can comprise labeling a plurality of sequence-specific locations on a polynucleotide sequence of a sample molecule. The method can comprise linearizing at least a portion of the sample molecule in a fluidic channel. The method can comprise quantifying a signal from the labels on the sample molecule; correlating the signal from the labels to a reference; generating a copy number profile of the sample molecule. The method can comprise determining a presence or absence of a genetic abnormality in the sample DNA when the quantity of the signal from the sample molecule differs from a quantity of the signal arising from a reference molecule. In some embodiments, generating a copy number profile comprises minimizing or eliminating bias by normalizing the scaled coverage depths by characteristic molecular length of the plurality of labeled sample molecules. In some embodiments, the method further comprises generating a histogram of molecular lengths of the plurality of sample molecules. In some embodiments, generating a copy number profile comprises generating a raw coverage depth profile per label, transforming the raw coverage depth profile to a corresponding scaled label coverage depth profile, generating a sample-specific characteristic molecular length, parameterization comprising gradient and zero-order coefficient values, label filtering based on relative errors, base error, or magnitude of the zero-order coefficient; and normalizing scaled label coverage depths with respect to the sample-specific characteristic molecular length. In some embodiments, generating a copy number profile comprises performing SIngle MOlecule Normalization to Detect Aberrations (SIMONIDA). In some embodiments, generating a copy number profile of the sample molecule comprises minimizing or eliminating bias by normalizing the scaled coverage depths by characteristic number of labels per molecule or characteristic number of labels within a segment of predetermined length per molecule. In some embodiments, normalizing the scaled coverage depths comprises normalizing the scaled coverage depths by characteristic number of labels per molecule. In some embodiments, normalizing the scaled coverage depths comprises normalizing the scaled coverage depths by characteristic number of labels within a segment of predetermined length per molecule. In some embodiments, the segment of predetermined length per molecule comprises 100 kb of nucleic acid. In some embodiments, generating a copy number profile of the sample molecule comprises: generating a raw coverage depth profile per label; transforming the raw coverage depth profile to a corresponding scaled label coverage depth profile; scaling the scaled label coverage depths for a training sample based on the number of sex chromosomes in the training sample; normalizing scaled label coverage depths with respect to characteristic molecular length of the plurality of labeled sample molecules; and dividing the normalized label coverage depths by a median of normalized coverage depths for a plurality of sex chromosomes of a training set. In some embodiments, normalized label coverage depths for an X chromosome are divided by the median normalized coverage depths for a plurality of female samples of a training set. In some embodiments, normalized label coverage depths for an X chromosome are divided by the median normalized coverage depths for a plurality of male samples and/or Turner syndrome (XO) samples of a training set, in which the male and/or Turner syndrome ChrX coverage depths are multiplied by 2, and assigned a weight of 1/sqrt(2). In some embodiments, normalized label coverage depths for a Y chromosome are divided by the median normalized coverage depths for a plurality of male samples of a training set and are further divided by two. In some embodiments, generating a copy number profile for sex chromosomes comprise robust linear regression of scaled label coverage depths. In some embodiments, normalized label coverage depths for sex chromosomes comprise generating a copy number profile only from labels that satisfy at least one label exclusion criterion, for example one, two, three, four, or five label exclusion criteria as described herein. In some embodiments, the copy number profile is generated only from labels of labeled sample molecules that comprise a ratio of a base error for a given label in a given sample to an zero-order coefficient for the label, wherein the ratio is in a 95% quantile for base error for a plurality of samples from the same chromosome as the label. In some embodiments, a Y chromosome copy number profile is generated only from labels of labeled sample molecules for which the median normalized coverage depth of the label for all male samples of a training set is significantly greater than a median normalized coverage depth for all female samples of a training set, relative to the combined median absolute deviations for all male and all female samples of a training set.

In some embodiments, generating a copy number profile comprises generating a raw coverage depth profile per interval from the detected signals, transforming the raw coverage depth profile to a corresponding scaled coverage depth profile per interval, generating a sample-specific label density bias coefficient (LDBC), parameterizing intervals, wherein the interval parameters comprise gradient and zero-order coefficient values, filtering intervals based on at least on measurement of error, normalizing scaled coverage depth with respect to LDBC, and generating a plurality of copy number profiles from the normalized coverage depth profiles. In some embodiments, generating a copy number profile comprises performing GROM. In some embodiments, the intervals are of equal size. In some embodiments, the intervals are not of equal size. In some embodiments, each interval comprises about 10,000 to about 90,000 base pairs. In some embodiments, the scaled coverage depth profile comprises at least about 20,000 intervals. In some embodiments, determining a presence or absence of a genetic abnormality comprises identifying a plurality of intervals for a chromosome or portion thereof, wherein the each interval of the plurality has a significantly different copy number than the reference molecule. In some embodiments, the method further comprises automatically determining a presence or absence of possible regional structural variation in the first genomic fragment or fragments of interest. In some embodiments, automatically determining a presence or absence of possible structural variation comprises identifying possible breakpoints in the copy number profile, wherein an interval in the copy number profile with a significantly different copy number than a neighboring interval comprises a possible breakpoint. In some embodiments, automatically determining a presence or absence of possible structural variation comprises determining GROM copy number breakpoints. In some embodiments, the reference comprises an electronically or optically stored value or set of values. In some embodiments, the reference comprises an electronically stored value or set of values. In some embodiments, the reference comprises an or optically stored value or set of values. In some embodiments, the sample molecule comprises a DNA. In some embodiments, the sample molecule comprises chromatin. In some embodiments, the sample molecules comprise short nucleic acids of about 10-2000 base pairs in length. In some embodiments, the sample molecules comprise short nucleic acids of about 10-1000 base pairs in length. In some embodiments, the sample molecules comprise short nucleic acids of about 100-2000 base pairs in length. In some embodiments, the sample molecules comprise short nucleic acids of about 100-1000 base pairs in length. In some embodiments, the genetic abnormality comprises at least one of a translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy, tetraploidy, or sex chromosome aneuploidy. In some embodiments, the genetic abnormality comprises a hypopolyploidy or a hyperpolyploidy. In some embodiments, labeling comprises labeling the polynucleotide with at least one of a fluorescent label, a radioactive label, a magnetic label, or a non-optical label. In some embodiments, labeling comprises nicking one strand of a double-stranded DNA at a first sequence motif with a nicking endonuclease; and labeling the DNA. In some embodiments, labeling comprises nicking one strand of a double-stranded DNA at least two different motifs with at least two different nicking endonucleases, for example, two, three, four, five, six, seven, eight, nine, or ten nicking endonucleases, including ranges between any two of the listed values. Optionally, each of the different endonuclease target motifs is labeled with a different label (for example, different fluorophores, quantum dots, non-optical labels, etc.). Optionally, two or more of the different endonuclease target motifs are labeled with the same label. In some embodiments, the method further comprises repairing at least some of the nicks on the first DNA. In some embodiments, the nicks are not repaired. In some embodiments, the label comprises a transcriptional terminator. In some embodiments, labeling comprises tagging at least one sequence motif of the sample molecules with a DNA binding entity selected from the group consisting of: a non-cutting restriction enzyme, a zinc finger protein, an antibody, a transcription factor, a transcription activator like domain, a DNA binding protein, a polyamide, a triple helix forming oligonucleotide, and a peptide nucleic acid, and a methyltransferase. In some embodiments, labeling with the first label comprises tagging at least one sequence motif of the sample molecules with a methyltransferase.

In some embodiments, for any of the methods described above, the fluidic nanochannel comprises a channel having a length of at least 10 nm and a cross-section diameter of less than 5000 nm.

In some embodiments, for any of the methods described above, the sample is selected from the group consisting of a bacteria, a virion, a DNA molecule, an RNA molecule, a nucleic acid polymer, a protein, a peptide, and a polysaccharide. In some embodiments, for any of the methods described above, the sample is derived from maternal blood, and wherein the reference molecule is derived from a maternal sample other than blood. In some embodiments, for any of the methods described above, the sample comprises a nucleotide, and wherein the at least two labels are located at either end of a zone of interest in the nucleotide. In some embodiments, for any of the methods described above, reference is derived from a known diploid or haploid chromosome.

In some embodiments, for any of the methods described above, the fluidic channel comprises a nanochannel. In some embodiments, for any of the methods described above, the fluidic channel is disposed parallel to a surface of a substrate. In some embodiments, for any of the methods described above, the method further comprises generating a histogram distribution to reflect coverage depth for the sample. In some embodiments, for any of the methods described above, the sample comprises circulating fetal cells, circulating tumor cells, or body fluids or tissues. In some embodiments, for any of the methods described above, translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

In some embodiments, a system for characterizing a sample is provided. The system can comprise one or more chambers for labeling sample molecules with at least two labels. The system can comprise a fluidic channel for translocating the labeled sample molecules, in which the fluidic channel is configured to elongate at least a portion of the sample molecule, and wherein the fluidic channel has a length of at least 10 nm and a cross-sectional diameter of less than 5000 nm. The system can comprise a device for detecting coverage depths of signals arising from the labeled samples in the fluidic channels. The system can comprise a processor in data communication with the device, wherein the processor is configured to generate a copy number profile of the sample and eliminate or minimize one or both of: biases caused by label density on the labeled sample molecules: or biases caused by factors other than label density of the labeled sample molecules. In some embodiments, minimizing or eliminating bias comprises normalizing scaled coverage depths by characteristic molecular length of the labeled sample molecules. In some embodiments, generating the copy number profile comprises: generating a raw coverage depth profile per label, transforming the raw coverage depth profile to a corresponding scaled label coverage depth profile, generating a sample-specific characteristic molecular length, parameterization comprising gradient and zero-order coefficient values, label filtering based on relative errors, base error, or magnitude of the zero-order coefficient, and normalizing scaled label coverage depths with respect to the sample-specific characteristic molecular length. In some embodiments, generating the copy number profile comprises performing SIngle MOlecule Normalization to Detect Aberrations (SIMONIDA). In some embodiments, generating the copy number profile comprises: generating a raw coverage depth profile per label; transforming the raw coverage depth profile to a corresponding scaled label coverage depth profile; generating a sample-specific characteristic molecular length; parameterization comprising gradient and zero-order coefficient values; label filtering based on relative errors, base error, or magnitude of the zero-order coefficient; and normalizing scaled label coverage depths with respect to the sample-specific number of characteristic labels per labeled sample molecule, or characteristic number of labels within a segment of predetermined length per labeled sample molecule. In some embodiments, scaled label coverage depths are normalized with respect to the sample-specific number of characteristic labels per molecule. In some embodiments, scaled label coverage depths are normalized with respect to the characteristic number of labels within a segment of predetermined length per labeled sample molecule. In some embodiments, the segment of predetermined length per labeled sample molecule comprises 100 kb of nucleic acid. In some embodiments, generating a copy number profile comprises Sex Chromosome Normalization. In some embodiments, generating a copy number profile comprises robust linear regression of scaled label coverage depths. In some embodiments, generating a copy number profile comprises: scaling a plurality of scaled label coverage depths for a training sample based on the number of sex chromosomes in the training sample; and normalizing the scaled label coverage depths with respect to characteristic molecular length of the labeled sample molecules, when present, and further comprises dividing normalized label coverage depths by a median of normalized coverage depths for a plurality of sex chromosomes of a training set. In some embodiments, generating the copy number profile comprises Global Renormalization of Optical Maps (GROM). In some embodiments, GROM comprises: generating a raw coverage depth profile per interval, transforming the raw coverage depth profile to a corresponding scaled coverage depth profile per interval, generating a sample-specific label density bias coefficient (LDBC), parameterizing intervals, wherein the interval parameters comprise gradient and zero-order coefficient values, filtering intervals based on at least on measurement of error, normalizing scaled coverage depth with respect to LDBC, and generating of copy number profiles from the normalized coverage depth profiles. In some embodiments, the processor is configured to automatically determine a presence or absence of possible structural variation in the first genomic fragment or fragments of interest. In some embodiments, the processor is configured to automatically identify possible breakpoints in the copy number profile, wherein an interval in the copy number profile with a significantly different copy number than a neighboring interval comprises a possible breakpoint. In some embodiments, the processor is configured to automatically determine statistically significant differences in an SIMONIDA copy number copy number. In some embodiments, the processor is configured to automatically determine SIMONIDA copy number breakpoints. In some embodiments, the processor is configured to automatically determine statistically significant differences in a GROM copy number. In some embodiments, the processor is configured to automatically determine GROM copy number breakpoints. In some embodiments, the processor is further configured to identify overlap between the GROM copy number breakpoints and the SIMONIDA copy number breakpoints. In some embodiments, the processor is further configured to, for each of the GROM copy number breakpoints, identify a first region of a reference sequence on a first side of the breakpoint, and masking a second region of the reference sequence on a second side of the breakpoint, wherein the second side is opposite the first side; and score only single molecule alignments that align with the reference in the first region. In some embodiments, the processor is further configured to determine a plurality of possible structural variants using a second method, and identify overlap between the GROM copy number breakpoints or SIMONIDA copy number breakpoints and the plurality of possible structural variants determined by the second method. In some embodiments, the processor is further configured to, for each of the GROM copy number breakpoints, identify a first region of a reference sequence on a first side of the breakpoint, and masking a second region of the reference sequence on a second side of the breakpoint, wherein the second side is opposite the first side: and score only single molecule alignments that align with reference labels in the first region. In some embodiments, the fluidic channel is a nanochannel. In some embodiments, the fluidic channel is disposed parallel to a surface of a substrate. In some embodiments, the system is further configured to generate a histogram distribution to reflect coverage depth for the sample. In some embodiments, the sample comprises circulating fetal cells, circulating tumor cells, or body fluids or tissues. In some embodiments, the translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

In some embodiments, a kit for performing any of the methods described above is provided.

In some embodiments, a kit for using any of the systems described above is provided.

BRIEF DESCRIPTION OF THE DRAWINGS

FIG. 4D is a graph illustrating BP of the DNA plotted against Gaussian peak of the intensity of the histogram/100. Unknown molecule sizes and quantities can be extrapolated by this method within a linear dynamic range.

FIG. 5A is a graph illustrating the number of DNA particles per scan based on a linear dynamic range for an 834 bp DNA. FIG. 5B is a graph illustrating the number of DNA particles per scan based on a linear dynamic range for an 233 bp DNA. As such, it is contemplated that in accordance with some embodiments herein, the concentration of a DNA of similar size can be extrapolated and measured, and further a long range of concentrations can be covered by changing the loading parameters.

FIG. 30A is a graph illustrating GROM copy number profile of Chr6 (trace line) is overlapped with automated RPSA complex SV calls (vertical lines 10) in accordance with some embodiments herein. The horizontal lines indicate the expected (integer) copy-number elevations. FIG. 30B is a graph illustrating negative logarithm (base 10) of p-values associated with changes in copy number profiles in accordance with some embodiments herein. Vertical lines: RPSA complex SV calls that do not overlap (10) or do overlap (20, 21, 22) with p-value peaks exceeding the cutoff of 10.

FIG. 37A is a graph illustrating distribution of gradient values per label in accordance with some embodiments herein.

DETAILED DESCRIPTION

Figure 1:
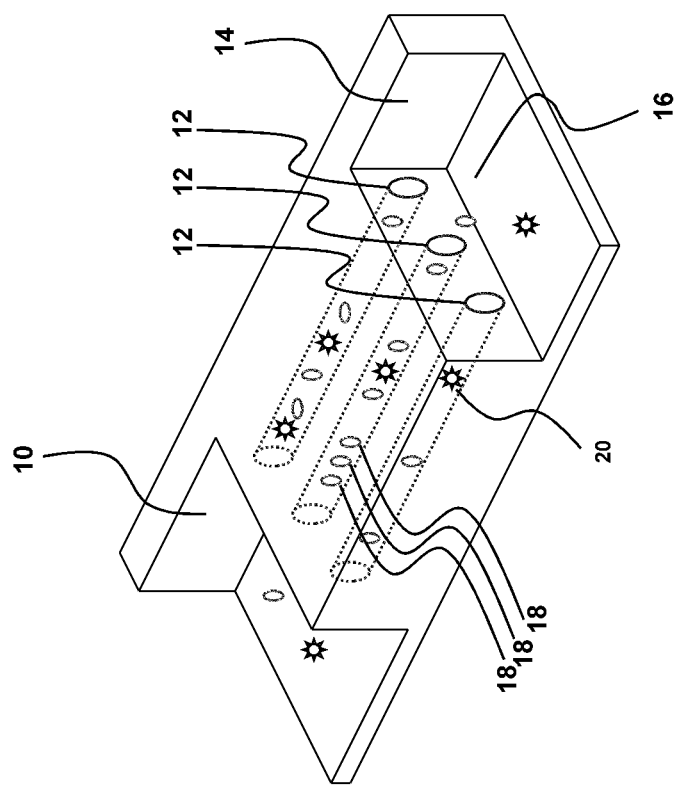
FIG. 1 is a schematic diagram illustrating sample molecules or particles (ovals) and reference or comparative molecules or particles (spheres) flowing through nanofluidic channels, in accordance with some embodiments herein.

According to some embodiments herein, copy number profiles of nucleic acids in a sample, for example chromosomes or fragments thereof are determined. If the copy number values per label contain any features (such as elevations or depletions), the locations and endpoints of these features in the genome can be used to characterize the genome and to identify duplications, deletions, and complex genomic rearrangements (such as translocations). Quantification of chromosomes or fragments thereof, has a variety of applications, for example identification of fetal chromosome number in prenatal testing, and identification of genetic abnormalities such as duplications, deletions, or translocations. According to some embodiments, sample nucleic acid molecules are labeled, linearized in a fluidic channel, and patterns characteristic of the labels are identified on the molecules. The relative quantity or strength of signals corresponding to a chromosome or fragment of interest can be compared to a reference genomic region to determine coverage depth of the genomic region and generate a copy number profile. In some embodiments, methods and systems are provided for improving the quality of copy number profile determinations. It is contemplated that genomic coverage maps can be subject to two kinds of bias: (1) biases caused by label density and (2) biases introduced by factors other than label density. In accordance with some embodiments herein, methods and systems are provided for the accurate determination of the amount of genomic material originating from one or more particular genomic regions. The methods and systems can account for coverage depths per label and/or labels per molecule, and/or labels within a segment of predetermined length per molecule, and/or average per-label coverage of genomic intervals to minimize or eliminate bias. The methods and systems can further account for biases characteristic of sex chromosomes. In some embodiments, biases caused by label density and/or biases introduced by factors other than label density are minimized or eliminated. In some embodiments, coverage depth or copy number profiles are determined automatically. In some embodiments, methods and systems are provided for reliably automatically identifying structural variants in a sample, for example deletions, duplications, or translocations Complex genomic rearrangements, including translocations, were previously difficult to identify and characterize using NGS or microarrays. Although some individual translocations have been detected using analysis techniques such as microarrays or NGS, these techniques are not readily amenable to reliable automated workflow that can confidently calls translocations on a genome-wide scale. According to some embodiments herein, genomic mapping data are used to reliably call complex genomic rearrangements in a manner that is amenable to automated workflow.

The fetus sheds small DNA fragments into the maternal bloodstream. Tumors have also been found to release DNA into the bloodstream. According to some embodiments herein are methods for analyzing polynucleotide fragments such as DNA fragments in blood to detect the presence of circulating polynucleotide or cells from a fetus or tumor. Also according to some embodiments herein are methods for analyzing fetal DNA in maternal blood to detect genetic abnormalities. In some preferred embodiments, the methods described herein entail the use of a nanofluidic-based single molecule detecting platform to identify genetic abnormalities. Methods and apparatuses in accordance with some embodiments herein have the advantage of analyzing small or large molecules, such as small or large DNA molecules. In some embodiments, the sample comprises a plurality of short nucleic acid molecules such as DNA's or RNA's, for example molecules of about 10-2000 bp. In some embodiments, a molecule or region of interest is labeled with at least one pattern, and a reference molecule or region of interest is labeled with at least one pattern. The molecules can be linearized in a microfluidic channel, and coverage depth for the molecule or region of interest can be compared to coverage depth for the reference molecule so as to determine copy number of the molecule of interest.

A genome comprises an organism's polynucleotide sequences, and can comprise DNA, RNA, or a combination thereof. It is noted that a genome or genomic fragment can be packaged with other molecules, for example chromatin, and a packaged genome or genomic fragment can comprise epigenetic features such as methylation or acetylation. Accordingly, a "genome" or "genomic fragment" as used herein can be characterized by genomic features such as polynucleotide sequences, and/or epigenetic features such as methylation patterns or chromatic packaging. As such, sample molecules comprising a genome or genomic fragment in accordance with some embodiments herein can comprise DNA, RNA, DNA and/or RNA packaged with chromatin, and other forms of genomic fragments, and as such, can be characterized by polynucleotide sequence patterns, and/or by patterns of epigenetic features. While methods in accordance with some embodiments herein can be suitable for samples that comprise amplified nucleic acids (e.g. via PCR, isothermal amplification, rolling circle amplification, and the like), it is contemplated that amplification of nucleic acids can produce additional bias, for example as an artifact of the amplification. It is contemplated that samples that have not undergone nucleic acid amplification can exhibit less bias in comparison to those that have. Accordingly, more preferably, samples in accordance with some embodiments herein comprise nucleic acids that have not been amplified. However, as methods in accordance with some embodiments herein are suitable for reducing or eliminating bias in amplified samples, in some embodiments, the sample comprises amplified nucleic acids, for example via PCR, isothermal amplification, rolling circle amplification, and the like.

As used herein "interval" refers to a partition of a genome. In some embodiments, a genome can be partitioned into a plurality of intervals, so that each interval refers to a genomic region. The portioning can be performed in silico, and as such, partitioning a genome into intervals does not require physically cutting or separating out genomic material. Optionally, the intervals are the same size. Optionally, some, but not all of the intervals are a different size from each other. Optionally, each of the intervals is a different size from each of the other intervals. For example, a genome of 10 kb could be partitioned into 5 intervals that are each 2 kb in size, or 5 intervals of different sizes (e.g. 3 kb+3 kb+3 kb+0.5 kb+0.5 kb). One skilled in the art will appreciate that various other terminologies for partitions of the genome, or groupings of partitions of the genome, can also be identified as intervals.

As used herein, "coverage depth" refers to the number of detected sample molecules that map to one or more regions of a genome. As such, coverage depth can be determined based on quantities of labels that map to one or more regions of the genome. Coverage depth can be for genomic sequences, or epigenetic features, such as methylation or acetylation. For example, coverage depth can be depicted as a histogram of genomic coverage depths over a range of genomic regions or "intervals". Moreover, coverage depth can be used to determine a "copy number profile."

As used herein, a "copy number profile" refers to a relative or absolute number of each of a plurality of chromosomes or portions thereof in a sample. For example, a copy number profile can indicate a relative or absolute copy number for each of a plurality of genomic intervals in a sample. As such, a copy number profile can provide insight into the copy number of various portions of the genome, for example elevations and depletions of portions of a sample chromosome so as to indicate duplication, deletions, and complex genomic rearrangements.

A copy number profile can be calculated using raw label coverage values, for example, the number of mapped molecules for one or more types of sequence or epigenetic labels. It is contemplated herein that experimental bias (e.g. label density bias) and/or biological bias (e.g. multiple breakpoints associated with complex genomic rearrangements such as cancer genomes) can interfere with accurate determination of copy number. Methods and systems in accordance with embodiments herein can minimize or eliminate such bias, thus improving the quality of a copy number profile.

It is further noted that a copy number profile accounts for not only the quantity of a label, but also the quantity of particular genomic regions in the context of the genome. By way of example, two copies of "Label 1" in the absence of additional information could indicate any of an intra-chromosome duplication, an inter-chromosome duplication, or mutation in an irrelevant sequence that results in labeling of that sequence by "Label 1". On the other hand, a copy number profile indicating 2× coverage of an X chromosome and 2× coverage of an autosome in a male could be indicative of a chromosomal abnormality such as Klinefelter syndrome (XXY). As such, methods and systems in accordance with some embodiments herein can improve the quality of copy number profiles by minimizing or eliminating bias, so as to provide a copy number profile reflecting genomic copy number rather than artifacts of labeling.

It is estimated that about 3-15% of short DNAs in maternal blood are fetal derived. Described herein are methods of easily detecting and quantitating small molecules, including short DNA fragments, using methods that incorporate fluidics. In some preferred embodiments, the methods comprise quantitating short DNA fragments without sequencing or assembly. As it is contemplated that a maternal blood sample can comprise a mixture of maternal and fetal-derived genomic fragments, it is contemplated that a copy number profile in such a mixed sample can comprise an intermediate value between a euploid maternal genome and aneuploid fetal genome. By way of example, if a sample comprises a mixture of euploid maternal genomic fragments, and aneuploid fetal fragments with trisomy 21, the copy number profile for the sample can indicate a copy number of chromosome 21 that is greater than 2 but less than 3. As such, methods and systems in accordance with embodiments herein that can determine a copy number profile while minimizing or eliminating bias, and thus minimizing or eliminating error can be useful for sensitively detecting fetal chromosomal abnormalities in a maternal sample.

It is contemplated that methods in accordance with embodiments herein can identify complex genomic rearrangements characteristic of cancer cells. Accordingly, methods and/or systems in accordance with some embodiments herein provide a copy number profile for a cancer cell or plurality of cancer cells, for example a tumor biopsy.

Current prenatal tests involving needle puncture to draw amniotic fluid can lead to miscarriage and other complications. Further, many current cancer detection methods also involve invasive procedures, such as biopsies. According to some embodiments herein, a non-invasive method of prenatal testing is provided. In some embodiments, the method is for testing blood. In some embodiments, the method only tests a blood sample, and does not test a sample from other tissues.

Also described herein are methods of detecting and tracking larger molecules, including longer DNA fragments, to their source using methods that incorporate fluidics. For example, in some embodiments, DNA fragments are tracked back to a tumor or other source of cancer. In some preferred embodiments, the methods are used to track DNA fragments to their source in order to identify or characterize a genetic abnormality.

In some embodiments, circulating DNA from a maternal blood sample is analyzed to identify and quantify fetal DNA relative to the maternal genome. In some embodiments, this information is used to determine prenatal genomic health status (such as trisomy 21) without invasive tests. Examples of suitable oligos for use in an assay for detecting aneuploidy are provided in the HSA21 oligoarray described in Yahya-Graison et al., Classification of Human Chromosome 21 Gene-Expression Variations in Down Syndrome: Impact on Disease Phenotypes, Am J Hum Genet 2007, 81(3): 475-491, which is hereby incorporated by reference in its entirety.

In some embodiments, a sample of interest is compared to a reference. The reference can comprise a reference genome or one or more portions of a reference genome. Labels identifying genomic sequences or epigenetic patterns in the sample can be correlated to those of the reference. In some embodiments, the reference genome comprises an annotated human reference genome such as hg19 or GRCh38. In some embodiments, the reference genome comprises hg19. In some embodiments, the reference genome comprises GRCh38. In some embodiments, the reference comprises digital digested in silico barcodes derived from a reference genome, such as hg19 or GRCh38. For example, if a sample is labeled at a particular sequence motif, patterns of that motif within the reference genome can be determined in silico, and sample molecules can be aligned to the in silico-determined patterns to determine coverage depth for the reference genome. In some embodiments, the reference comprises an electronically stored set of values. In some embodiments, the reference comprises an optically stored set of values. In some embodiments, the reference comprises a labeled reference molecule. Optionally, the reference comprises a molecule from a sample known not to contain an abnormality. Optionally, the reference comprises a region of the genome known not to contain an abnormality (e.g. an autosome for which aneuploidy is not typically viable, for example chromosome 1). In some embodiments, the sample of interest is derived from a maternal blood sample. In some of these embodiments, the reference sample is a maternal sample from a source other than blood. In some embodiments, the maternal reference sample includes polynucleotides such as DNA isolated from a diploid tissue other than blood. In some embodiments, the maternal reference sample comprises a buccal sample, a saliva sample, a urine sample, a sputum sample, or a tear sample. For example, in some embodiments, trisomy 21 is detected in a maternal blood sample compared to a maternal buccal sample.

In some embodiments, the methods and/or systems herein use a reference from the same organism as the sample molecules, for example the same individual, or a different individual of the same species. In some embodiments, the methods and/or systems herein use a reference from a different tissue of the same organism as the sample molecules (for example, the same individual, or a different individual of the same species), for example a tissue known not to comprise a chromosomal abnormality. In some embodiments, the methods and/or systems herein use a reference from a different organism than the sample molecules. The different organism can be from the same species as the sample molecules.

In some embodiments, the sample of interest is enriched for fetal nucleic acids prior to performing the methods described herein. For example, in some embodiments, fetal cells are enriched using a fetal cell specific marker that can be pulled down by an antibody. In some embodiments, the sample of interest undergoes size fractionation. However, any method of enrichment known to one of skill in the art can be used.

In some embodiments, the sample of interest is derived from a tumor cell or suspected tumor cell, or a tissue in fluid communication with a tumor cell (for example, blood). In some embodiments, the reference sample is sample from a healthy cell. In some embodiments, the reference sample is from a healthy cell of the same organism as the tumor cell or suspect tumor cell. In some embodiments, the reference sample is selected from a tissue that has little to no likelihood of comprising a tumor cell or nucleic acid from the tumor cell.

As one of skill in the art will recognize, the sample of interest may include nucleic acids from a variety of sources. In some embodiments, the sample of interest comprises a bacteria or virion derived from an environmental sample, animal or plant tissue, blood, or other body fluid. In some embodiments, DNA fragments are used to detect chromosomal abnormalities or cancer genomes.

As one of skill in the art will recognize, the methods described herein can be used to prepare and analyze DNA from circulating fetal or tumor cells. For example, in some embodiments, cells are lysed to release DNA of interest prior to analysis.

In some embodiments, an entire genome is assayed or analyzed. In some embodiments, only a portion of a genome is assayed or analyzed. In some embodiments, an entire chromosome is assayed or analyzed. In some embodiments, only a portion of a chromosome is assayed or analyzed. In some embodiments, an entire gene is analyzed. In some embodiments, only a portion of a gene is assayed or analyzed.

The signals described herein can include any suitable signal, including optical signals, fluorescent signals, non-optical signals, radiative signals, electrical signals, magnetic signals, chemical signals, or any combination thereof. In some embodiments, signals are generated by an electron spin resonance molecule, a fluorescent molecule, a chemiluminescent molecule, a radioisotope, an enzyme substrate, a biotin molecule, an avidin molecule, an electrical charged transferring molecule, a semiconductor nanocrystal, a semiconductor nanoparticle, a colloid gold nanocrystal, a ligand, a microbead, a magnetic bead, a paramagnetic particle, a quantum dot, a chromogenic substrate, an affinity molecule, a protein, a peptide, a nucleic acid, a carbohydrate, an antigen, a nanowire, a hapten, an antibody, an antibody fragment, a lipid, or a combination thereof.

In some embodiments, signals are generated by using one or more excitation sources to induce fluorescence, chemoluminescence, phosphorescence, bioluminescence, or any combination thereof. Suitable excitation sources include lasers, visible light sources, sources of infrared light, sources of ultraviolet light, or any combination thereof.

Figure 3:
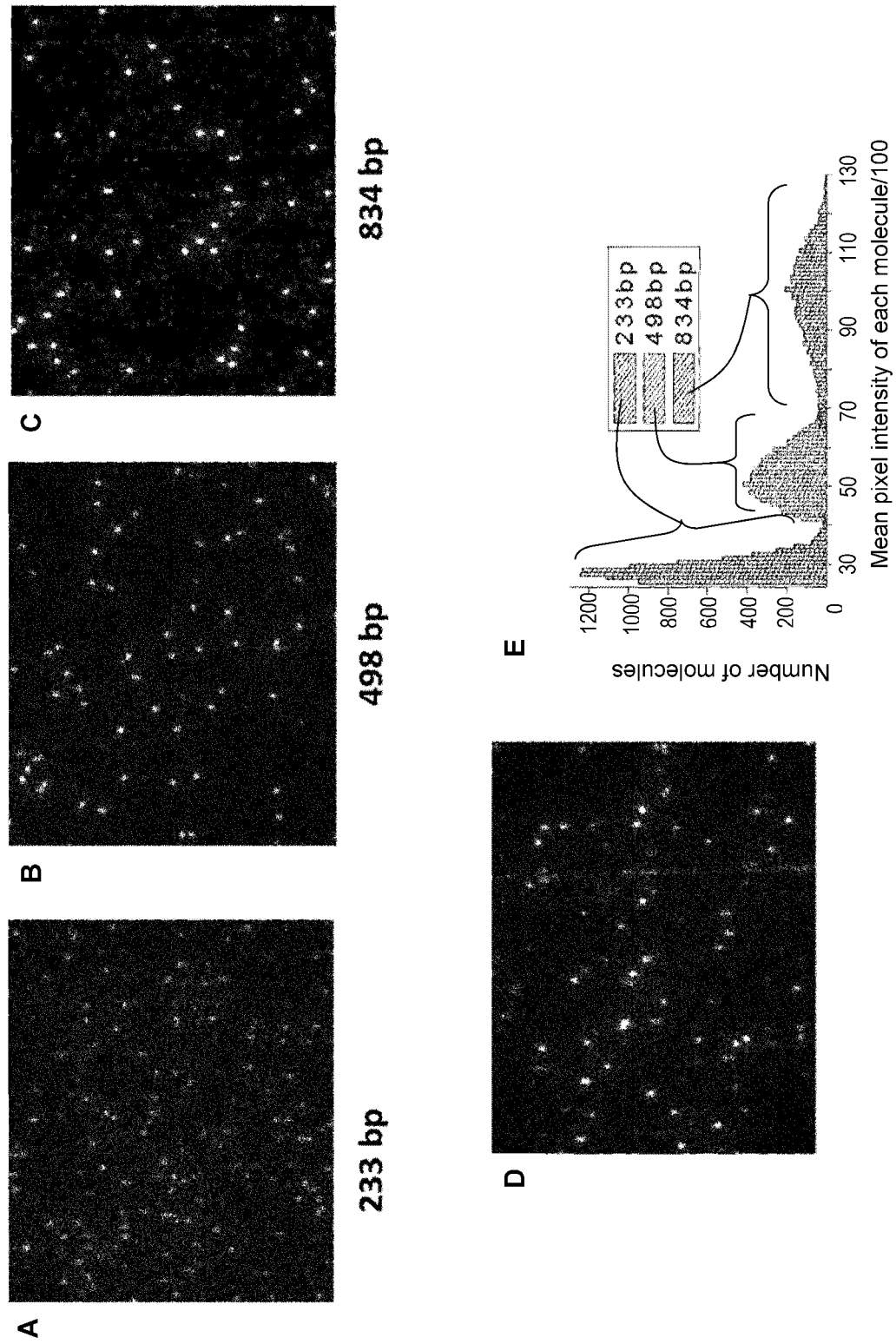
FIGS. 3A, 3B, and 3C are a series of images illustrating small double stranded DNA fragments with known sizes in: 233 bp (FIG. 3A), 498 bp (FIG. 3B), and 834 bp (FIG. 3C) that were generated by PCR, fluorescently stained, flowed, and imaged in individual nanofluidic channels in accordance with some embodiments herein.
FIG. 3D shows the same double stranded DNA fragments that were mixed together, flowed, and imaged in the same nanofluidic channel in accordance with some embodiments herein. The fluorescent signals were plotted in a histogram (FIG. 3E).
Figure 4:
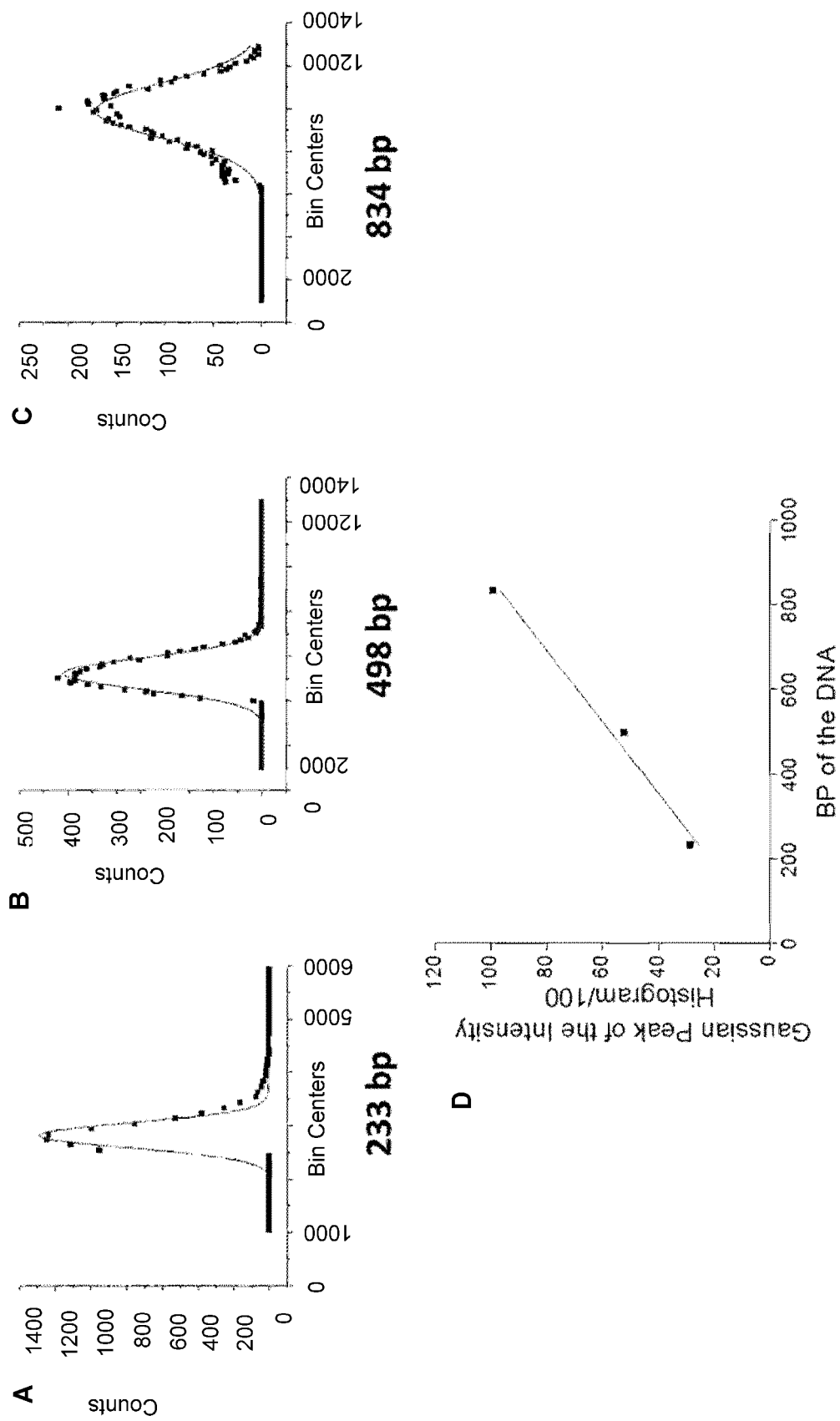
FIG. 4 is a series of graphs illustrating linearity of intensity measurements of small DNAs. Shown are Gaussian curves depicting the photons emitted from individually labeled DNA molecules with known sizes: 233 bp (FIG. 4A), 498 bp (FIG. 4B), and 834 bp (FIG. 4C) in accordance with some embodiments herein. Total coverage depths and intensity were linearly proportional to mass and/or molecule size.
Figure 5:
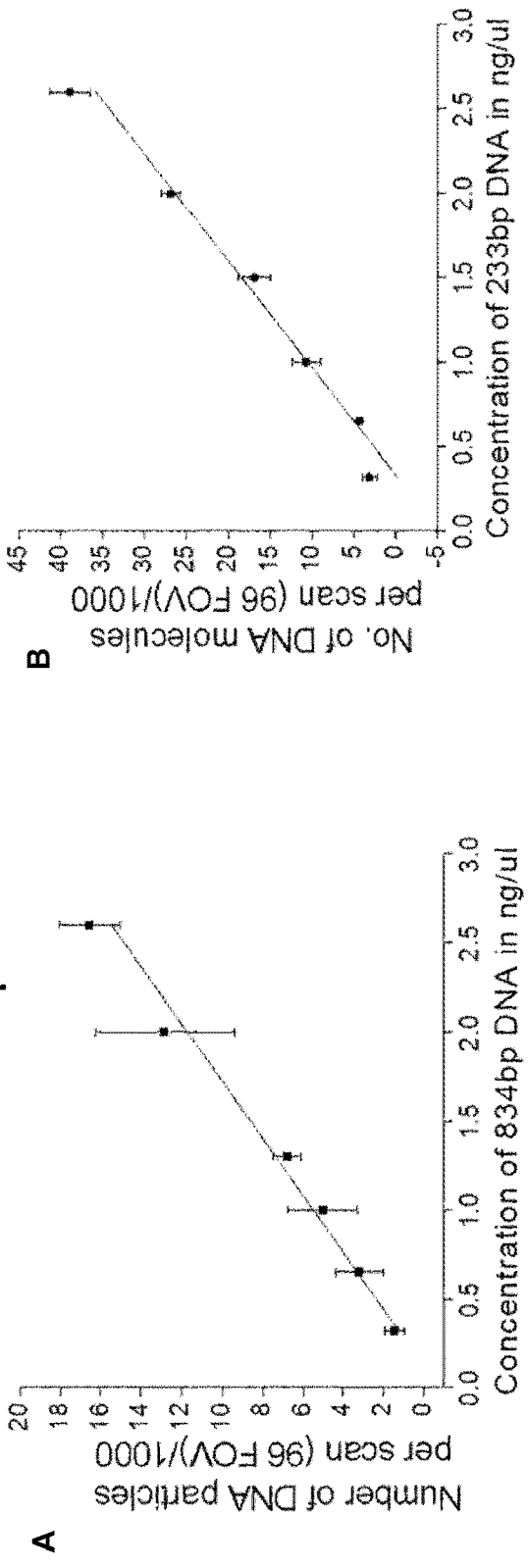
FIG. 5 is a series of graphs illustrating quantitative measurement of small molecule fragments or particles. The concentrations of molecules of unknown quantities within a linear dynamic range were extrapolated using the information from FIG. 4 in accordance with some embodiments herein.
Figure 6:
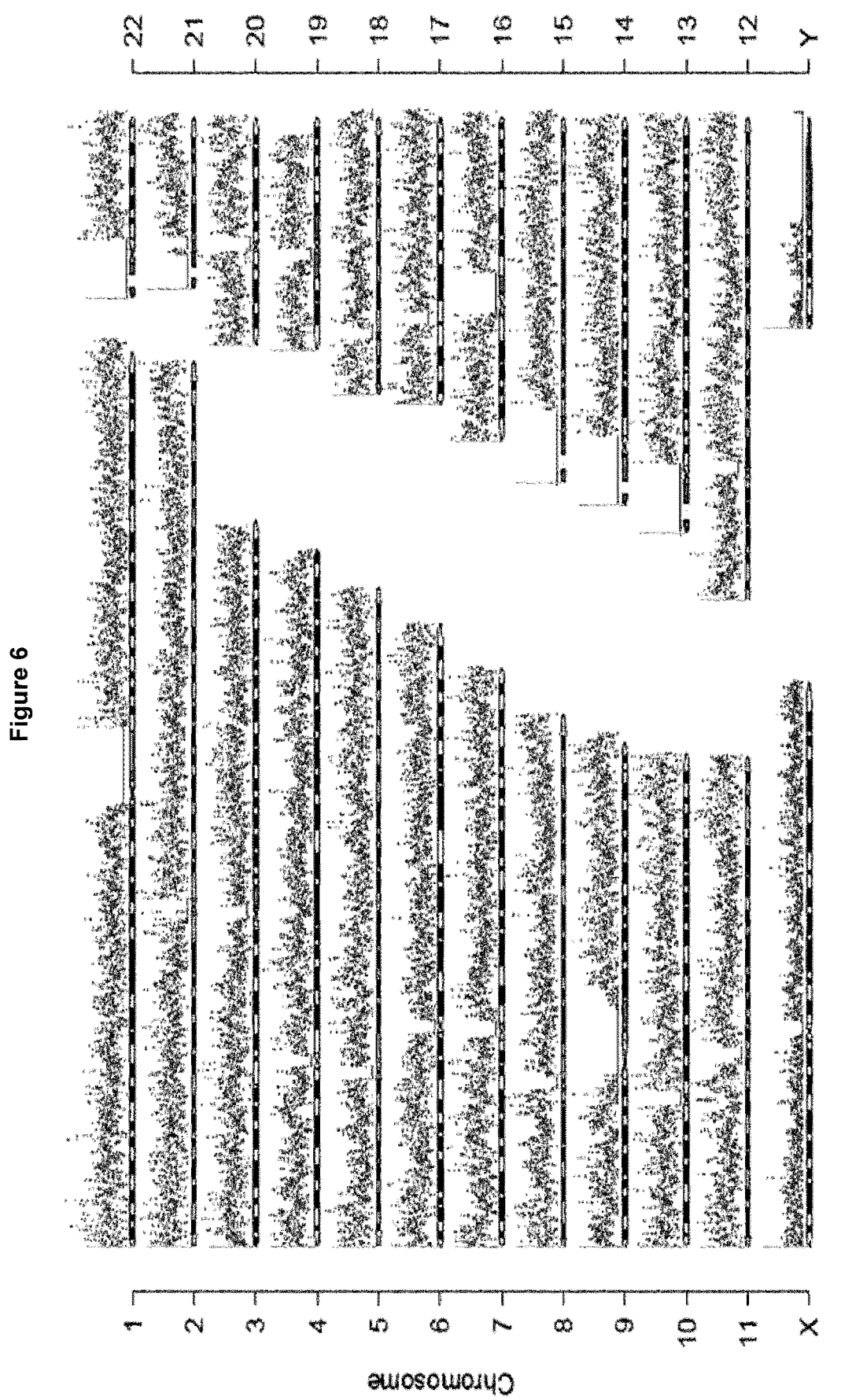
FIG. 6 is a histogram illustrating genomic DNA fragments plotted against a reference genome (human genome version 19) in accordance with some embodiments herein. The y-axis shows coverage depth for specific chromosomal regions. A uniform distribution throughout the genome was observed, except for regions without sequence information (such as the centromeres and telomeres).

In some embodiments, the detection of nucleotides or associated signals (for example, fluorophores) is quantitative. In some embodiments, the length of a nucleotide is quantified. In some embodiments, the size of a molecule is quantified. In some embodiments, the strength of a signal correlates with the length of a molecule. For example, as shown in FIG. 3A, longer DNA molecules can generate stronger signals than shorter DNA molecules. In some embodiments, the strength of a signal correlates to the amount of DNA in a sample or fluidic channel.

In some embodiments, samples are analyzed for copy number variation, for example, as described in U.S. Patent Publication No. 20130034546, which is hereby incorporated by reference in its entirety.

The quantity of particular molecules, such as DNA fragments derived from different chromosomes, can be quantitatively measured in the methods provided herein. In some embodiments, the amount of genomic DNA derived from a diploid autosomal chromosome is observed to be twice as much as that derived from a haploid sex chromosome. In some embodiments, the quantity of such fragments reflects the copy number of a source chromosomes. In some embodiments, two or three color labels are used.

In some embodiments, chromosome derived fragments are detected, and a relative ratio is used to identify aneuploidy. In some embodiments, the copy number of a nucleotide is calculated using the ratios $K1=S1/C$ and $K2=S2/C$, wherein K1 is the ratio of the signal for a first sample to a control sample, and K2 is the ratio of the signal for a second sample to the control sample. It is contemplated that the copy number from the reference sample is an integer, and that the difference between K1 and K2 can indicate an abnormality in one of the samples of interest. In some embodiments, the abnormality is detected by comparing the ratio for a particular sample to the average ratio from a plurality of samples. The methods further contemplate that the control genomic sequence includes separate portions whose total length per genome is known, wherein the sequence of interest comprises separate portions whose length per normal gene is known, and wherein a significant difference between K1 and K2 indicates a genetic abnormality in the genome. In some embodiments, the nucleotide sequence of interest can relate to a trisomy-linked chromosome, wherein the control genomic sequence is from a chromosome other than the trisomy-linked chromosome, and wherein a K1/K2 ratio of approximately 2:3 or 3:2 indicates a trisomic genotype. In some embodiments, the nucleotide sequence of interest comprises a deletion of a portion of a genome. In some embodiments, the nucleotide sequence of interest comprises a repeating sequence. As such, a copy number of repeating sequence can be determined according to some embodiments herein. In some embodiments, the first sample comprises maternal blood (which, without being limited by any one theory, may include fetal nucleic acids), and the second sample comprises maternal tissue other than blood (preferably a tissue with little to no likelihood of comprising fetal nucleic acids).

In some embodiments, digital counting detection is performed. In some embodiments, digital counting detection is performed on particles (such as beads), bacteria, or virion particles. As one of skill in the art will recognize, the methods described herein can apply to a variety of targets that can be uniquely labeled. In some embodiments, digital karyotyping is performed. For example, in some embodiments, digital karyotyping is performed for a chromosome with potential aneuploidy of interest. The methods described herein can be used to detect any chromosomal variation of interest, including translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy, tetraploidy, and sex chromosome abnormalities, including but not limited to XO, XXY, XYY, and XXX. It is noted that a number of organisms and genomes, such as plants, fungi, algae, bacteria, and viruses do not typically comprise sex chromosomes. It is contemplated that methods and apparatuses in accordance with embodiments herein, in addition to being applicable to organisms and genomes that comprise sex chromosomes such as animals, are also applicable to organisms and genomes that do not comprise sex chromosomes such as plants, fungi, algae, bacteria, and viruses.

Minimization and Elimination of Bias in Mapping Coverage by GROM

Also described herein are methods for normalization of genomic analysis data, for example maps. The methods for normalization can be used in conjunction with other methods herein, for example to reduce bias related to label density, and/or bias related to factors other than label density. For example, the methods can reduce bias related to GC content.

GC-related systematic biases can array and next generation sequence (NGS) coverage measurements of polynucleotide sequences. Various approaches to alleviate effects of GC bias include additive removal of GC bias, multiplicative GC correction, and quantile normalization have been unsuccessful. Without being limited by any theory, none of these previous approaches fully remove all the biases, primarily because they fail to separate GC bias from location-specific, non-GC-related biases.

Parameterized Error Removal and Unbiased Normalization (PERUN; see U.S. Pub. No. 2013/0325360, hereby incorporated by reference in its entirety) can achieve complete removal of NGS-specific biases from coverage profiles by aligning sequenced short Illumina reads to the human reference genome, partitioning the reference genome into bins, counting reads that map within each bin, evaluating sample-specific GC bias coefficients, performing regression of raw bin counts (scaled with respect to total raw bin counts) versus sample-specific GC bias coefficients for multiple samples, and by employing cross-validation based on R-factors. The bin-specific regression coefficients can be used to parameterize each bin and to correct for both GC and non-GC bin-specific biases, taking into account the sample-specific GC coefficient. The cross-validation can be used to filter out unreliable genomic bins. Further filtering of bins can be performed based on bin mappability/repeatability measures. In some embodiments, polynucleotides can be sequenced, and PERUN can be used to remove or minimize GC bias.

Disclosed herein is Global Renormalization of Optical Maps (GROM). In some embodiments, GROM eliminates or minimizes bias from coverage maps of long polynucleotide sequences, for example genomic regions. It is noted that while the acronym "GROM" includes the term "optical maps", it is contemplated herein that GROM is also applicable to non-optical labeling. For conciseness, the term GROM is used throughout this application with the understanding that it is applicable to renormalization of non-optical as well as optical coverage maps. In labeled mapping of polynucleotides in accordance with some embodiments herein, for example optical labeling, label density-related biases can depend on the distribution of molecular lengths observed in a given sample. The label density biases, in addition to being specific to genomic locations, can also reflect the experimental conditions under which a given data set is collected. Therefore, the label density bias varies from sample to sample. The biases caused by factors other than label density are insensitive to molecular lengths. As a result, these biases can be the same for a plurality of samples, for example all samples being examined. In some embodiments, minimizing or removing both types of biases facilitates determining the amount of genomic material originating from a given genomic region.

In some embodiments, GROM is applied to coverage maps obtained by assembly of labeled polynucleotides as described herein. In some embodiments, the coverage maps are obtained by optical labeling. In some embodiments, the coverage maps are obtained by non-optical labeling (it is contemplated that GROM can eliminate or minimize bias due to various types of label density as described herein, and as such, can readily be adapted to optical and non-optical labeling). In some embodiments, GROM eliminates or minimizes biases caused by label density. In some embodiments, GROM eliminates or minimizes biases introduced by factors other than label density. In some embodiments, GROM eliminates or minimizes biases caused by label density and biases introduced by factors other than label density.

In some embodiments, GROM accurately estimates copy number profiles starting from raw label coverage values. In some embodiments, the raw label coverage values are obtained via detection of labeled polynucleotides as described herein. In some embodiments, the raw label coverage values are stored in a computer readable medium. For example, the raw label coverage values can be reported in the Coverage field of CMAP files. If the GROM copy number profiles contain any features (such as elevations or depletions), the locations and endpoints of these features can be used to characterize the genome and to identify large-scale duplications, deletions, and complex genomic rearrangements (such as translocations).

In some embodiments. GROM comprises generation of a raw coverage depth profile, its transformation to the corresponding scaled coverage depth profile, generation of the sample-specific label density bias coefficient (LDBC), interval parameterization involving gradient and zero-order coefficient values, interval filtering based on relative errors (or other measures of error), normalization of scaled coverage depth with respect to LDBC, and generation of copy number profiles from the normalized coverage depth profiles.

In some embodiments. GROM normalization utilizes Equation 1, wherein I=chromosomal elevation; wherein C=scaled raw coverage depths; wherein E=interval-specific zero-order coefficient (expected coverage depth in absence of biases); wherein G=interval-specific gradient (susceptibility of an interval to biases, roughly equal to number of labels within the interval), and wherein L=sample-specific label density bias (gradient of the coverage depth-vs-number of labels regression, sample's response to experimental conditions).

$$I=(1/E)*(C-G*L) \qquad \text{Equation 1}$$

In some embodiments, labels on sample molecules are detected as described herein. In some embodiments, raw read coverage depths are obtained. Raw read coverage depths can be obtained as follows: For each interval, sum up coverage values for all labels within the interval; divide the sum by the number of labels; and assign the average label coverage to the interval. In some embodiments, the raw read coverage depths (also referred to herein as "raw coverage") comprises one or more of the following characteristics: proportional to the amount of chromosomal material in the sample; elevation of sex chromosomes sufficient to determine sex; aneuploidy in cancer samples evident from raw coverage depths; repeated measurements on the same individual yield highly correlated raw coverage depth profiles; can divide raw coverage depth by total autosomal coverage depths to bring all samples to the same scale (for convenience, can also multiply by the number of autosomal intervals); and possible high variance and systematic biases. As such, in some embodiments, biases from raw read coverage depths are minimized or eliminated. In some embodiments, the raw read coverage depths are minimized or eliminated by GROM.

According to some embodiments, GROM includes some or all of the steps shown in Table 1. The skilled artisan will appreciate that steps listed herein can be performed in a different order, eliminated, or duplicated in accordance with some embodiments:

TABLE 1

Collect labeled mapping data on sample molecules. In some embodiments, the mapping data comprises optical mapping data. In some embodiments, the mapping data comprises non-optical mapping data. In some embodiments, the sample comprises a human sample. In some embodiments, the data collection is performed on a Irys ™ system from BioNano genomics.
Perform mapping data processing (e.g. image processing) and quantification of detected molecules.
Apply quality filters to the detected molecules. Suitable filters can include, but are not limited to, signal-to-noise ratio, molecular length, the number of labels per molecule, periodicity of label locations, uniformity of non-specific polynucleotide label (e.g. YOYO or POPO) intensity. The subset of molecules passing the filter will be used for further manipulations.
Select an appropriate reference genome (e.g., hg19 or GRCh38) or genomic portion of interest (optionally, the appropriate reference genome can be pre-selected)
Align the filtered subset of molecules to the reference genome (or genomic portion of interest) of choice (such as hg19 or GRCh38). The output of the alignment can be stored on a computer readable medium. The output of the alignment can include the reference CMAP file (*_r.cmap). The coverage field of this file can list coverage per label.
Partition the reference genome (or genomic portion of interest) into intervals. The intervals may or may not have equal size. In some embodiments, GROM uses intervals of equal size. In some embodiments, the interval sizes are about 50,000 base pairs. Various interval sizes can be used as well, for example about 1,000, 2,000, 5,000, 10,000, 20,000, 30,000, 40,000, 50,000, 60,000, 70,000, 80,000, 90,000, 100,000, 150,000, 200,000, 300,000, 400,000, or 500,000 base pairs, including ranges between any two of the listed values. Various number of intervals can be used, for example, about 5,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, or 100,000, including ranges between any two of the listed values.
Within each interval, select the reference labels located within the interval.
Generate a list containing the number of labels per interval.
Extract the coverage values for the selected labels from the *_r.cmap file.
Sum up the coverage values within the interval and divide the sum by the number of labels. Assign the resulting average per-label coverage to the interval containing the labels. These are raw coverage depth.
Sum up all raw coverage depth corresponding to autosomal intervals (for example, human chromosomes 1 through 22).
Divide all raw coverage depth by the sum of autosomal raw coverage depth. The result is the scaled coverage depth profile. Optionally, the scaling can be done with respect to autosomal intervals only to avoid the variability associated with the sex-dependent copy number of sex chromosomes. In some embodiments, the scaling is to enable comparison between various samples, characterized by different overall coverage levels.
Perform linear regression of scaled coverage depth vs. the number of labels per interval. Optionally, subtract the median number of labels per interval (6 in the case of hg19) from the number of labels per interval to center the abscissa. The gradient of the regression line is the sample-specific Label Density Bias Coefficient (LDBC).
In some embodiments, any or all of the steps described above are applied to multiple euploid human samples of both sexes. The resulting set of measurements constitutes the training set. Optionally, also generate a cross-validation set of measurements.
For each interval along the genome, perform linear regression of scaled coverage depth vs. sample-specific LDBC. The regression can involves all the samples in the training set. The resulting gradient G and zero-order coefficient E can be recorded and assigned to the current interval. The parameters G and E can be used to perform GROM normalization on newly measured samples.
In addition to the gradient and the zero-order coefficient, also record the associated confidence measures (such as standard errors, p-values, confidence intervals, and relative error values). The relative error is defined as the sum of absolute deviations of predicted scaled coverage depths from the observed values, divided by the sum of scaled coverage depth. The relative error can be interpreted as the interval-specific relative error.
Flag all intervals whose relative errors exceed a predefined cutoff. The cutoff reflects the desired level of precision and is based on the overall coverage. As a rule of thumb, the expected error for a given coverage is obtained as the reciprocal square root of the coverage (assuming Poisson distribution). For example, 100x coverage is associated with ~10% relative error, while 36x coverage corresponds to 16% relative error.
Optionally, perform cross-validation of the interval parameters E and G on the cross-validation set of measurements.

TABLE 1-continued

For a newly collected data set, generate scaled coverage depth profile as described above.
Generate the LDBC L for the sample data set as described above.
Use the scaled coverage depth c as an input to evaluate normalized coverage depth n as
follows: n = (c − GL)/E.
Multiply the resulting normalized coverage depth n with chromosome-specific factors (2 for
autosomes and X, 1 for Y) to generate copy-number profile.
Optionally produce a GROM copy number profile
Optionally detect breakpoints in the GROM copy number profile
Optionally identity genetic abnormalities in the sample molecules Unexpectedly, GROM can produce high precision of Chromosome Y coverage depth profiles, in spite of a small number of male training samples available and the known sequential similarity between Chromosome Y and the rest of the genome, in particular Chromosome X.

In some embodiments, GROM produces a GROM copy number profile. The GROM copy number profile can comprise a stepwise function taking values equal to integer multiples of one (starting from zero), with added noise. The relative error can range from 10% to 25% or more, depending on the total coverage, for example about 10% to 25%, about 10% to 35%, about 10% to 45%, about 15% to 25%, about 15% to 35%, about 15% to 45%, about 20% to 25%, about 20% to 35%, or about 20% to 45%. In some embodiments, p-values of $10^{-10}$ are used to identify significant changes in absolute copy numbers. The skilled artisan will appreciate a number of available approaches for calculating relative error, for example R factors and the like.

Minimization and Elimination of Bias in Mapping Coverage by Normalized Copy Number Per Label (SIMONIDA)

GROM as described herein is useful for minimizing or eliminating two type of bias: (1) bias caused by label density, and (2) bias introduced by factors other than label density. It is contemplated herein that minimization or eliminating bias by SIngle MOlecule Normalization to Detect Aberrations (SIMONIDA) can also minimize or eliminate both of these types of bias, and further can offer additional advantages, for example, greater resolution than for a predetermined interval size, and accounting for the biological variability associated with complex genomic rearrangements such as in cancer genomes. It is noted that the approaches of SIMONIDA relate to minimizing or eliminating bias in view of Normalized Copy Number per label, and can also be referred as Normalized Copy number per Label ("NCL"). In some embodiments, SIMONIDA eliminates bias caused by label density, and bias introduced by factors other than label density. In some embodiments, SIMONIDA eliminates bias caused by label density. In some embodiments, SIMONIDA eliminates bias introduced by factors other than label density. In some embodiments, SIMONIDA minimizes bias caused by label density, and bias introduced by factors other than label density. In some embodiments, SIMONIDA minimizes caused by label density. In some embodiments, SIMONIDA minimizes bias introduced by factors other than label density. In some embodiments, SIMONIDA eliminates bias caused by label density and minimizes bias introduced by factors other than label density. In some embodiments, SIMONIDA minimizes bias caused by label density and eliminates bias introduced by factors other than label density.

In accordance with some embodiments herein, SIMONIDA accounts for the coverage depth per label and sample-specific average molecule length to minimize or eliminate bias. It is contemplated herein that label density biases, in addition to being specific to genomic locations, also reflect the experimental conditions under which a given data set is collected. Therefore, the label density bias varies from sample to sample. The biases caused by factors other than label density are insensitive to molecular lengths, and thus are the same for all samples. SIMONIDA in accordance with some embodiments herein can minimize or eliminate both types of bias.

In some embodiments, SIMONIDA comprises generating a raw coverage depth profile per label for a sample. The raw coverage depth profile can be transformed into a scaled label coverage depth profile. Sample-specific characteristic molecule length can be determined. Label parameterization involving gradient and zero-order coefficient values can be performed. Optionally, label-filtering based on relative errors (or other measure of error, such as base error, or other descriptors, such as magnitude of the zero-order coefficient) can be performed. Normalization of scaled label coverage depth with respect to characteristic molecule length can be performed. One or more copy number profiles can be generated from the scaled number profiles. Optionally, measurements of error such as errors evaluated using second-order Taylor expansion can be used as weights when doing numerical processing of copy number profiles, for example, to detect features.

SIMONIDA can include characterizing sample behavior for a training set. Optionally, the training set can comprise a plurality of euploid genomes. For a newly collected data set, scaled label coverage depth profiles can be generated, abscissa values can be calculated, and normalized label coverage depths (n) can be calculated based on behaviors from the training set. It is contemplated that in accordance with some embodiments, if the training set includes male samples, or samples with sex chromosome aneuploidies such as Jacobs syndrome (XYY) and/or Klinefelter samples (XXY), scaled X and/or Y chromosome coverage depths can be adjusted to account for single and/or double copies of either sex chromosome.

Figure 44:
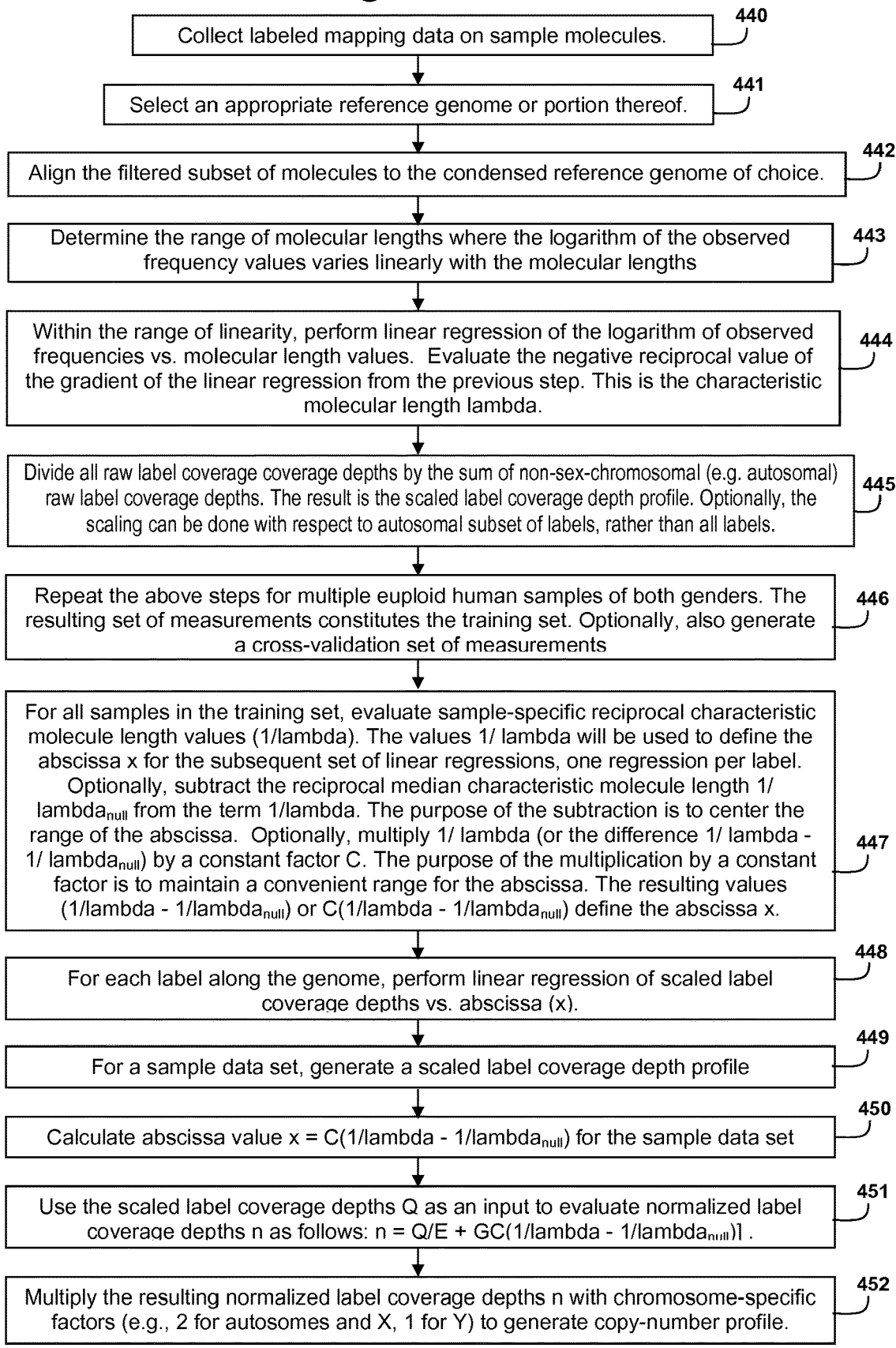
FIG. 44 is a flow diagram illustrating methods for minimizing or eliminating bias in view of normalized copy number per label in accordance with some embodiments herein.

FIG. 44 is a flow diagram illustrating SIMONIDA in accordance with some embodiments herein. SIMONIDA can include collecting labeled mapping data on sample molecules 440. SIMONIDA can include selecting an appropriate reference genome or portion thereof 441. SIMONIDA can include aligning the filtered subset of molecules to the condensed reference genome of choice 442. SIMONIDA can include determining the range of molecular lengths where the logarithm of the observed frequency values varies linearly with the molecular lengths 443. SIMONIDA can include, within the range of linearity, performing linear regression of the logarithm of observed frequencies vs. molecular length values. Evaluate the negative reciprocal value of the gradient of the linear regression from the previous step. This is the characteristic molecular length lambda 444. SIMONIDA can include dividing all raw label coverage depths by the sum of non-sex-chromosomal (e.g. autosomal) raw label coverage depths. The result is the scaled label coverage depth profile 445. It is noted that methods and systems in accordance with some embodiments herein are applicable to organisms and genomes that do not typically have sex chromosomes, such as plants, fungi, algae, bacteria, viruses, and the like. Accordingly, a sum of non-sex-chromosomal label coverage depths can be available for such organisms and genomes, and can also be available for organisms that typically comprise sex chromosomes such as animals (e.g. humans, mammals, or non-human mammals). Optionally, the scaling can be done with respect to autosomal subset of labels, rather than all labels, to avoid the variability associated with the gender-dependent copy number of sex chromosomes. SIMONIDA can include repeating steps 440-445 for multiple euploid human samples of both genders 446. The resulting set of measurements constitutes the training set. Optionally, also a cross-validation set of measurements can also be generated. SIMONIDA can include, for all samples in the training set, evaluating sample-specific reciprocal characteristic molecule length values (1/lambda). The values 1/lambda will be used to define the abscissa x for the subsequent set of linear regressions, one regression per label. Optionally, subtract the reciprocal median characteristic molecule length 1/lambda$_{null}$ from the term 1/lambda. The purpose of the subtraction is to center the range of the abscissa. Optionally, multiply 1/lambda (or the difference 1/lambda−1/lambda$_{null}$) by a constant factor C. The purpose of the multiplication by a constant factor is to maintain a convenient range for the abscissa. The resulting values (1/lambda−1/lambda$_{null}$) or C(1/lambda−1/lambda$_{null}$) define the abscissa x 447. For each label along the genome, perform linear regression of scaled label coverage depths vs. abscissa (x) 448. SIMONIDA can include, for a collected data set from a sample (e.g. a newly collected sample), generating a scaled label coverage depth profile 449. SIMONIDA can include calculating the abscissa value x=C(1/lambda−1/lambda$_{null}$) for the sample data set 450. Optionally, the abscissa value can be calculated without a constant factor as x=(1/lambda−1/lambda$_{null}$). SIMONIDA can include using the scaled label coverage depths Q as an input to evaluate normalized label coverage depths n as follows: n=Q/[E+GC(1/lambda−1/lambda$_{null}$)] 451. SIMONIDA can include multiplying the resulting normalized label coverage depths n with chromosome-specific factors (e.g., 2 for autosomes and X, 1 for Y) to generate copy-number profile 452. The skilled artisan will appreciate that steps listed herein can be performed in a different order, eliminated, or duplicated in accordance with some embodiments:

According to some embodiments, SIMONIDA includes some or all of the steps shown in Table 2. The skilled artisan will appreciate that steps listed herein can be performed in a different order, eliminated, or duplicated in accordance with some embodiments:

TABLE 2

Collect labeled mapping data on sample molecules. In some embodiments, the mapping data comprises optical mapping data. In some embodiments, the mapping data comprises non-optical mapping data. In some embodiments, the sample comprises a human sample. In some embodiments, the data collection is performed on a Irys ™ system from BioNano genomics Perform mapping data processing (e.g. image processing) and quantification of detected molecules.

Apply quality filters to the detected molecules. Suitable filters include but are not limited to signal-to-noise ratio, molecular length, the number of labels per molecule, periodicity of label locations, and uniformity of backbone label (e.g. YOYO, POPO) intensity. The subset of molecules passing the filter will be used for further manipulations.

Select an appropriate reference genome (e.g., hg19 or GRCh38) or genomic portion of interest (optionally, the appropriate reference genome can be pre-selected)

Apply condensation to the selected reference. The initial implementation used the value of 2.9 for the mres option of RefAligner, though it is contemplated that other values are suitable.

Align the filtered subset of molecules to the reference genome (or genomic portion of interest) of choice (such as hg19 or GRCh38). The output of the alignment can be stored on a computer readable medium. The output of the alignment can include the reference CMAP file (*_r.cmap). The coverage field of this file can list coverage per label.

Collect the molecule length values and generate their histogram. Optionally, the molecule length values are collected from a computer readable medium. For example, the molecule CMAP file contains molecule lengths in the ContigLength field.

Starting from the histogram of molecular lengths, evaluate the logarithm of the observed frequencies of molecular lengths.

Determine the range of molecular lengths where the logarithm of the observed frequency values varies linearly with the molecular lengths.

Within the range of linearity, perform linear regression of the logarithm of observed frequencies vs. molecular length values.

Evaluate the negative reciprocal value of the gradient of the linear regression from the previous step. This is the characteristic molecular length λ (lambda).

The output of the alignment also includes a reference, and lists coverage per label. The reference and coverage per label can stored in a computer readable medium. For example, the reference can be stored in a CMAP file (*_r.cmap), and the coverage field of this file can list coverage per label.

Extract the coverage values for the selected labels from the computer readable medium (e.g., the *_r.cmap file).

Sum up all raw label coverage values corresponding to non-sex-chromosomal (e.g. autosomal labels)(e.g., chromosomes 1 through 22 for a human genome).

Divide all raw label coverage depths by the sum of non-sex-chromosomal (e.g. autosomal) raw label coverage depths. The result is the scaled label coverage depth profile (also referred to as a "scaled coverage depth profile"). The scaling can be done with respect to autosomal subset of labels (if applicable), rather than all labels, to avoid the variability associated with the gender-dependent copy number of sex chromosomes (if applicable; it is noted that methods and apparatuses in accordance with some embodiments herein are applicable to organisms that do not typically comprise sex TABLE 2-continued chromosomes). The purpose of the scaling is to enable comparison among various samples, characterized by different overall coverage levels.

Optionally, multiply the scaled label coverage profile by the number of autosomal labels. The multiplication elevates the scaled coverage depths to a convenient range comprising small integers.

Apply all the steps described above to multiple euploid samples. If the samples are mammalian (for example humans), apply the steps to multiple euploid samples of both genders. The resulting set of measurements constitutes the training set. Optionally, also generate a cross-validation set of measurements.

If applicable, for ChrX, the training set may consist only of female individuals. Optionally, the training set for ChrX may also include male individuals, but their ChrX scaled coverage depths would be adjusted to account for ChrX copy number in males. For example, the multiplier can be 2 in males with euploid ChrX copy number (karyotypes XY and XYY, Jacobs syndrome) and 1 in Klinefelter samples (karyotype XXY).

Optionally, if the sample comprises sex chromosomes, Sex Chromosome Normalization is performed as described herein.

If applicable, for ChrY, the training set comprises only male individuals.

If Jacobs syndrome (XYY) cases are present in the ChrY training set, an adjustment is preferably made to account for two copies of ChrY. In XYY samples, the ChrY scaled coverage depths can be multiplied by 0.5.

For all samples in the training set, evaluate sample-specific reciprocal characteristic molecule length values ($1/\lambda$). The values $1/\lambda$ will be used to define the abscissa x for the subsequent set of linear regressions, one regression per label.

Optionally, subtract the reciprocal median characteristic molecule length $1/\lambda_0$ from the term $1/\lambda$. The purpose of the subtraction is to center the range of the abscissa.

Optionally, multiply $1/\lambda$ (or the difference $1/\lambda-1/\lambda_0$) by a constant factor C. The purpose of the multiplication by a constant factor is to maintain a convenient range for the abscissa.

The resulting values $C(1/\lambda-1/\lambda_0)$ define the abscissa x.

For each label along the genome, perform linear regression of scaled label coverage depths vs. x.

The regression involves all the samples in the training set. The resulting gradient G and zero-order coefficient E are recorded and assigned to the current label. The parameters G and E will be used to perform copy number normalization on newly measured samples. Each label is assigned a separate pair of G, E values.

In addition to the gradient and the zero-order coefficient, also record the associated confidence measures (such as standard errors, p-values, confidence intervals, and relative error values). The relative error is defined as the sum of absolute deviations of predicted scaled coverage depths from the observed values, divided by the sum of scaled label coverage depths. The relative error is interpreted as the label-specific relative error.

Flag all labels whose relative errors exceed a predefined cutoff. The cutoff reflects the desired level of precision and is based on the overall coverage. As a rule of thumb, the expected error for a given coverage is obtained as the reciprocal square root of the coverage (assuming Poisson distribution). For example, 100x coverage is associated with ~10% relative error, white 36x coverage corresponds to 16% relative error.

Optionally, perform cross-validation of the label-specific parameters E and G on the cross-validation set of measurements.

For a newly collected data set, generate scaled label coverage depth profile as described above.

Generate the abscissa value $x = C(1/\lambda-1/\lambda_0)$ for the sample data set as described above. Use the scaled label coverage depths Q as an input to evaluate normalized label coverage depths n as follows: $n = Q/[E + GC(1/\lambda-1/\lambda_0)]$.

Multiply the resulting normalized label coverage depths n with chromosome-specific factors (2 for autosomes and X, 1 for Y) to generate copy-number profile.

Evaluate error in scaled coverage depths Q starting from the following equation:
Equation 2

$$Q = \frac{Mn}{N_0 + n} \tag{2}$$

where M is the number of autosomal labels, n is the raw coverage depth for a given label, and $N_0$ is the sum of raw coverage depths for all other autosomal labels.

The error in Q is estimated using truncated Taylor expansion, assuming independence of n and $N_0$:
Equation 3

$$(\delta Q)^2 = \left(\frac{\partial Q}{\partial n}\right)^2 (\delta n)^2 + \left(\frac{\partial Q}{\partial N_0}\right)^2 (\delta N_0)^2 \tag{3}$$

The partial derivatives in Equation 3 can be evaluated as shown:

$$\left(\frac{\partial Q}{\partial n}\right) = \frac{MN_0}{(N_0 + n)^2} \tag{4}$$

$$\left(\frac{\partial Q}{\partial N_0}\right) = \frac{-Mn}{(N_0 + n)^2} \tag{5}$$

TABLE 2-continued

An added assumption $N_0 \gg n$ simplifies the expressions for the derivatives. Also, the error propagation analysis assumes that both n and $N_0$ are distributed according to Poisson, with variances equal to the observed coverage depths. The error assessment for Q is therefore given by the following expression:

$$\delta Q = \sqrt{\frac{QM}{N_0 + n}} \tag{6}$$

The error propagation in normalized copy number values per label (L) is evaluated starting from the following expression:

$$L = \frac{Q}{E + GC\left(\frac{1}{\lambda} - \frac{1}{\lambda_0}\right)} \tag{7}$$

As with scaled coverage depths, the error propagation analysis uses perturbation (Taylor expansion up to the second order) and assumes independence among the possible sources of error (Q, E, G, and λ). The variance of copy numbers L is evaluated as follows:

$$(\delta L)^2 = \left(\frac{\partial L}{\partial Q}\right)^2 (\delta Q)^2 + \left(\frac{\partial L}{\partial E}\right)^2 (\delta E)^2 + \left(\frac{\partial L}{\partial G}\right)^2 (\delta G)^2 + \left(\frac{\partial L}{\partial \lambda}\right)^2 (\delta \lambda)^2 \tag{8}$$

It is noted that the errors evaluating using this approach can optionally be used to filter out labels associated with large fluctuations, and also can optionally be used as weights for numerical processing of copy number profiles, for example to detect features.
The partial derivatives involved in Eq. 7 are obtained straightforwardly:

$$\left(\frac{\partial L}{\partial Q}\right) = \frac{1}{E + GC\left(\frac{1}{\lambda} - \frac{1}{\lambda_0}\right)} \tag{9}$$

$$\left(\frac{\partial L}{\partial E}\right) = \frac{-Q}{\left[E + GC\left(\frac{1}{\lambda} - \frac{1}{\lambda_0}\right)\right]^2} \tag{10}$$

$$\left(\frac{\partial L}{\partial G}\right) = \frac{-QC\left(\frac{1}{\lambda} - \frac{1}{\lambda_0}\right)}{\left[E + GC\left(\frac{1}{\lambda} - \frac{1}{\lambda_0}\right)\right]^2} \tag{11}$$

$$\left(\frac{\partial L}{\partial \lambda}\right) = \frac{QC/\lambda^2}{\left[E + GC\left(\frac{1}{\lambda} - \frac{1}{\lambda_0}\right)\right]^2} \tag{12}$$

Error estimates for E, G, and λ are available as outputs of the linear regressions that produced these values. The error in Q is given by Eq. 6. By combining Eqs. 8-12, we are able to assess the sample-specific uncertainty of the copy number as a function of the genomic position. As a result, the confidence in copy number calls based on the normalized profile can be quantified using these error estimates.
Optionally, labels associated with larger than acceptable error bars may be filtered out for the purposes of analyses and/or visualization.
Optionally, errors such as errors evaluated using second-order Taylor expansion can be used in weights when doing numerical processing of copy number profiles, for example to detect features.
The initial implementation distinguishes between base error (including terms 10-12) and total errors (contribution from terms 9-12). The procedure filters out labels with base errors exceeding a preset cutoff. A typical cutoff value is 0.05.
An additional (optional) filtering removes labels with zero-order coefficient below a cutoff. A typical cutoff value is 0.7.

Unexpectedly, SIMONIDA can produce high precision of Chromosome Y coverage depth profiles, in spite of a small number of male training samples available and the known sequential similarity between Chromosome Y and the rest of the genome, in particular Chromosome X. Moreover, without being limited to any theory, SIMONIDA can produce higher precision than quantized copy number profile approaches such as GROM (see, e.g. FIG. 12 and Example 4), and further can provide a 5-7 fold increase in resolution in comparison to such quantized copy number profile approaches.

In some embodiments, SIMONIDA produces a SIMONIDA copy number profile. The SIMONIDA copy number profile can comprise a stepwise function taking values equal to integer multiples of one (starting from zero), with added noise. The relative error can range from 10% to 25% or more, depending on the total coverage, for example about 10% to 25%, about 10% to 35%, about 10% to 45%, about 15% to 25%, about 15% to 35%, about 15% to 45%, about 20% to 25%, about 20% to 35%, or about 20% to 45%. In some embodiments, p-values of $10^{-10}$ are used to identify significant changes in absolute copy numbers. The skilled artisan will appreciate a number of available approaches for calculating relative error, for example R factors and the like.

The techniques for elimination or minimization of bias, for example GROM or SIMONIDA, as described herein may be implemented on a computer processor in data communication with a detector configured to detect signals of labeled molecules linearized in fluidic channels as described herein. In some embodiments, a copy number profile of the sample molecules is generated by the processor. In some embodiments, the copy number profile is generated in real time. In some embodiments, the copy number profile is generated within about 10 minutes of detecting the signals of labeled molecules, for example within about 10, 9, 8, 7, 6, 5, 4, 3, 2, 1 minutes, or within about 50, 40, 30, 20, 10, 9, 8, 7, 6, 5, 4, 3, 2, 1, 0.5, 0.1, 0.05, 0.01, 0.001, or 0.0001 seconds, including ranges between any two of the listed values.

Sex Chromosome Normalization

It is noted that sex chromosomes can give rise to additional considerations. For example, due to a relatively lower number of chromosome Y (ChrYs) or chromosome X (ChrXs) in a population (as compared to autosomes), measurements of sex chromosomes can include relatively large numbers of outliers. For example, similarities between portions of chromosome X and chromosome Y can give rise to a possibility that labeled molecules from ChrY will be categorized as labeled molecules from ChrX and vice versa. As such, for female samples, there is a possibility that unless additional adjustments are made, an atypical ChrX that comprises portions of ChrY will be categorized as ChrX only. Accordingly, in some embodiments, for sex-chromosome-derived sample molecules, Sex Chromosome Normalization as described herein is performed. Sex Chromosome Normalization can be performed, for example, in conjunction with SIMONIDA or Normalization by Number of Labels.

In some embodiments, SIMONIDA (or Normalization by Number of Labels) is performed as described herein, for example as in Table 2, or in FIG. 44, and further comprises Sex Chromosome Normalization. Sex Chromosome Normalization can involve obtaining a scaled coverage depth profile by SIMONIDA (or Normalization by Number of Labels) as described herein, and applying additional analytics and/or transformations.

Figure 45:
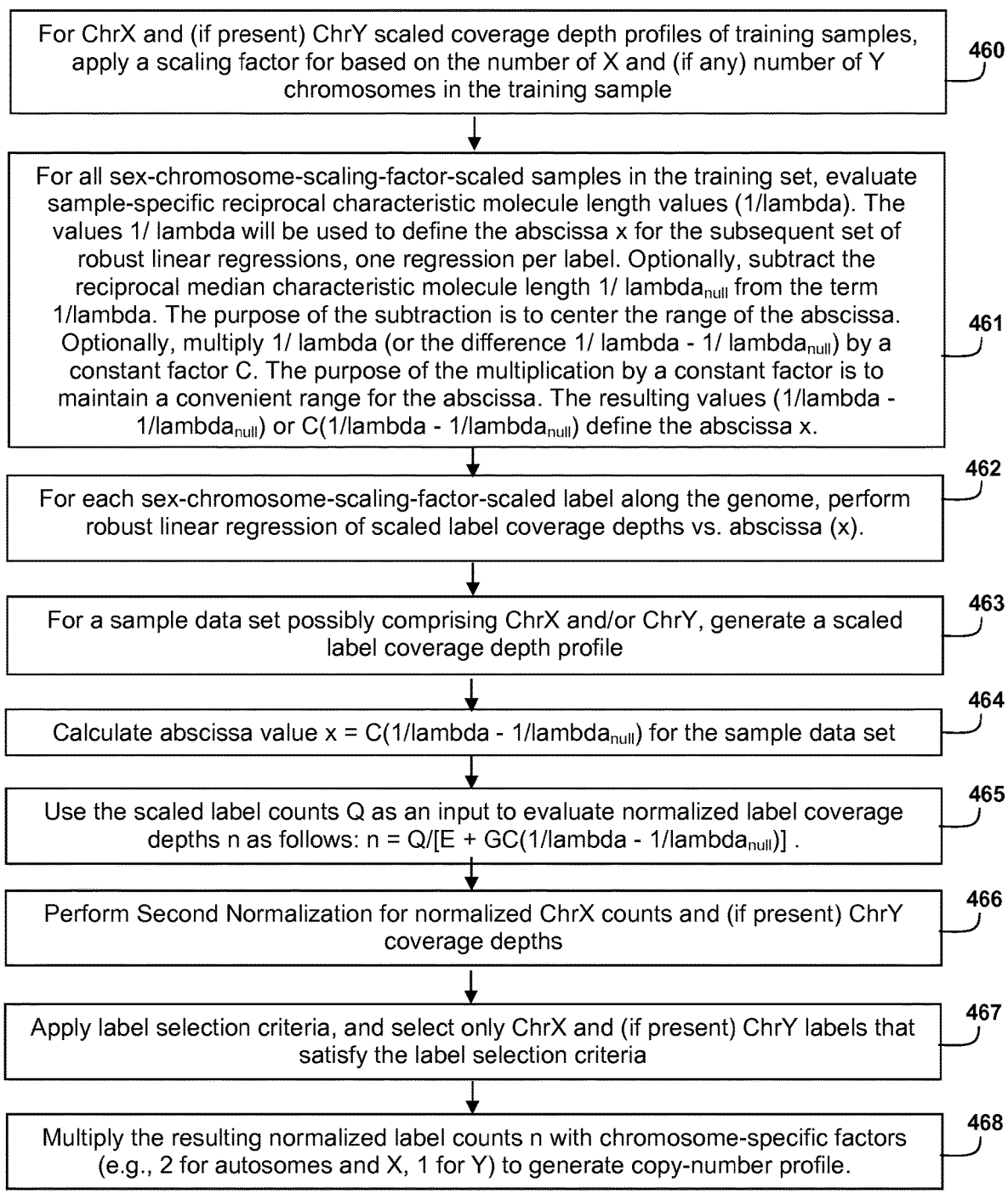
FIG. 45 is a flow diagram illustrating methods for minimizing or eliminating bias comprising normalized copy number per label and comprising Sex Chromosome Normalization in accordance with some embodiments herein.

FIG. 45 is a flow diagram illustrating Sex Chromosome Normalization in accordance with some embodiments herein, which can be performed in conjunction with SIMONIDA (or Normalization by Number of Labels) in accordance with some embodiments herein. For ChrX and (if present) ChrY scaled coverage depth profiles of training samples, a scaling factor based on the number of ChrX and (if any) number of ChrY in the training sample can be applied in 460. It is noted that the scaled coverage depth profile can be obtained in accordance with SIMONIDA in accordance with some embodiments herein (see, e.g. Table 2 and/or FIG. 44). For all sex-chromosome-scaling-factor-scaled samples in the training set, sample-specific reciprocal characteristic molecule length values (1/lambda) can be evaluated. The values 1/lambda can be used to define the abscissa x for the subsequent set of robust linear regressions, one regression per label. Optionally, the reciprocal median characteristic molecule length $1/\text{lambda}_{null}$ can be subtracted from the term 1/lambda. The purpose of the subtraction is to center the range of the abscissa. Optionally, 1/lambda (or the difference $1/\text{lambda}-1/\text{lambda}_{null}$) can be multiplied by a constant factor C. The purpose of the multiplication by a constant factor is to maintain a convenient range for the abscissa. The resulting values ($1/\text{lambda}-1/\text{lambda}_{null}$) or $C(1/\text{lambda}-1/\text{lambda}_{null})$ define the abscissa x in 461. For each sex-chromosome-scaling-factor-scaled label along the genome, robust linear regression of scaled label coverage depths vs. abscissa (x) can be performed in 462. For a sample data set possibly comprising ChrX and/or ChrY (e.g. a newly obtained data set), a scaled label coverage depth profile can be generated in 463. Abscissa value $x=C(1/\text{lambda}-1/\text{lambda}_{null})$ can be calculated for the sample data set in 464. The scaled label coverage depths Q can be used as an input to evaluate normalized label coverage depths n as follows: $n=Q/[E+GC(1/\text{lambda}-1/\text{lambda}_{null})]$ in 465. Second Normalization can be performed for normalized ChrX coverage depths and (if present) ChrY coverage depths in 466. Label selection criteria can be applied, and can select only ChrX and (if present) ChrY labels that satisfy the label selection criteria in 467. The resulting normalized label coverage depths n can be multiplied with chromosome-specific factors (e.g., 2 for autosomes and X, 1 for Y) to generate copy-number profile in 468. The skilled artisan will appreciate that steps listed herein can be performed in a different order, eliminated, or duplicated in accordance with some embodiments:

For training sets in Sex Chromosome Normalization, for each sample in a training set, two numbers can be assigned: (E) the number of ChrX (e.g. 1, 2, or in the case of trisomy-X, 3), and (II) the number of Y chromosomes (e.g. 0, 1, or, in the case of Jacobs syndrome, 2). For each sample, the scaled label coverage depths be adjusted to account for the number of X (and if present, Y) chromosomes.

For chromosome X labels in the training set in Sex Chromosome Normalization, the scaled chromosome X coverage depths can be adjusted by a scaling factor derived from the number of X chromosomes in the sample. Optionally, the scaling factor comprises: dividing by the number of X chromosomes minus 1 (for example, if there are 2 X chromosomes, the scale factor would involve dividing by 1). It is noted that that a scaling factor of dividing by "number of X chromosomes minus 1" would involve dividing by 0 for Turner females and XY and XYY males with 1 X chromosome; accordingly, for this scaling factor, XXY males could be used in the training set. Optionally, the scaling factor comprises: multiplying male X chromosome coverage depths by a weighing factor of 2 for linear regression, and dividing Turner female and male X chromosome coverage depths by the square root of 2 after linear regression, so as to limit any impact of multiplying the male X chromosomes coverage depths by the weighing factor.

For chromosome Y labels in the training set in Sex Chromosome Normalization, the scaled chromosome Y coverage depths can be divided by a scaling factor derived from the number of Y chromosomes in the sample. The Y chromosome scaling factor can comprise dividing scaled chromosome Y coverage depths by the number of Y chromosomes in the sample. It is noted that for cuploid and XXY male samples, this scaling factor would involve dividing scaled chromosome Y coverage depths by 1. It is noted that in Jacobs (XYY) male samples this scaling factor would involve dividing scaled chromosome Y coverage depths by 2. It is noted that for female samples, the scaling factor would involve dividing by 0, and so the female samples would be excluded from the training set.

For chromosome X labels in the training set and chromosome Y labels in the training set, it is contemplated that there can be more outliers than in a typical autosomal training set. Accordingly, for the chromosome X and chromosome Y labels in the training set in Sex Chromosome, a robust linear regression (rather than regular linear regression) can be applied. It has been observed that if robust linear regression is applied to the X and Y chromosome labels, the effects of outliers are minimized. It is noted, however, that in accordance with some embodiments herein, regular linear regression is suitable for autosomes.

For chromosome X labels for Sex Chromosome Normalization, error propagation can be estimated by similar approaches as those described for autosomes herein (e.g. by Taylor expansion as described in Table 2).

For chromosome Y labels for Sex Chromosome Normalization, a robust measure of error propagation can be useful. Accordingly, error propagation can be calculated based on median absolute deviation (MAD). It is contemplated that chromosome Y labels that have a median for male samples that is substantially greater than the median for female samples (relative to combined MAD values for males and females) can represent robust measures of the Y chromosome. Accordingly, in some embodiments, Y chromosome labels are selected from labels that have a median for male samples that is at least 0.5 higher than the median for female samples, for example, 0.5 higher, 0.7, 0.9, 1, 1.1, 1.2, 1.3, 1.5, 1.9, 2, 2.5, 3, 4, 5, 6, 7, 8, 9, or 10 higher, including ranges between any two of the listed values.

It is contemplated that labels having an zero-order coefficient greater than 0.3 are more likely to be robust. Accordingly, in some embodiments, labels having an zero-order coefficient of at least 0.3 are selected, for example, at least 0.3, 0.4, 0.5, 0.6, 0.7, 0.8, 0.9, 1.0, 1.2, 1.5, 2, 2.5, 3, 3.5, 4, 4.5, 5, 5.5, 6, 6.5, 7, 7.5, 8, 8.5, 9, 9.5, or 10, including ranges between any two of the listed values.

Figure 47A:
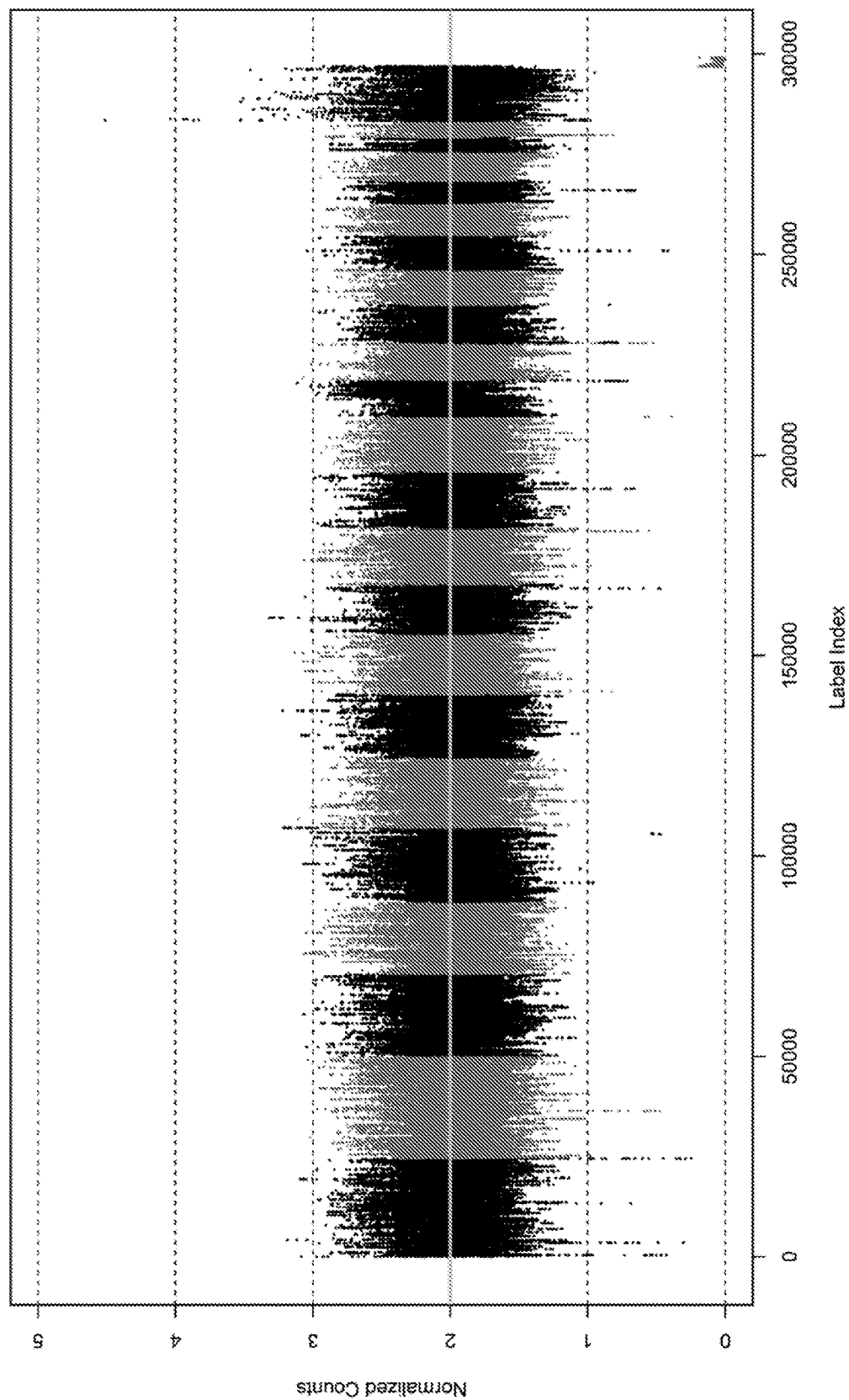
FIG. 47A is a graph illustrating an example of a copy number profile per label for a NA12878 (female) cell line cell as determined using SIMONIDA and comprising Sex Chromosome Normalization in accordance with some embodiments herein.

Sex Chromosome Normalization can further comprise normalizing X chromosome and Y chromosome coverage depth profiles for a data set collected from a sample (e.g. a newly collected data set) in view of the analysis of the training set. For the sample data set, a normalized SIMONIDA copy profile can be obtained (e.g., as in Table 2 and/or FIG. 44). It has been observed, however, that for normalized SIMONIDA copy profiles in the absence of Secondary Normalization, there is substantial correlation between normalized ChrX coverage depths from sample-to-sample, and between normalized ChrY coverage depths from sample-to-sample, suggesting that some bias remains. Accordingly, for Sex Chromosome Normalization in accordance with some embodiments herein, a "Second Normalization", as described below, is performed for SIMONIDA-normalized ChrX and ChrY coverage depth profiles:

The Second Normalization can further reduce or eliminate bias for ChrX and (if present) ChrY coverage depth profiles. Optionally, if ChrXs are to be evaluated, the Second Normalization can comprise calculating the median value and the MAD for a plurality of normalized ChrX coverage depths for a plurality of female samples (it is noted that larger number of samples can be useful, and as such, the median value and MAD can be calculated for the normalized ChrX coverage depths for all of the female samples in the training sample). Optionally, if ChrYs are to be evaluated, the Second Normalization can comprise calculating the median value and the MAD for a plurality of normalized ChrY coverage depths for a plurality of male samples (it is noted that larger number of samples can be useful, and as such, the median value and MAD can be calculated for the normalized ChrY coverage depths for all of the male samples in the training sample). The Second Normalization can comprise dividing ChrX normalized values by the median value across a plurality of female samples (e.g. all female training samples) for the chromosome (X). Furthermore, the Second Normalization can comprise dividing ChrY normalized values by the median value across a plurality of male samples (e.g. all male training samples) for ChrY, and dividing this value by 2 (i.e. dividing ChrY normalized values by 2 times the median value across a plurality of sample for ChrY). It has been noted that the standard deviations are substantially reduced if a second normalization is performed on X- and Y-chromosome coverage depth profiles, as compared to if only the initial normalization is performed (see FIGS. 47A-B).

Optionally, label selection criteria can be applied to ChrX and ChrY labels, and only labels that satisfy the label selection criteria are used for the copy number profile. It is contemplated that applying label selection criteria can further improve the robustness and accuracy of ChrX and ChrY copy number profiles of Sex Chromosome Normalization in accordance with some embodiments herein. Without being limited by any theory, it is noted that samples prepared from shorter molecules are generally likely to have more error, and as such, label selection criteria in accordance with some embodiments herein can be useful for relatively short sample molecules.

Optionally, label selection criteria can be applied to ChrX labels, so that only ChrX labels that satisfy all four of the following criteria are used in the copy number profile: (1) the ratio of (base error for a given label in a given sample)/(zero-order coefficient for the label) is less than the 95% quantile for base error for all ChrX labels in the given sample, for example less than the 95%, 93%, 90%, 85%, 80%, 75%, or 70% quantile for base error; (2) the zero-order coefficient for a given label exceeds at least 0.7, for example exceeding 0.7, 0.8, 0.9, 0.95, or 0.99; (3) a median normalized coverage depth for a label across samples from a second normalization exceeds 0.6, for example exceeding 0.6, 0.7, 0.8, 0.9, 0.95, or 0.99; and (4) the MAD for the label is less than 0.5, for example, less than 0.5, 0.4, 0.4, 0.2, 0.1, 0.05, or 0.01. In some embodiments, heuristically-determined label selection criteria, which can differ numerically from the indicated label selection criteria (1)-(4) are applied.

Optionally, label selection criteria can be applied to ChrY labels, so that only ChrY labels that satisfy all five of the following criteria are used in the copy number profile: (1) the median for the label within males exceeds the median value for the label for females by at least 1 MAD (i.e. the median for the label within males is at least 1 MAD away from the MAD for the label for females), for example at least 1, 1.2, 1.5, 2, 2.5, 3, 4, or 5 MADs; (2) the ratio of (base error for a given label in a given sample)/(zero-order coefficient for the label) is less than the 95% quantile for base error for all ChrY labels in the given sample, for example less than the 95%, 93%, 90%, 85%, 80%, 75%, or 70% quantile for base error; (3) the zero-order coefficient for a given label exceeds at least 0.7, for example exceeding 0.7, 0.8, 0.9, 0.95, or 0.99; (4) a median normalized coverage depth for a label across samples from a second normalization exceeds 0.4, for example exceeding 0.4, 0.5, 0.6, 0.7, 0.8, 0.9, 0.95, or 0.99; and (5) the median absolute deviation (MAD) for a given label for ChrY is less than 1, for example less than 1, 0.95, 0.9, 0.8, 0.7, 0.5, 0.4, or 0.3. It has been observed that a combination of robust linear regression and selecting labels for which a MAD is less than 1 in accordance with some embodiments herein can exclude portions ChrY (e.g. portions of ChrY recombined or translocate onto ChrX) from an ChrX copy number profile. Furthermore, it has been observed that even after portions of ChrY have been excluded from the an ChrX copy number profile in accordance with some embodiments herein, ChrX chromosomes comprising portions of a ChrY can be identified using the normalized coverage depths profiles. In some embodiments, heuristically-determined label selection criteria, which can differ numerically from the indicated label selection criteria (1)-(5) are applied.

While the above examples and description of Sex Chromosome Normalization refer to chromosome X and Y in males and females, for example as in mammalian sex determination, it is also contemplated that Sex Chromosome Normalization is readily applicable to a variety of organisms that use a variety different systems of sex determination (e.g. "ZW" sex determination, which is used, for example by some birds, or "XO" sex determination, which is used, for example, by some insects and nematodes). As such, Sex Chromosome Normalization as used herein is not limited to analysis of genomes of organisms that use "XY" sex determination.

Normalization by Number of Labels

In accordance with some embodiments herein, bias is minimized or eliminated using Normalization by Number of Labels. It is contemplated that SIMONIDA as described herein can be modified so that the normalization is performed based on the number of labels per molecule, or based on the number of labels within a segment of predetermined length within each molecule. As such, in some embodiments, normalization is performed based on the characteristic number of labels per molecule or within a segment of predetermined length ("Normalization by Number of Labels"). A "predetermined length" refers to a quantity of material in the sample molecules (e.g. quantity of bases in a nucleic acid molecule) that is established as of the time of the normalization, so that the predetermined length will be consistent from sample molecule-to-sample molecule. If the normalization is based on the number of labels within a segment of predetermined length, optionally, the predetermined length can be about 10 kb, 20 kb, 30 kb, 40 kb, 50 kb, 60 kb, 70 kb, 80 kb, 90 kb, 100 kb, 150 kb, 200 kb, 250 kb, 300 kb, 350 kb, 400 kb, 450 kb, 500 kb, 550 kb, 550 kb, 600 kb, 650 kb, 700 kb, 750 kb, 800 kb, 850 kb, 900 kb, 950 kb, 1 Mb, 1.5 Mb, or 2 Mb, including ranges between any of the listed values, for example 10 kb-1 Mb, 10 kb-500 kb, 10 kb-300 kb, 10 kb-200 kb, 10 kb-100 kb, 50 kb-1 Mb, 50 kb-500 kb, 50 kb-300 kb, 50 kb-200 kb, 50 kb-100 kb, 70 kB-1 MB, 70 kb-500 kb, 70 kb-300 kb, 70 kb-200 kb, 70 kb-100 kb, 100 kb-1 Mb, 100 kb-500 kb, 100 kb-300 kb, 100 kb-200 kb. Optionally, the predetermined length can be a least about 10 kb, for example at least 10 kb, 20 kb, 30 kb, 40 kb, 50 kb, 60 kb, 70 kb, 80 kb, 90 kb, 100 kb, 150 kb, 200 kb, 250 kb, 300 kb, 350 kb, 400 kb, 450 kb, 500 kb, 550 kb, 550 kb, 600 kb, 650 kb, 700 kb, 750 kb, 800 kb, 850 kb, 900 kb, 950 kb, 1 Mb, 1.5 Mb, or 2 Mb. It is contemplated that Normalization by Number of Labels can utilize the approaches of SIMONIDA as described herein (for example, in FIG. 44 and/or Table 2), except that rather than molecule length (lambda), a descriptor based on the distribution of number of labels is used, for example a distribution of number of labels per molecule, or a distribution of number or labels within a segment of predetermined length within each molecule. Accordingly, it is contemplated that any embodiments herein comprising SIMONIDA can be adjusted to involve a Normalization by Number of Labels approach.

In some embodiments, Normalization by Number of Labels further comprises Sex Chromosome Normalization as described herein (as adjusted for Normalization by Number of Labels in lieu of SIMONIDA).

In some embodiments, Normalization by Number of Labels eliminates bias caused by label density, and bias introduced by factors other than label density. In some embodiments. Normalization by Number of Labels eliminates bias caused by label density. In some embodiments, Normalization by Number of Labels eliminates bias introduced by factors other than label density. In some embodiments, Normalization by Number of Labels minimizes bias caused by label density, and bias introduced by factors other than label density. In some embodiments, Normalization by Number of Labels minimizes caused by label density. In some embodiments, Normalization by Number of Labels minimizes bias introduced by factors other than label density. In some embodiments, Normalization by Number of Labels eliminates bias caused by label density and minimizes bias introduced by factors other than label density. In some embodiments, Normalization by Number of Labels minimizes bias caused by label density and eliminates bias introduced by factors other than label density.

Detection of Aneuploidy and Structural Variation

Aneuploidy is associated with numerous disease states, for example cancers and various developmental disorders. Types of aneuploidy can include hyperpolyploidy (for example, trisomy) and hypopolyploidy (for example, monosomy). In some embodiments, aneuploidy is detected in a sample. A possibly aneuploid sample can be compared to a normal or euploid sample. In some embodiments, the normal or euploid sample is from the same organism as the possibly aneuploidy sample. In some embodiments, the normal or euploid sample is from a different organism. In some embodiments, patterns characteristic of a normal or euploid sample are stored as electronic or optical values for comparison to the possibly aneuploidy sample. In some embodiments, the aneuploidy is detected automatically. In some embodiments, the aneuploidy is detected based on a GROM or SIMONIDA copy number profile as described herein.

In addition to aneuploidy, regional genomic structural variation (SV) can be associated with various disease states. Exemplary SV includes duplications, deletions, and complex rearrangements such as translocations. In some embodiments, the structural variation is detected automatically. In some embodiments, detection of complex genomic rearrangements is automated by identifying abrupt changes in copy number profiles and focusing on the consensus genomic maps and/or single molecules that map to the reference region surrounding or overlapping with the copy number breakpoints. This procedure can substantially reduce the number of false positive calls, increasing the accuracy and reliability of structural variation detection. Accordingly, in some embodiments large-scale duplications, deletions, and complex genomic rearrangements (such as translocations) are accurately identified. In some embodiments, large-scale deletions, deletions, and complex rearrangements are accurately identified automatically.

In some embodiments, a copy number profile (e.g. GROM or SIMONIDA) is used to identify breakpoints. The GROM or SIMONIDA copy number profile of a sample can be obtained as described herein. An algorithm can be applied to identify breakpoints in the GROM or SIMONIDA copy number profile. There are a number of algorithms suitable for identifying the breakpoints, including, but not limited to the Hidden Markov Model (HMM), circular binary segmentation (CBS), and Rank Segmentation. In some embodiments, a p-value based edge detection algorithm is used to identify breakpoints. The p-value based edge detection algorithm can identify significant changes in GROM or SIMO-NIDA copy number, which the skilled artisan will appreciate can represent aneuploidy (for example if the GROM or SIMONIDA copy number for a chromosome is significantly different than the copy number of a reference chromosome). The statistical analysis can account, as appropriate, for normal copy numbers of sex chromosomes, such as a single X and a single Y chromosome in males. Optionally, the GROM and/or SIMONIDA breakpoints are determined automatically.

As described herein, providing a GROM copy number can comprise apportioning a reference genome (or portion of a genome) is divided into a plurality of intervals. The p-value based edge algorithm can traverse all intervals and assign a p value to each interval. As such, the p-value based edge algorithm can identify intervals that have a significantly higher or lower GROM copy number than neighboring intervals, thus identifying intervals that are likely to represent breakpoints of a structural variation. The p-value can be evaluated by selecting a sample size N and comparing the set of N intervals to the right from the current interval to the set of N intervals to the left of the current interval. The comparison can be done using t-test or nonparametric Wilcoxon (Mann-Whitney) U test. The p-value that results from the test is assigned to the current interval. Edges of a chromosome can be handled by appropriately adjusting the sample size N. Significant changes can be detected by identifying all intervals with a p-value that satisfies a threshold. In some embodiments, significant changes in copy number profile are detected by selecting all intervals with negative logarithm (base 10) of the p-value exceeding a preset cutoff. In some embodiments, the cutoff is 10. It is disclosed herein that aneuploidy, and SVs including breakpoints of deletions, and translocations can be reliably detected using a cutoff of 10. In some embodiments, for example if greater stringency is desired, the cutoff is set higher than 10 (that is, requiring a negative $\log_{10}$ p value of greater than at least 10; see, e.g. Example 3), for example greater than 10, 20, 30, 40, 50, 60, 70, 80, 90, 100, 200, 300, 400, 500, 600, 700, 800, 900, 1,000, 5,000, or 10,000. In some embodiments, for example if relatively lower stringency is desired, the cutoff is set higher than 1.3 (that is, requiring a negative $\log_{10}$ p value of greater than at least 1.3), for example greater than 1.3, 1.4, 1.5, 2, 3, 4, 5, 6, 7, 8, 9, or 10. Optionally, the comparison can be performed automatically. Additionally, in some embodiments an SIMONIDA copy number can further be calculated for the same sample. A hybrid approach involving (and/or comparing) both SIMONIDA and GROM copy number can be performed. As such, it is contemplated that in accordance with some embodiments herein, an SIMONIDA copy number can be calculated, and compared for neighboring genomic labels, and SIMONIDA copy number for the labels can be compared, for example to identify possible genomic structural features based on an SIMONIDA copy number for a sample, and/or to compare to GROM copy number and/or possible genomic structural features based on a GROM copy number.

In some embodiments, an autosome (or copy-number adjusted sex chromosome) with a significantly different GROM or SIMONIDA copy number than other autosomes is determined to be aneuploid. Based on whether copy number is elevated or reduced, the autosome or sex chromosome can be determined to be hyperpolyploid or hypopolyploid. In a diploid organism, an autosome present in only a single copy can be determined to be hypopolyploid (monoploid). In a diploid organism, an autosome present in a copy number of three or more can be determined to be hyperpolyploid. In some embodiments, an interval having a significantly different copy number can be determined to be a breakpoint (or a possible breakpoint) for a SV. In some embodiments, the possible breakpoint is further analyzed and confirmed through analysis of polynucleotides spanning the possible breakpoint, and/or through confirmation via a second algorithm for determining SV. Optionally, the determination of aneuploidy is made automatically.

In some embodiments, GROM or SIMONIDA uses copy number values generated by the RefAligner software. These values can be stored on a computer readable medium, for example in the Coverage filed of at least one input CMPA file. The RefAligner program can be used to identify possible structural variations, for example breakpoints of a deletion, duplication, or translocation. In RefAligner, molecule maps are generated from the complete set of sample molecules that align with the contig. This larger set of maps is used to repeat the maximum likelihood optimization of each contig map. In addition the coverage of maps for each contig is analyzed to find lower coverage regions that may indicate that the contig is incorrectly joining two regions of the genome. If so, the contig is broken apart at the low coverage point.

In some embodiments, SIMONIDA copy number values are coupled with a second algorithm to identify possible SV, such as breakpoints of genetic abnormalities. SIMONIDA copy number values that represent possible breakpoints, and that align with possible structural variation identified by the second algorithm have a high likelihood of representing bona fide SVs. In some embodiments, GROM copy number values are coupled with a second algorithm to identify possible SV, such as breakpoints of genetic abnormalities. GROM copy number values that represent possible breakpoints, and that align with possible structural variation identified by the second algorithm have a high likelihood of representing bona fide SVs.

In some embodiments, GROM copy number breakpoints are compared to SIMONIDA copy number breakpoints. As GROM/SIMONIDA breakpoints can represent possible translocations, optionally, pairs of GROM/SIMONIDA breakpoints that combine the same consensus map with multiple genomic locations can be identified. The confidence of the subset of SIMONIDA breakpoints that overlap with GROM breakpoints can be assessed. A number of procedures may be used to assess the confidence, for example, alignment of the flanking genomic regions in the reference, comparison with unaffected genomic regions, and/or analyses of interlabel distance distributions.

In some embodiments, GROM or SIMONIDA is coupled with Recursive Pair-Split Alignment (RPSA). RPCS can be used to compare at least one assembled contig to a reference, for example a reference genome. Automated structural variant calls based on RPSA that overlap with breakpoints in the GROM or SIMONIDA copy number profile can be identified. As GROM or SIMONIDA/RPSA breakpoints can represent possible translocations, optionally, pairs of GROM or SIMONIDA/RPSA breakpoints that combine the same consensus map with multiple genomic locations can be identified. The confidence of the subset of RPSA calls that overlap with GROM or SIMONIDA breakpoints can be assessed. A number of procedures may be used to assess the confidence, for example, alignment of the flanking genomic regions in the reference, comparison with unaffected genomic regions, and/or analyses of interlabel distance distributions.

In some embodiments, GROM or SIMONIDA is coupled with an RPSA analysis as follows: An RPSA complex SV call is made, in which the SV call comprises two breakpoints. For each of the RPSA SV breakpoints, the p-values from GROM or SIMONIDA copy number profile changes are evaluated. If both GROM or SIMONIDA p-values are significant, the RPSA SV breakpoint calls are considered to be reliable (e.g. each breakpoint for a possible SV as predicted by RPSA is confirmed by GROM or SIMONIDA). In some embodiments, the significance of the p-values is determined as follows: the standard deviation of the negative logarithm of p values throughout the genome (or the chromosome) is evaluated. If a given $-\log_{10}(p)$ is greater than three (3) standard deviations (SD's), the p-values are determined to be significant. In some embodiments, if greater stringency is desired, the $-\log_{10}(p)$ threshold is set higher than three (3) standard deviations (SD's), for example at least about 4, 5, 6, 7, 8, 9, or 10. In some embodiments, if lower stringency is desired, the $-\log_{10}(p)$ threshold is set at about 1.5, 2, or 2.5 standard deviations.

In some embodiments, GROM or SIMONIDA is coupled with an alignment of single molecules directly to the reference. This procedure can identify a breakpoint in the GROM or SIMONIDA copy number profile, split the reference at that point, mask one side of the divide, and score only those single molecule alignments that match molecular labels with the reference labels on the opposite side of the divide. The masked alignment of single molecules can be followed by clustering of the aligned molecules with respect to the masked region and a follow-up alignment of each cluster to the entire genome. The second alignment can identify genomic locations involved in complex rearrangement events, for example translocations.

The techniques for elimination or minimization of bias, for example GROM or SIMONIDA, and/or automated detection of structural variants as described herein may be implemented in hardware, software, firmware, or combinations thereof. If implemented in software, the techniques may be realized at least in part by a computer-readable medium comprising instructions that, when executed, performs one or more of the methods described above. The computer-readable medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates code in the form of instructions or data structures and that can be accessed, read, and/or executed by a computer.

Sample Molecules

In some embodiments, methods are provided herein in which the methods are sensitive enough to detect "short" fragments that are on the order of tens to hundreds of nucleotides in length. In some embodiments, the sample molecules as described herein comprise polynucleotide "short" fragments of about 2000 bp or less. For example, in some embodiments, the polynucleotide fragments are about 10, 15, 20, 25, 30, 35, 40, 45, 50, 55, 60, 65, 70, 75, 80, 85, 90, 95, or 100 nucleotides in length, including ranges between any two of the listed values. In some embodiments, the sample comprises sample molecules comprising polynucleotide fragments are about 10, 15, 20, 25, 30, 35, 40, 45, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, or 2000 nucleotides in length, including ranges between any two of the listed values, for example 10-2000 nucleotides, 10-1000, 10-700, 10-500, 10-300, 20-2000, 20-1000, 20-700, 20-500, 20-300, 50-2000, 50-1000, 50-700, 50-500, 50-300, 75-2000, 75-1000, 75-700, 75-500, 75-300, 100-2000, 100-1000, 100-700, 100-500, 100-300, 200-2000, 200-1000, 200-700, 200-500, 200-300, 300-2000, 300-1000, 300-700, 300-500, 500-2000, 500-1000, or 500-700 nucleotides. In some embodiments, the molecules of interest are fragments of less than about 1000, 950, 900, 850, 800, 750, 700, 650, 600, 550, 500, 450, 400, 350, 300, 250, 200, 150, 100, or 50 nucleotides in length. In some embodiments, the fragments are double-stranded. In some embodiments, the fragments comprise DNA. In some embodiments, the fragments comprise RNA. In some embodiments, the fragments comprise DNA hybridized to RNA. In some embodiments, the sensitivity is about as high as detecting a single fluorophore associated with a target fragment.

In some embodiments, the nucleotides of interest are fragments of at least about 500 nucleotides in length, for example about 500, 600, 700, 800, 900, 1000, 1100, 1200, 1300, 1400, 1500, 1600, 1700, 1800, 1900, or 2000 nucleotides in length, including ranges between any two of the listed values, for example about 500 to about 2000 nucleotides in length, about 500 to about 1500, about 500 to about 1000, about 500 to about 900, about 500 to about 700, about 700 to about 2000, about 700 to about 1500, about 700 to about 1000, about 700 to about 900, about 1000 to about 2000, about 1000 to about 1500, or about 1500 to about 2000.

Molecules suitable for use in the methods and systems described herein include polymers, double-stranded DNA, single-stranded DNA, RNA, DNA-RNA hybrids, polypeptides, biological molecules, proteins, and the like. Suitable polymers include homopolymers, copolymers, block copolymers, random copolymers, branched copolymers, dendrimers, or any combination thereof.

In some embodiments, the methods described herein are sensitive enough to detect a fetal molecule that constitutes less than about 0.025%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 6%, 7%, 8%, 9%, 10%, 11%, 12%, 13%, 14%, 15%, 20%, or 25% of the total number of molecules in a maternal blood sample.

Labels and Labeling

Labeling as used herein can comprise labeling of sequences or non-sequence features such as epigenetic features or patterns. In some embodiments, labeling is directed to a sequence motif or chemical moiety. Labeling can be carried out using any technique known to one of skill in the art, including chemical or biochemical conjugation. In some embodiments, the labels described herein are bound to a unique sequence motif. In some embodiments, the labels described herein are bound to a chemical moiety. In some of these embodiments, the chemical moiety is related to a specific chromosome. In some embodiments, labels of a particular labeling density are used. In some embodiments, a label density of about 1 to 50 labels per 100 kb is selected, more preferably about 5 to 35 labels per 100 kb. In some embodiments a label density of about 1 label per 100 kb, 2, 3, 4, 5, 6, 7, 8, 9, 10, 15, 20, 25, 30, 35, 40, 45, or 50 labels per 100 kb is selected, including ranges between any two of the listed values. As discussed herein, some label densities under some conditions are a potential source of bias. As such, in some embodiments herein, biases resulting from label density are minimized or eliminated through SIMONIDA or GROM.

In some embodiments herein, each label is independently selected from the group consisting of a fluorophore, a quantum dot, a dendrimer, a nanowire, a bead, a hapten, a streptavidin, an avidin, a neutravidin, a biotin, and a reactive group. In some embodiments herein, the first and second labels are independently selected from the group consisting of a fluorophore or a quantum dot. In some embodiments herein, at least one of the labels comprises a non-optical label. In some embodiments herein, the labeling is carried out with a polymerase. In some embodiments herein, the labeling is carried out with a polymerase in the presence of dNTPs comprising the label. In some embodiments herein, the polymerase has a 5' to 3' exonuclease activity. In some embodiments herein, the polymerase leaves a flap region, and wherein the flap region is removed to restore a ligatable nick prior to the repairing with a ligase. In some embodiments herein, the flap region is removed using the 5' to 3' exonuclease activity of a polymerase under conditions wherein at least one nucleotide is present in limited concentration. In some embodiments herein, the flap region is removed using the 5' to 3' exonuclease activity of a polymerase under conditions wherein at least one nucleotide is omitted from the reaction. In some embodiments herein, the flap region is removed with a flap endonuclease. In some embodiments herein, the labeling is carried out with a polymerase in the presence of at least one species of dNTP. In some embodiments herein, the at least one species of dNTP is a single species of dNTP. In some embodiments herein, a method as described herein further comprises modulating activity of the polymerase by adjusting the temperature, dNTP concentration, cofactor concentration, buffer concentration, or any combination thereof, during labeling. In some embodiments herein, nicking the first motif or the second motif comprising nicking with Nt.B-spQI. In some embodiments herein, the a non-sequence-specific label, for example a polynucleotide backbone label is applied in addition to a sequence-specific label or labels as described herein.

In some embodiments, at least one label as described herein comprises a non-optical label. A variety of non-optical labels can be used in conjunction with embodiments herein. In some embodiments a non-optical label comprises an electronic label. Exemplary electronic labels include, but are not limited to molecule with a strong electric charge, for example ions such as a metal ions, charged amino acid side chain, or other cations or anions. An electronic label can be detected, for example, by conductivity (or resistivity) when the label is disposed in a detector. In some embodiments, a nanochannel comprises an electrode configured to determine the presence or absence of an electronic label by determining the conductivity or resistivity of a substance disposed in the channel. In some embodiments, the non-optical label comprises a metal, metal oxide (for example metal oxide), or silicon oxide moiety. In some embodiments, the non-optical label comprises a moiety (for example a nanoparticle) comprising a metal, metal oxide, or other oxide. The presence of a particular metal or oxide moiety can be detected, for example by nuclear magnetic resonance. In some embodiments, the label is configured to release a moiety, for example a proton or an anion, upon a certain condition (e.g. change of pH) and the presence or absence of released moiety is detected.

In some embodiments, the sample is labeled with two or more labels, which are different from each other. In some embodiments, the sample is labeled, with at least two, three, four, five, six, seven, eight, nine, or ten labels, each of which are different from each other. Optionally, two or more motifs can be labeled with the same label. Optionally, two or more motifs can be labeled with the same label, while other motifs are labeled with different labels. For example, a first motif can be labeled with a first label so as to generate a first unique pattern, and a second motif that is different from the first motif can be labeled with a second label different from the first label so as to generate a second unique pattern. In some embodiments, two or more labels are the same. For example, a first motif can be labeled with a label, and a second motif that is different from the first motif can also be labeled with the same label so as to generate a unique pattern. In some embodiments, a plurality of probes corresponding to a first chromosome or region of interest are labeled with a first label, and a second plurality of probes corresponding to a second chromosome or region of interest (for example a reference chromosome or region) are labeled with a second label that is different than the first label. As such, labeled sample molecules comprising sequences from the first chromosome or region of interest can be differentiated from sample molecules comprising sequences from the second chromosome or region of interest based on whether they are labeled with the first label or second label.

Nucleotides with reversible terminators can form a first phosphodiester linkage, but prior to reversal of termination, cannot form (or have limited capacity to form) a second phosphodiester linkage. Thus, a nucleotide with a reversible terminator can be incorporated into a polynucleotide (for example at a nick site), but the nucleotide cannot form downstream phosphodiester linkages until the terminator is reversed. Reversal can be performed using techniques known to one skilled in the art. For example, the terminator can be attached to the nucleotide via cleavable linker, which can be cleaved, for example, via electromagnetic radiation. If nick repair is performed using labeled nucleotides comprising a 3' reversible terminator, a single labeled nucleotide can be incorporated into the nick, but the terminator can prevent additional labeled nucleotides from being incorporated into the nick. Accordingly, nick labeling can be limited to one labeled nucleotide per nick. Limiting nick labeling to one label moiety per nick can minimize potential bias from multiple labels being incorporated into the same nick. For example, if approaches are taken to limit labeling to one label moiety per nick, two nicks that are very close together can be resolved based on a relatively strong signal from the label (i.e. the possibility that two labels simply got incorporated into the same nick can be ruled-out). For example, if quantitative estimates of the number of nicks are desired, a one-label-per-nick approach can facilitate direct correlation between strength of label signal and the number of nicks. The label on the nucleotide comprising a reversible terminator can be as described herein. In some embodiments, the nucleotide comprising a reversible terminator comprises a quantum dot. In some embodiments, the nucleotide comprising a reversible terminator comprises a fluorophore. In some embodiments, the nucleotide comprising a reversible terminator comprises a non-optical label.

In some embodiments, a plurality of labels label a single sample molecule. In some embodiments, at least one of the labels comprises a sequence specific label. In some embodiments, at least one of the labels comprises a non-sequence specific label. In some embodiments, at least one label comprises a sequence specific label, and at least one label comprises a non-sequence specific label. In some embodiments, at least one label does not cut one or both strands of DNA. For example, in some embodiments, at least one label is selected from the group consisting of a non-cutting restriction enzyme, a methyltransferase, a zinc finger protein, an antibody, a transcription factor, a DNA binding protein, a hairpin polyamide, a triplex-forming oligodeoxynucleotide, a peptide nucleic acid, or a combination thereof. In some embodiments, neither the sequence specific nor the non-sequence specific label cuts DNA.

In some embodiments, for example if fluorescent labeling is provided, labeling is detected using a sensitive camera. In some embodiments, for example if non-optical labeling is provided, labeling is detected electronically. However, any detection method can be used that is suitable for the corresponding label. The methods described herein can include binding to a fluorescent label, a radioactive label, a magnetic label, or any combination thereof in one or more regions of the molecules described herein. Binding may be accomplished where the label is specifically complementary to a molecule or to at least a portion of a molecule or other region of interest.

In some embodiments, nicking enzymes create sequence-specific nicks that are subsequently labeled, for example using a labeled nucleotide or nucleotide analog. In some embodiment, the nucleotide or analog is fluorescently labeled. In some embodiments, DNA is linearized by confinement in a nanochannel, resulting in uniform linearization and allowing precise and accurate measurement of the distance between nick-labels on DNA molecules comprising a signature pattern. In some embodiments, a second nicking enzyme is used. In some embodiments, the second nicking enzyme is used with a second label color. Exemplary nickases that can be used in accordance with embodiments herein include, but are not limited to Nb.BbvCI; Nb.BsmI; Nb.BsrDI; Nb.BtsI; Nt.AlwI; Nt.BbvCI; Nt.BspQI; Nt.BstNBI; Nt.CviPII; Nt/Nb.BssSI, and combinations thereof. Examples of nicking agents and protocols are also provided in U.S. Patent Application Publication No. 2011/0171634 and U.S. Patent Application Publication No. 2012/0237936, which are hereby incorporated by reference in their entireties.

In some embodiments, a polynucleotide, for example an RNA or DNA, is labeled by hybridizing a probe to a single strand of the polynucleotide. The probe can be complementary to a strand of the RNA or DNA or a portion thereof. In some embodiments, the probe is complementary to a particular sequence motif. In some embodiments, a plurality of probes is provided so as to be complementary to a plurality of specific sequence motifs, for example at least 2, 3, 4, 5, 6, 7, 8, 9, 10, 20, 30, 40, 50, 60, 70, 80, 90, 100, 200, 300, 400, 500, 600, 700, 800, 900, 1000, 5,000, or 10,000 probes, including ranges between any two of the listed values. In some embodiments, the probe has a random sequence. In some embodiments, a probe with a plurality of random sequences is provided. In some embodiments, a probe includes one or more of an organic fluorophore, quantum dot, dendrimer, nanowires, bead, Au beads, paramagnetic beads, magnetic bead, a radiolabel, polystyrene bead, polyethylene bead, peptide, protein, haptens, antibodies, antigens, streptavidin, avidin, neutravidin, biotin, nucleotide, oligonucleotide, sequence specific binding factors such as engineered restriction enzymes, methlytransferases, zinc finger binding proteins, and the like. In some embodiments, the probe includes a fluorophore-quencher pair. One configuration of the probe can include a fluorophore attached to the first end of the probe, and an appropriate quencher tethered to the second end of the probe. As such, when the probe is unhybridized, the quencher can prevent the fluorophore from fluorescing, while when the probe is hybridized to a target sequence, the probe is linearized, thus distancing the quencher from the fluorophore and permitting the fluorophore to fluoresce when excited by an appropriate wavelength of electromagnetic radiation. In some embodiments, a first probe includes a first fluorophore of a FRET pair, and a second probe includes a second fluorophore of a FRET pair. As such, hybridization of the first probe and the second probe to a single flap, or to a pair of flaps within a FRET radius of each other can permit energy transfer by FRET. In some embodiments, a first probe includes a first fluorophore of a FRET pair, and a label on a nucleotide incorporated to fill a corresponding gap can include second fluorophore of a FRET pair. As such, hybridization of the first probe to a flap, and the labeled nucleotide into the corresponding gap can permit energy transfer by FRET.

In some embodiments, a double-stranded DNA can be labeled by first melting hydrogen bonds between double stands of certain genomic regions to open a so-called D-loop, by increasing temperature or manipulation with organic solvent, and then hybridizing to at least one specific probes with equal or higher affinity to single stranded regions before annealing back to relative stable form. As such, in some embodiments, double-stranded DNA can be labeled by a probe as described herein without nicking or cutting either strand. In some embodiments, a plurality of D-loops can be opened on a single strand. As such, a plurality of probes can be annealed to a particular double-stranded DNA.

In some embodiments, labeling comprises transferring a label to the polynucleotide via a methyltransferase. In some embodiments, the methyltransferase specifically methylates a sequence motif. As such, labeling can comprise transferring a label to a sequence motif by the methyltransferase. Exemplary suitable DNA methyltransferases (MTase) include, but are not limited to, M.BseCI (methylates adenine at N6 within the 5'-ATCGAT-3' sequence), M.TaqI (methylates adenine at N6 within the 5'-TCGA-3' sequence) and M.HhaI (methylates the first cytosine at C5 within the 5'-GCGC-3' sequence). In some embodiments, two or more methyltransferases provide two or more labels, which can be the same or different.

In some embodiments, the channel comprises a microchannel. In some embodiments, the channel comprises a nanochannel. Suitable fluidic nanochannel segments have a characteristic cross-sectional dimension of less than about 1000 nm, less than about 500 nm, or less than about 200 nm, or less than about 100 nm, or even less than about 50 nm, about 10 nm, about 5 nm, about 2 nm, or even less than about than about 0.5 nm. A fluidic nanochannel segment suitably has a characteristic cross-sectional dimension of less than about twice the radius of gyration of the molecule. In some embodiments, the nanochannel has a characteristic cross-sectional dimension of at least about the persistence length of the molecule. Fluidic nanochannel segments suitable for some embodiments herein have a length of at least about 100 nm, of at least about 500 nm, of at least about 1000 nm, of at least about 2 microns, of at least about 5 microns, of at least about 10 microns, of at least about 1 mm, or even of at least about 10 mm. Fluidic nanochannel segments are, in some embodiments, present at a density of at least 1 fluidic nanochannel segment per cubic centimeter.

Examples of fluidic channels can be found in U.S. Patent Publication No. 2008/0242556, which is incorporated herein by reference in its entirety. In some embodiments, a virion particles or a bacterial cell is assayed. For example, in some embodiments, a bacterial cell is assayed using a microchannel. In some embodiments, the channel allows a cell with a diameter in the range of microns to tens of microns to flow through.

FIG. 1 is a schematic diagram illustrating a fluidic channel arrangement according to some embodiments herein. The arrangement can include a sample input chamber 10. The arrangement can include an array of fluidic channels 12, for example fluidic nanochannels. The arrangement can include a sample output chamber 14. The output chamber can comprise buffer solution 16. The array of nanofluidic channels 12 can be in fluid communication with the input chamber 10. The array of nanofluidic channels 12 can be in fluid communication with the output chamber 14. Sample molecules or particles of interest 18 can be disposed in the array of nanofluidic channels 10. Control or comparative molecules or particles of interest 18 can be disposed in the array of nanofluidic channels 10. In some embodiments, the array of nanofluidic channels 12 connect the input chamber 10 to the output chamber 14. In some embodiments, sample molecules or particles of interest 18 and control or comparative molecules or particles of interest 20 are loaded into the sample input chamber, and travel in buffer solution 16 through the array of nanofluidic channels. In some embodiments, the sample molecules or particles of interest 18 and control or comparative molecules or particles of interest 20 are deposited from the array of nanofluidic channels 12 into the sample output chamber 14.

Figure 2:
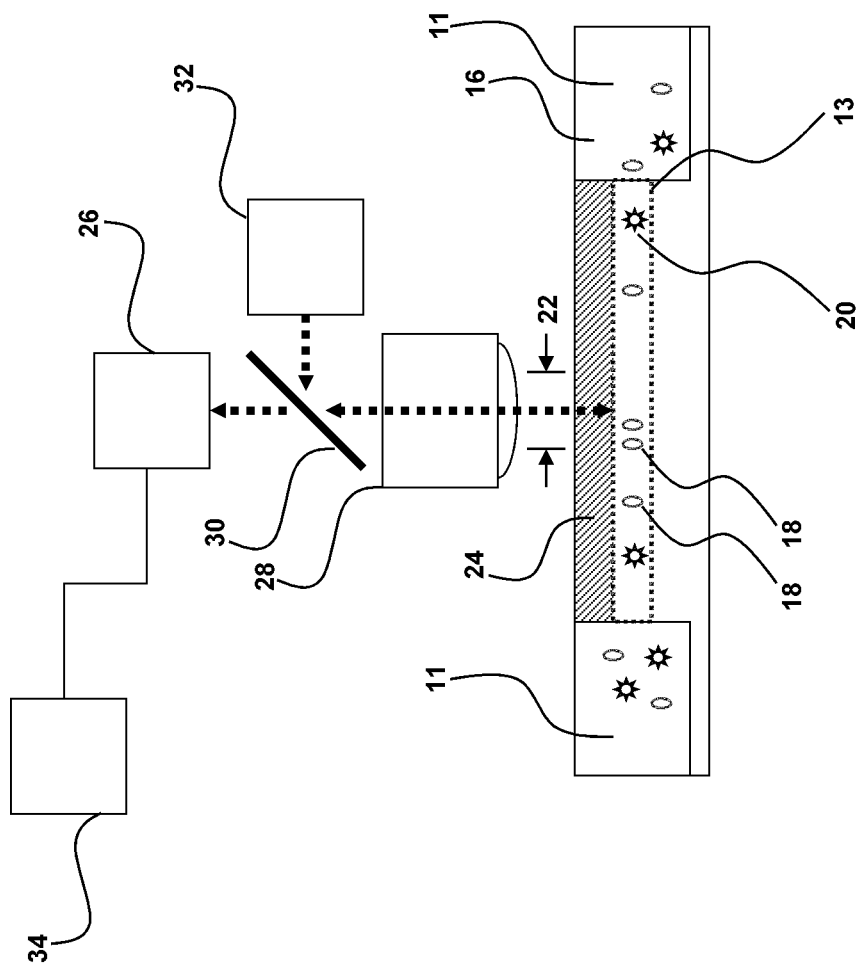
FIG. 2 is a schematic diagram illustrating an imaging setup in accordance with some embodiments herein to detect signals emitted from labeled molecules or particles to tabulate the amount, intensity, and configuration of the sample and reference molecule or particles.

FIG. 2 is a schematic diagram illustrating an arrangement for detection of sample molecules or particles of interest according to some embodiments herein. In some embodiments, the arrangement comprises a first sample inlet or outlet 11, a second sample inlet or outlet 11, and at least one fluidic channel 13 positioned therebetween and in fluid communication with each of the first and second inlet or outlet 11. It is contemplated herein that if a sample is loaded into the first inlet or outlet 11, the first inlet or outlet 11 functions as an inlet and the second inlet or outlet 11 can function as an outlet. It is contemplated herein that if a sample is loaded into the second inlet or outlet 11, the second inlet or outlet 11 functions as an inlet and the first inlet or outlet 11 can function as an outlet. In some embodiments, the sample comprises molecules or particles of interest 18, control or comparative particles of interest 20, or a combination of the two. In some embodiments, the molecules or particles of interest 18, control or comparative particles of interest 20 travel through the fluidic channel 13. In some embodiments, the fluidic channel 13 comprises a nanochannel. In some embodiments, the fluidic channel 13 comprises a microchannel. In some embodiments, the fluidic channel 13 comprises a detection region 22. In some embodiments, the system comprises a cover 24 disposed over the detection region 24. In some embodiments, the cover 24 comprises a transparent cap. In some embodiments, a detector 26 is positioned over the detection region 22 and the cover 24 (if present). In some embodiments, for example, if optical detection is used, the detector 26 comprises a photon detection/imager. In some embodiments, a lens 28 is positioned in optical communication with the detection region 22 and detector 26. In some embodiments, the lens 28 is positioned between detection region 22 and detector 26. In some embodiments, a dichroic mirror 30 is positioned in an optical communication with the detection region 22, lens 28, detector 26, and an excitation source 32, so that a fluorescent label, if present, can be excited, and fluorescence from the fluorescent label, if present, can be detected. In some embodiments, the detector 26 is in data communication with a processor 34. The processor 34 can be configured to generate genome maps as described herein, based on data from the detector. In some embodiments, the processor is configured to assemble genome maps as described herein. In some embodiments, the processor is configured to automatically minimize or eliminate bias based on labeling density and/or factor other than labeling density, for example by implementing GROM and/or SIMONIDA as described herein. In some embodiments, the processor is configured to automatically detect structural variations in the genome, for example complex duplications, deletions, translocations, or rearrangements. The automatic detection of structural variations can comprise determining GROM and/or SIMONIDA copy number breakpoints as described herein. The automatic detection can further comprise comparing the GROM and/or SIMONIDA copy number breakpoints to a second algorithm for identify structural variations as described herein. The automatic detection can further comprise comparing the GROM copy number breakpoints to SIMONIDA copy number breakpoints as described herein.

In some embodiments, the comparison of samples to a reference sample is provided in the form of a histogram. In some embodiments, physical counting of molecules with a particular labeling pattern that matches to a reference or de novo genomic assembly in silico are tabulated in a histogram distribution to reflect coverage depth. A higher or lower than average coverage depth in specific region or entire chromosome reflects the deviation from normal ploidy such as in the case of aneuploidy in genetic disorder or structural variations in cancer.

ADDITIONAL ALTERNATIVE EMBODIMENTS

According to some embodiments herein, GROM differs from PERUN. In some embodiments, the technologies used to generate input data are different in GROM and PERUN. In some embodiments, types of input data are different in GROM and PERUN. For example, PERUN can utilize next generation sequencing (NGS) data, and GROM can utilize labeled mapping data, for example data obtaining on an Irys™ system (Bionano Genomics). For example, PERUN can utilize polynucleotide sequence reads, and GROM can utilize genomic maps as inputs, respectively. In some embodiments, alignment methodologies are different in GROM and PERUN, for example, NGS mapping for PERUN, and labeled map alignment for GROM. In some embodiments, raw coverage depth evaluation are different in GROM and PERUN, for example, simple counting in the case of PERUN, and average per-label coverage in the case of GROM. In some embodiments, types of biases being addressed are different in GROM and PERUN. For example, PERUN can address bias arising from GC frequency, and GROM can address bias arising from label density. In some embodiments, descriptors of a sample's behavior are different in GROM and PERUN, for example sample-specific GC coefficient in the case of PERUN, and sample-specific label density bias in the case of GROM.

According to some embodiments herein, a method of characterizing sample is provided. The method can comprise labeling a plurality of sample molecules with at least a first label, wherein the sample molecules comprise polynucleotide sequences of a first genomic fragment or fragments of interest. The method can comprise providing a plurality of labeled reference molecules, wherein the reference molecules comprise polynucleotide sequences of a reference genomic fragment or fragments, and wherein the reference genomic fragment or fragments are of a known copy number. The method can comprise translocating the plurality of labeled sample molecules and the plurality of labeled reference molecules though a fluidic channel. The method can comprise detecting signals from the labeled sample molecules and labeled reference molecules so as to ascertain at least a first pattern or plurality of patterns characteristic of the first genomic fragment or fragments of interest, and a second pattern or plurality of patterns characteristic of the reference genomic fragment or fragments. The method can comprise correlating signals ascertaining the first pattern or plurality of patterns to signals ascertaining the second pattern or plurality of patterns, so as to generate a copy number profile of the sample molecules, and in which bias due to label density is minimized or eliminated in the copy number profile. In some embodiments, generating a copy number profile comprises performing GROM. In some embodiments, generating a copy number profile comprises generating a raw coverage depth profile per interval from the detected signal, transforming the raw coverage depth profile to a corresponding scaled coverage depth profile per interval, generating a sample-specific label density bias coefficient (LDBC), parameterizing intervals, wherein the interval parameters comprise gradient and zero-order coefficient values, filtering intervals based on at least on measurement of error, normalizing scaled coverage depth with respect to LDBC, and generating a plurality of copy number profiles from the normalized coverage depth profiles. In some embodiments, the method further comprises storing the raw coverage depth profile in a computer readable medium. In some embodiments, measurement of error comprises relative errors. In some embodiments, the intervals are of equal size. In some embodiments, the intervals are not of equal size. In some embodiments, each interval comprises about 10,000 to about 90,000 base pairs. In some embodiments, each interval comprises about 40,000 to about 60,000 base pairs. In some embodiments, the scaled coverage depth profile comprises at least about 20,000 intervals. In some embodiments, the scaled coverage depth profile comprises at least about 40,000 intervals. In some embodiments, the method further comprises automatically determining a presence or absence of aneuploidy of a chromosome comprising the first genomic fragment or fragments of interest.

In some embodiments, the method further comprises automatically determining a presence or absence of possible structural variation in the first genomic fragment or fragments of interest. In some embodiments, the method further comprises automatically determining a presence or absence of possible structural variation comprises identifying possible breakpoints in the copy number profile, wherein an interval in the copy number profile with a significantly different copy number than a neighboring interval comprises a possible breakpoint. In some embodiments, automatically determining a presence or absence of possible structural variation comprises determining GROM copy number breakpoints. In some embodiments, the method further comprises determining a second plurality of possible structural variants using a second algorithm, and identifying overlap between the GROM copy number breakpoints and the second plurality of possible structural variants. In some embodiments, the second algorithm comprises RPSA. In some embodiments, GROM is coupled with an RPSA analysis as follows: An RPSA complex SV call is made, in which the SV call comprises two breakpoints, and for each of the RPSA SV breakpoints, the p-values from GROM copy number profile changes are evaluated, and if a given $-\log 10(p)$ is greater than three (3) standard deviations (SD's), the p-value is determined to be significant. In some embodiments, the method further comprises, for each of the GROM copy number breakpoints, identifying a first region of a reference sequence on a first side of the breakpoint, and masking a second region of the reference sequence on a second side of the breakpoint, wherein the second side is opposite the first side; and scoring only single molecule alignments that align with reference labels in the first region. In some embodiments, the method further comprises clustering single molecule alignments to the second region, and aligning each cluster to a reference sequence. In some embodiments, the copy number profile is generated in real-time. In some embodiments, the copy number profile is generated in less than five minutes after the signals are detected. In some embodiments, the copy number profile is generated in less than 60 seconds after the signals are detected. In some embodiments, the copy number profile is generated by a processor in data communication with a detector to detect signals from the labeled sample molecules and labeled reference molecules. In some embodiments, the sample molecules and reference molecules are from the same sample. In some embodiments, the sample molecules and reference molecules are from different samples. In some embodiments, the sample molecules and reference molecules are from the same organism. In some embodiments, the signals of the reference molecules comprise an electronically or optically stored value or set of values. In some embodiments, the first genomic fragment or fragments of interest comprise a sex chromosome or a least one fragment thereof, and the reference genomic fragment or fragments comprise an autosome or at least one fragment thereof. In some embodiments, the first genomic fragment or fragments of interest comprise a first autosome or at least one fragment thereof, selected from the group consisting of: human chromosome 21, human chromosome 13, human chromosome 14, human chromosome 15, human chromosome 16, human chromosome 18, and human chromosome 22, and fragments thereof, and the reference genomic fragment or fragments comprise a second autosome or at least one fragment thereof, wherein the second autosome or fragment thereof is different than the first autosome or fragment thereof. In some embodiments, the genomic fragment or fragments comprises an autosome or at least one fragment thereof, selected from the group consisting of: human chromosome 1, human chromosome 2, human chromosome 3, human chromosome 4, human chromosome 5, human chromosome 6, human chromosome 7, human chromosome 8, human chromosome 9, human chromosome 10, human chromosome 11, human chromosome 12, human chromosome 13, human chromosome 14, human chromosome 15, human chromosome 16, human chromosome 17, human chromosome 18, human chromosome 19, human chromosome 20, human chromosome 21, human chromosome 22, human chromosome X, human chromosome Y, and fragments thereof, and the reference genomic fragment or fragments comprise a second autosome or at least one fragment thereof, wherein the second autosome or fragment thereof is different than the first autosome or fragment thereof. In some embodiments, the sample molecules are from a sample comprising a possible genomic abnormality, and the reference genomic fragment or fragments comprise a first chromosome or fragment thereof, and the reference genomic fragments are from a second sample known to not comprise the genomic abnormality. In some embodiments, the genetic abnormality comprises at least one of a duplication, deletion, or translocation. In some embodiments, labeling comprises labeling the sample molecules with a first label, and wherein the reference molecules comprise a second label, in which the first label is configured to produce the first pattern or plurality of patterns, and in which the second label is configured to produce the second pattern or plurality of patterns, and in which wherein the first label and the second label are different from each other. In some embodiments, labeling comprises labeling with a first label, in which the first pattern or plurality of patterns and the second pattern or plurality of patterns each comprise the first label, and in which the first pattern or plurality of patterns and second pattern or plurality of patterns are different from each other. In some embodiments, the method further comprises labeling reference molecules so as to produce the labeled reference molecules, wherein the labeled reference molecules comprise the second pattern or plurality of patterns. In some embodiments, the first label comprises at least one of a fluorescent label, a radioactive label, a magnetic label, or a non-optical label. In some embodiments, the second label comprises at least one of a fluorescent label, a radioactive label, a magnetic label, or a non-optical label. In some embodiments, labeling comprises nicking one strand of a double-stranded DNA at a first sequence motif with a nicking endonuclease, and labeling the DNA. In some embodiments, labeling further comprises repairing at least some of the nicks on the DNA. In some embodiments, the nicks are not repaired. In some embodiments, the label comprises a transcriptional terminator. In some embodiments, labeling with the first label comprises tagging at least one sequence motif of the sample molecules with a DNA binding entity selected from the group consisting of: a non-cutting restriction enzyme, a zinc finger protein, an antibody, a transcription factor, a transcription activator like domain, a DNA binding protein, a polyamide, a triple helix forming oligonucleotide, and a peptide nucleic acid, and a methyltransferase. In some embodiments, labeling with the first label comprises tagging at least one sequence motif of the sample molecules with a methyltransferase. In some embodiments, the method further comprises labeling the sample molecule with a non-sequence-specific label. In some embodiments, the non-sequence-specific label comprises a YOYO or POPO dye.

According to some embodiments herein, a method of characterizing a sample is provided. The method can comprise labeling a plurality of sequence-specific locations on a polynucleotide sequence of a sample molecule. The method can comprise linearizing at least a portion of the sample molecule in a fluidic channel. The method can comprise quantifying a signal from the labels on the sample molecule. The method can comprise generating a copy number profile of the sample molecule. The method can comprise determining a presence or absence of a genetic abnormality in the sample DNA when the quantity of the signal from the sample molecule differs from the quantity of the signal arising from a reference molecule. In some embodiments, generating a copy number profile comprises performing GROM. In some embodiments, generating a copy number profile comprises generating a raw coverage depth profile per interval from the detected signals, transforming the raw coverage depth profile to a corresponding scaled coverage depth profile per interval, generating a sample-specific label density bias coefficient (LDBC), parameterizing intervals, wherein the interval parameters comprise gradient and zero-order coefficient values, filtering intervals based on at least on measurement of error, normalizing scaled coverage depth with respect to LDBC, and generating a plurality of copy number profiles from the normalized coverage depth profiles. In some embodiments, the intervals are of equal size. In some embodiments, the intervals are not of equal size. In some embodiments, each interval comprises about 10,000 to about 90,000 base pairs. In some embodiments, the scaled coverage depth profile comprises at least about 20,000 intervals. In some embodiments, determining a presence or absence of a genetic abnormality comprises identifying a plurality of intervals for a chromosome or portion thereof, wherein the each interval of the plurality has a significantly different copy number than the reference molecule. In some embodiments, the method further comprises automatically determining a presence or absence of possible structural variation in the first genomic fragment or fragments of interest. In some embodiments, automatically determining a presence or absence of possible structural variation comprises identifying possible breakpoints in the copy number profile, wherein an interval in the copy number profile with a significantly different copy number than a neighboring interval comprises a possible breakpoint. In some embodiments, automatically determining a presence or absence of possible structural variation comprises determining GROM copy number breakpoints. In some embodiments, the sample molecule and the reference molecule are from the same organism. In some embodiments the sample molecule and the reference molecule are from different tissues of the same organism. In some embodiments, the sample molecule and the reference molecule are from different organisms. In some embodiments, the quantity of signal from the reference molecule comprises an electronically or optically stored value or set of values. In some embodiments, the sample molecule comprises a DNA. In some embodiments, the genetic abnormality comprises at least one of a translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy, tetraploidy, or sex chromosome aneuploidy. In some embodiments, the genetic abnormality comprises at least one of a hypopolyploidy or hyperpolyploidy. In some embodiments, labeling comprises labeling the polynucleotide with at least one of a fluorescent label, a radioactive label, a magnetic label, or a non-optical label. In some embodiments, labeling comprises nicking one strand of a double-stranded DNA at a first sequence motif with a nicking endonuclease, and labeling the DNA. In some embodiments, the method further comprises repairing at least some of the nicks on the first DNA. In some embodiments, the nicks are not repaired. In some embodiments, the label comprises a transcriptional terminator. In some embodiments, labeling comprises tagging at least one sequence motif of the sample molecules with a DNA binding entity selected from the group consisting of: a non-cutting restriction enzyme, a zinc finger protein, an antibody, a transcription factor, a transcription activator like domain, a DNA binding protein, a polyamide, a triple helix forming oligonucleotide, and a peptide nucleic acid, and a methyltransferase. In some embodiments, labeling with the first label comprises tagging at least one sequence motif of the sample molecules with a methyltransferase.

In some embodiments, the fluidic nanochannel of any of the methods herein comprises a channel having a length of at least 10 nm and a cross-section diameter of less than 5000 nm. In some embodiments, the fluidic channel comprises a nanochannel. In some embodiments, the fluidic channel is disposed parallel to a surface of a substrate. In some embodiments. In some embodiments, the translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

In some embodiments, the sample of any of the methods herein is selected from the group consisting of a bacteria, a virion, a DNA molecule, an RNA molecule, a nucleic acid polymer, a protein, a peptide, and a polysaccharide. In some embodiments, the sample of any of the methods herein is derived from maternal blood, and wherein the reference molecule is derived from a maternal sample other than blood. In some embodiments, the sample of any of the methods herein comprises a nucleotide, and wherein the at least two labels are located at either end of a zone of interest in the nucleotide. In some embodiments, the sample of any of the methods herein comprises circulating fetal cells, circulating tumor cells, or body fluids or tissues.

In some embodiments, any of the methods herein comprises optical inspection comprising determining the physical count, the intensity, the wavelength, or the size of the labels. In some embodiments, any of the methods herein comprise optical inspection comprising determining the length of at least one labeled region in the sample. In some embodiments, any of the methods herein, further comprise determining the signals arising from a pool comprising the sample or portions of the sample.

In some embodiments, any of the methods herein comprises using the ratio (K) between the signal arising from a plurality of samples or sample portions (S1, S2 . . . Sn) and the signal arising from the reference (C): K1=S1/C, K2=S2/C . . . Kn=Sn/C In some embodiments, a difference between K1 and Kn is used to identify the presence of a fetal sample. In some embodiments, a difference between K1 and Kn is used to identify the presence of DNA from a tumor or other cancer source. In some embodiments, a difference between K1 and Kn is used to determine the presence of a genetic abnormality in the sample. In some embodiments, the genetic abnormality is aneuploidy. In some embodiments, the genetic abnormality is a translocation, addition, amplification, transversion, or inversion.

In some embodiments, any of the methods herein comprises a reference derived from a known diploid or haploid chromosome. In some embodiments, any of the methods herein comprises correlating signals from the sample with the population distribution from a metagenomic or microbiome study. In some embodiments, any of the methods herein comprises generating a histogram distribution to reflect coverage depth for the sample.

In some embodiments, a system for characterizing a sample is provided. The system can comprise one or more regions for labeling sample molecules with at least two labels. The system can comprise a fluidic channel for translocating the labeled sample molecules, wherein the fluidic channel is configured to elongate at least a portion of the sample molecule, and wherein the fluidic channel has a length of at least 10 nm and a cross-sectional diameter of less than 5000 nm. The system can comprise a device for detecting signals arising from the labeled samples in the fluidic channels. The system can comprise a processor in data communication with the device, wherein the processor is configured to eliminate or minimize at least one of: biases caused by label density on the labeled sample molecules; or biases caused by factors other than label density of the labeled sample molecules. In some embodiments, the processor is configured to eliminate or minimize at least one of the biases using Global Renormalization of Optical Maps (GROM). In some embodiments, GROM comprise generating a raw coverage depth profile per interval, transforming the raw coverage depth profile to a corresponding scaled coverage depth profile per interval, generating a sample-specific label density bias coefficient (LDBC), parameterizing intervals, wherein the interval parameters comprise gradient and zero-order coefficient values, filtering intervals based on at least on measurement of error, normalizing scaled coverage depth with respect to LDBC; and generating of copy number profiles from the normalized coverage depth profiles. In some embodiments, the processor is configured to automatically determine a presence or absence of possible structural variation in the first genomic fragment or fragments of interest. In some embodiments, the processor is configured to automatically identify possible breakpoints in the copy number profile, wherein an interval in the copy number profile with a significantly different copy number than a neighboring interval comprises a possible breakpoint. In some embodiments, the processor is configured to automatically determine GROM copy number breakpoints. In some embodiments, the processor is configured to automatically determine statistically significant differences in GROM copy number. In some embodiments, the processor is further configured to determine a second plurality of possible structural variants using a second algorithm; and identify overlap between the GROM copy number breakpoints and the second plurality of possible structural variants. In some embodiments, the processor is further configured to, for each of the GROM copy number breakpoints, identify a first region of a reference sequence on a first side of the breakpoint, and masking a second region of the reference sequence on a second side of the breakpoint, wherein the second side is opposite the first side, and score only single molecule alignments that align with reference labels in the first region.

In some embodiments, the fluidic channel of any of the systems as described herein comprises a nanochannel. In some embodiments, the fluidic channel of any of the systems as described herein is disposed parallel to a surface of a substrate. In some embodiments, the translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

Some embodiments described herein can include the following: A method of characterizing a sample, comprising: labeling a region of sample molecules with at least two labels; translocating the labeled sample molecules through a fluidic channel, wherein the fluidic channel is configured to elongate at least a portion of the sample molecule, and wherein the fluidic channel has a length of at least 10 nm and a cross-sectional diameter of less than 5000 nm; detecting signals arising from the labeled samples in the fluidic channels; and correlating the signals arising from the labeled samples to signals arising from the corresponding region of a reference molecule. The method can further comprise: labeling a region of the reference molecule corresponding to the region of the sample molecules; translocating the labeled reference sample molecule through a fluidic channel, wherein the fluidic channel is configured to elongate at least a portion of the sample molecule, and wherein the fluidic channel has a length of at least 10 nm and a cross-sectional diameter of less than 5000 nm; and detecting signals arising from the labeled reference sample in the fluidic channels, wherein the signals arising from a known corresponding region of a reference molecule are the signals arising from the labeled reference sample.

In some embodiments, a method of characterizing a sample is provided. The method can comprise: labeling sample nucleic acid molecules; translocating the labeled sample nucleic acid molecules through a fluidic nanochannel, wherein the fluidic nanochannel is configured to elongate at least a portion of the sample nucleic acid molecules, and wherein the fluidic nanochannel has a length of at least 10 nm and a cross-sectional diameter of less than 1000 nm; detecting signals arising from the sample nucleic acid molecules in the fluidic channels; determining the positions of the labels on the sample nucleic acid molecules; and aligning the positions of the labels on the sample nucleic acid molecules to the position of labels in a reference genome.

In some embodiments, a method of characterizing a sample is provided. The method can comprise: processing double-stranded DNA samples so as to give rise to a flap of the first strand of the double-stranded DNA samples being displaced from the double-stranded DNA samples, wherein the flap has a length in the range of from about 1 to about 1000 bases, and wherein the flap gives rise to a gap in the first strand of the double-stranded DNA samples corresponding to the flap; incorporating one or more bases into the double-stranded DNA so as to eliminate at least a portion of the gap; labeling at least a portion of the processed double-stranded DNA with one or more tags; and quantifying the signal arising from the labels on the double-stranded DNA; comparing the quantity of the signal arising from the double-stranded DNA to the quantity of the signal arising from a reference DNA; and determining the presence of a genetic abnormality in the double-stranded DNA when the quantity of the signal arising from the double-stranded DNA differs from the quantity of the signal arising from the reference DNA.

In some embodiments, a method of characterizing a sample is provided. The method can comprise labeling a plurality of sequence-specific locations on a sample DNA; linearizing at least a portion of the sample DNA; quantifying the signal arising from the labels on the sample DNA; comparing the quantity of the signal arising from the sample DNA to the quantity of the signal arising from a reference DNA: and determining the presence of a genetic abnormality in the sample DNA when the quantity of the signal arising from the sample DNA differs from the quantity of the signal arising from the reference DNA.

In some embodiments, a system for characterizing a sample is provided. The system can comprise: one or more regions for labeling sample molecules with at least two labels; a fluidic channel for translocating the labeled sample molecules, wherein the fluidic channel is configured to elongate at least a portion of the sample molecule, and wherein the fluidic channel has a length of at least 10 nm and a cross-sectional diameter of less than 5000 nm; and a device for detecting signals arising from the labeled samples in the fluidic channels.

In some embodiments, a system for characterizing a sample is provided. The system can comprise: one or more regions for labeling sample nucleic acid molecules; a fluidic nanochannel for translocating the labeled sample nucleic acid molecules, wherein the fluidic nanochannel is configured to elongate at least a portion of the sample nucleic acid molecules, and wherein the fluidic nanochannel has a length of at least 10 nm and a cross-sectional diameter of less than 1000 nm; and a device for detecting signals arising from the sample nucleic acid molecules in the fluidic channels.

In some embodiments, a system for characterizing a sample is provided. The system can comprise: one or more regions for processing double-stranded DNA samples so as to give rise to a flap of the first strand of the double-stranded DNA samples being displaced from the double-stranded DNA samples, wherein the flap has a length in the range of from about 1 to about 1000 bases, and wherein the flap gives rise to a gap in the first strand of the double-stranded DNA samples corresponding to the flap: one or more regions for incorporating one or more bases into the double-stranded DNA so as to eliminate at least a portion of the gap: one or more regions for labeling at least a portion of the processed double-stranded DNA with one or more tags; and a device for quantifying the signal arising from the labels on the double-stranded DNA.

In some embodiments, a system for characterizing a sample is provided. The system can comprise: a region for labeling a plurality of sequence-specific locations on a sample DNA; a region for linearizing at least a portion of the sample DNA; and a device for quantifying the signal arising from the labels on the sample DNA.

In some embodiments, a system for characterizing a sample is provided. The system can comprise: means for labeling sample molecules with at least two labels; means for linearizing the labeled sample molecules; and means for detecting signals arising from the labeled samples in the fluidic channels.

In some embodiments, a system for characterizing a sample is provided. The system can comprise: means for labeling sample nucleic acid molecules; means for linearizing the labeled sample nucleic acid molecules; and means for detecting signals arising from the sample nucleic acid molecules in the fluidic channels.

In some embodiments, a system for characterizing a sample is provided. The system can comprise: means for processing double-stranded DNA samples so as to give rise to a flap of the first strand of the double-stranded DNA samples being displaced from the double-stranded DNA samples, wherein the flap has a length in the range of from about 1 to about 1000 bases, and wherein the flap gives rise to a gap in the first strand of the double-stranded DNA samples corresponding to the flap; means for incorporating one or more bases into the double-stranded DNA so as to eliminate at least a portion of the gap; means for labeling at least a portion of the processed double-stranded DNA with one or more tags; and means for quantifying the signal arising from the labels on the double-stranded DNA.

In some embodiments, a system for characterizing a sample is provided. The system can comprise: system for characterizing a sample, comprising: means for labeling a plurality of sequence-specific locations on a sample DNA; means for linearizing at least a portion of the sample DNA; and means for quantifying the signal arising from the labels on the sample DNA.

According to some embodiments, a method or system as described herein is provided, wherein the sample is selected from the group consisting of a bacteria, a virion, a DNA molecule, an RNA molecule, a nucleic acid polymer, a protein, a peptide, and a polysaccharide.

According to some embodiments, a method or system as described herein is provided, wherein the sample is derived from maternal blood, and wherein the reference molecule is derived from a maternal sample other than blood.

According to some embodiments, a method or system as described herein is provided, wherein the sample comprises a nucleotide, and wherein the at least two labels are located at either end of a zone of interest in the nucleotide.

According to some embodiments, a method or system as described herein is provided, wherein the label is selected from the group consisting of a fluorescent label, a radioactive label, a magnetic label, or a combination thereof.

According to some embodiments, a method or system as described herein is provided, wherein the optical inspection comprises determining the physical count, the intensity, the wavelength, or the size of the labels.

According to some embodiments, a method or system as described herein is provided, wherein the optical inspection comprises determining the length of at least one labeled region in the sample.

According to some embodiments, a method or system as described herein is provided, wherein correlating the signals comprises determining the signals arising from a pool of samples or a pool of portions of a sample.

According to some embodiments, a method or system as described herein is provided, wherein correlating the signals comprises using the ratio (K) between the signal arising from a plurality of samples or sample portions (S1, S2 . . . Sn) and the signal arising from the reference (C): K1=S1/C, K2=S2/C . . . Kn=Sn/C. In some embodiments, a difference between K1 and Kn is used to identify the presence of a fetal sample. In some embodiments, a difference between K1 and Kn is used to identify the presence of DNA from a tumor or other cancer source. In some embodiments, a difference between K1 and Kn is used to determine the presence of a genetic abnormality in the sample. In some embodiments, the genetic abnormality is aneuploidy. In some embodiments, the genetic abnormality is a translocation, addition, amplification, transversion, or inversion. In some embodiments, the reference is derived from a known diploid or haploid chromosome. In some embodiments, the signals from the sample are correlated with the population distribution from a metagenomic or microbiome study.

According to some embodiments, a method or system as described herein is provided, in which the fluidic channel is a nanochannel. In some embodiments, the fluidic channel is disposed parallel to a surface of a substrate.

According to some embodiments, a method or system as described herein is provided, further comprising generating a histogram distribution to reflect coverage depth for the sample.

According to some embodiments, a method or system as described herein is provided, wherein the sample comprises circulating fetal cells, circulating tumor cells, or body fluids or tissues.

According to some embodiments, a method or system as described herein is provided, wherein the translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

According to some embodiments, a kit for performing a method as described herein is provided.

According to some embodiments, a kit for using the system of any one of the preceding claims is provided.

In the description provided herein, reference is made to the accompanying drawings, which form a part hereof. The illustrative embodiments described in the detailed description, drawings, and claims are not meant to be limiting.

Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Unless defined otherwise, technical and scientific terms used herein have the same meaning as commonly understood by one of ordinary skill in the art to which this invention belongs.

As used herein, the term "channel" means a region defined by borders. Such borders may be physical, electrical, chemical, magnetic, and the like. The term "nanochannel" is used to clarify that certain channels are considered nanoscale in certain dimensions.

As used herein, the term "DNA" refers to DNA of any length (e.g., 0.1 Kb to 1 megabase). The DNA can be a highly pure preparation, crude, or semi crude material. The DNA can come from any biological source or can be synthetic.

As used herein, the term "nucleotide" refers to a molecule containing deoxyribonucleic acids (e.g., DNA, mtDNA, gDNA, or cDNA), ribonucleic acid (e.g., RNA or mRNA), or any other variant of nucleic acids known in the art. The term "labeled nucleotide" refers to a nucleotide comprising any modification that is detectable. This includes but is not limited to nucleotides with reporter groups attached to the base. Reporter groups include but are not limited to fluorescent dyes, haptens, biotin molecules or gold nanoparticles. The term "native nucleotide" refers to a nucleotide that is not modified, or has a slight modification that does not interfere with its incorporation into DNA. The terms "t", "c", "a", "g" and "u" refer to nucleotides in DNA and RNA.

The term "nick" refers to a phosphodiester bond break occurring on one DNA strand or the other, having a 3'hydroxyl end.

As used herein, the term "nicking endonuclease" refers to any enzyme, naturally occurring or engineered, that is capable of breaking a phosphodiester bond on a single DNA strand leaving a 3'-hydroxylate a defined sequence. Nicking endonucleases can be naturally occurring, engineered by modifying restriction enzymes to eliminate one DNA strand cutting activity, or produced by fusing a nicking subunit to a DNA binding domain, for example, zinc fingers and transcription activator like effectors DNA recognition domains.

As used herein, the term "labeling sites" refers to any DNA site with an exposed 3' hydroxyl group onto which the polymerase can add nucleotides in a template dependent manner. Labeling sites can be generated by nicking endonucleases, hybridized probes, or any chemical or physical means of breaking a phosphodiester bond on any one DNA strand. Means of breaking a phosphodiester bond can occur to DNA outside its biological source or prior to DNA extraction, for example as a result of a biological sample exposure to chemicals, and external forces such as radiation. If 3' ends are not extendable, repair can be performed to restore the hydroxyl group, for example by using New England Biolabs' PreCR kit.

As used herein a "sample" can include, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein, the term "chromosome" refers to the heredity-bearing gene carrier of a living cell which is derived from chromatin and which comprises DNA and protein components (especially histones).

As used herein "ChrX" refers to the X chromosome, or chromosome X. As used herein "ChrY" refers to the Y chromosome or chromosome Y. Similarly, Chr1, Chr2, Chr3, etc. refer to Chromosome 1, Chromosome 2, Chromosome 3, etc.

As one of skill in the art will recognize, "translocating" can be used interchangeably with linearizing when used in the context passing a DNA molecule through a nanochannel.

The methods, apparatuses, systems, and kits described herein can incorporate the methods, apparatuses, systems, and kits described in any of the following references: U.S. Patent Application Publication No. 2009/0305273; PCT Publication No. WO/2008/079169; U.S. Patent Application Publication No. 2008/0242556; PCT Publication No. WO/2008/121828; U.S. Patent Application Publication No. 2011/0171634: PCT Publication No. WO/2010/002883; U.S. Patent Application Publication No. 2011/0296903; PCT Publication No. WO/2009/149362; U.S. Patent Application Publication No. 2011/0306504; PCT Publication No. WO/2010/059731; U.S. Patent Application Publication No. 2012/0097835; PCT Publication No. WO/2010/135323; PCT Application No. PCT/US11/57115; U.S. patent application Ser. No. 13/606,819; PCT Application No. PCT/US2012/054299; U.S. Patent Application Publication No. 2012/0244635; PCT Publication No. WO/2011/038327; U.S. Patent Application Publication No. 2012/0237936; U.S. patent application Ser. No. 13/503,307; PCT Publication No. WO/2011/050147; U.S. Patent Application Ser. No. 61/734,327; U.S. Patent Application Ser. No. 61/761,189; and U.S. Patent Application Ser. No. 61/713,862, which are each hereby incorporated by reference in their entireties.

References: The following references relate to assessment of genetic variation, and each is hereby incorporated by reference in its entirety: US Patent Application Pub No: 2013/085681; PCT Application Pub. No: WO2013/052907; PCT Application Pub. No: WO2013/052913; US Patent Application Pub No: 2013/0103320; US Patent Application Pub No: 2013/0261983; PCT Application Pub No: WO2013/109981; PCT Application Pub No: WO2013/177086; US Patent Application Pub No: 20130309666; US Patent Application Pub No: 20130325360; US Patent Application Pub No: 20130338933; PCT Application Pub No: WO2013/055817: US Patent Application Pub No: 2013/0150253; PCT Application No: PCT/US2013/047131 (published as WO 2013/192562); Džkula, , Mazloom, A., et al., (2013) Noninvasive prenatal detection of sex chromosomal aneuploidies by sequencing circulating cell-free DNA from maternal plasma. *J. Prenat Diagn.* 33:591-7; Jensen, T. J., et al. (2013) High-Throughput Massively Parallel Sequencing for Fetal Aneuploidy Detection from Maternal Plasma. *PLoS One.* 2013; 8:e57381; and Jensen, T. J., Džkula, , et al. (2012) Detection of microdeletion 22q11.2 in a fetus by next-generation sequencing of maternal plasma. *Clin Chem.* 58: 1148-51.

Example 1

Genomic fragments from a human male sample were generated by PCR, labeled, and run through a nanochannel. Detected fragments were then aligned to a single gene reference genome map for each chromosome. The molecules were sorted based on the alignment start site.

Figure 7A:
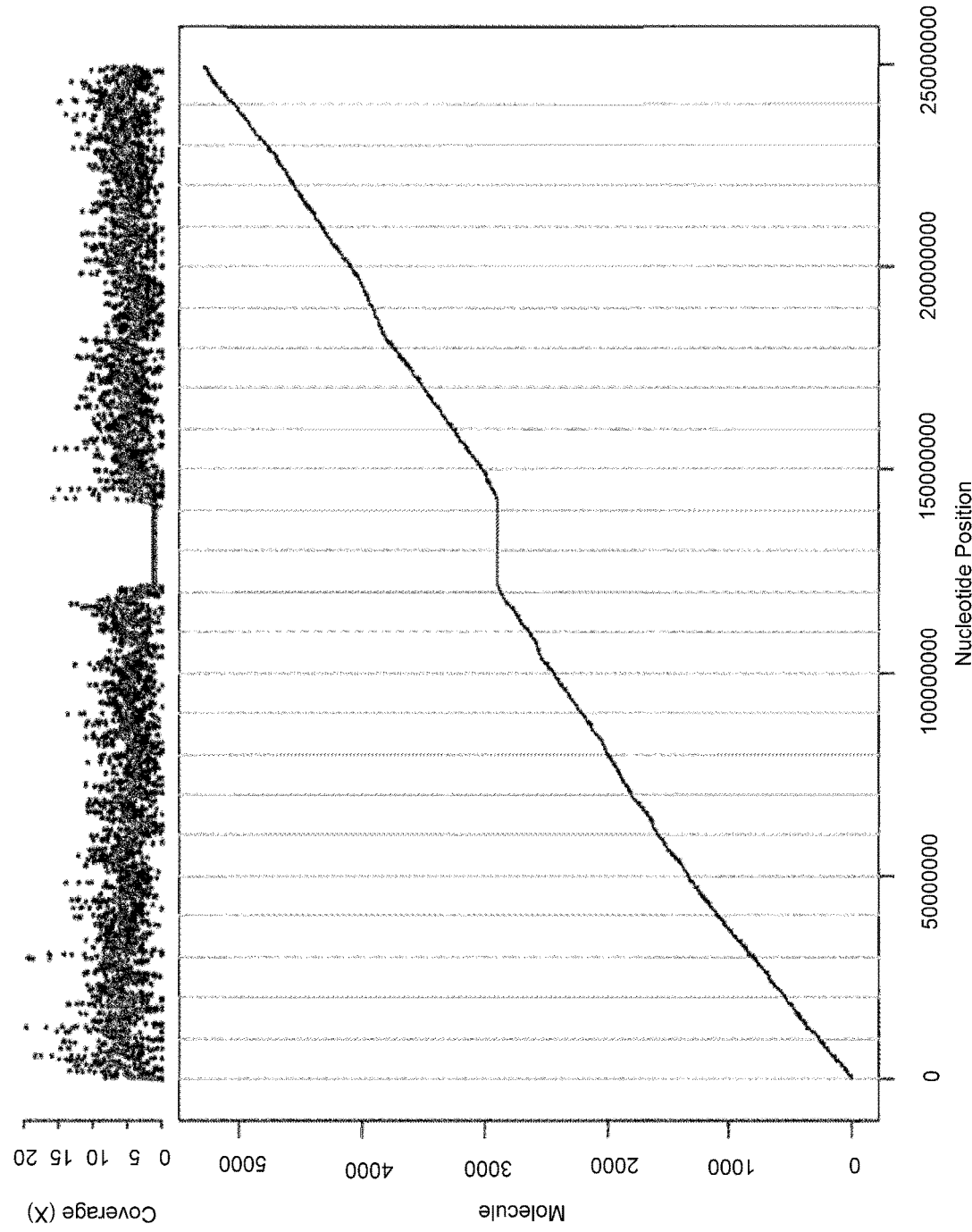
FIG. 7A is a graph illustrating diploid genomic fragments from a human male sample aligned to chromosome 1 in accordance with some embodiments herein. The y-axis provides the quantity of coverage. The x-axis provides the nucleotide position. The average coverage depth was 5X.

As shown in FIG. 7A, the average coverage depth observed for a diploid autosomal chromosome (chromosome 1) was 5X, and was evenly distributed across the chromosome. If the sampling of molecules had been even, the alignment start sites would have been randomly distributed across the chromosome, resulting in a linear plot.

Figure 7B:
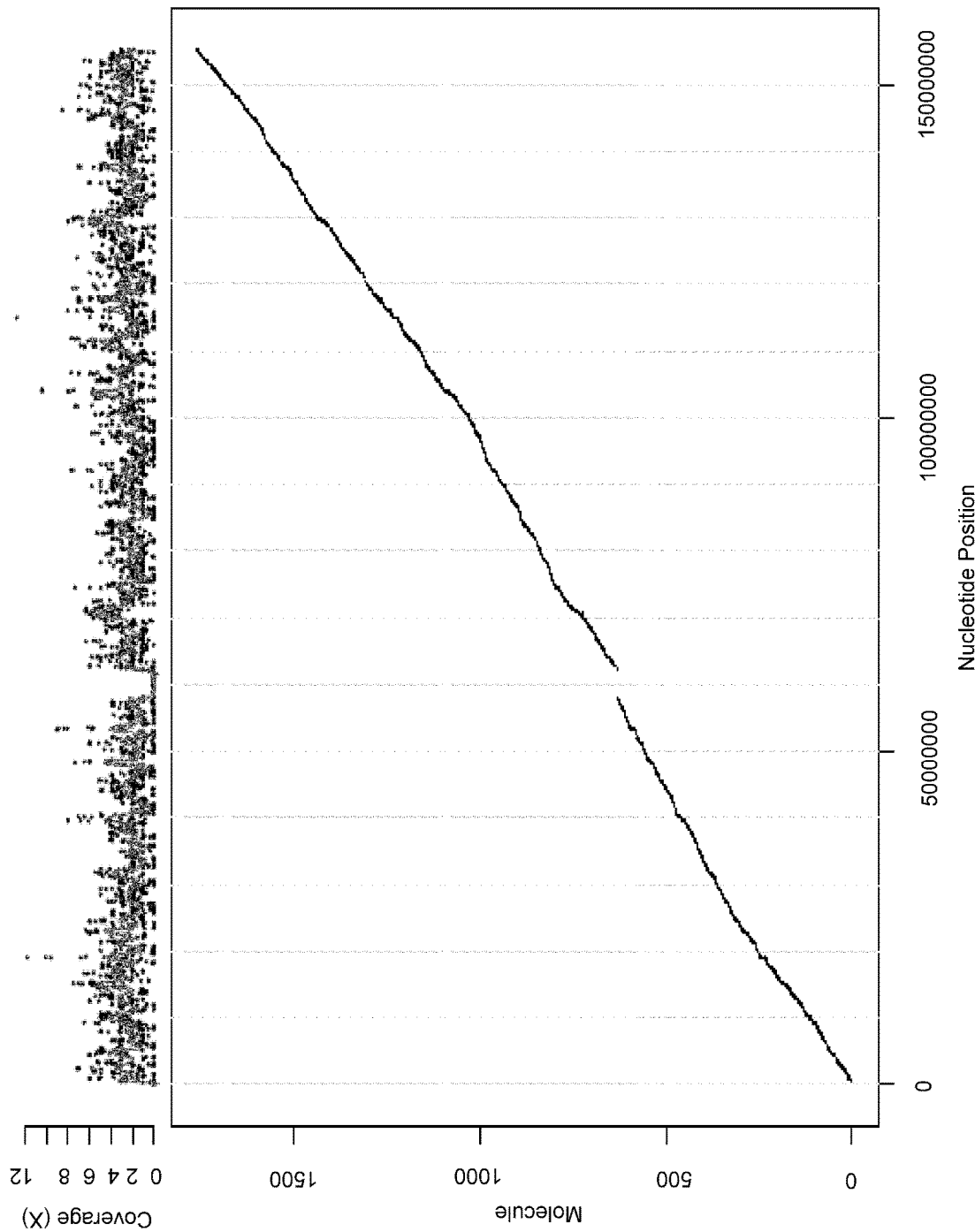
FIG. 7B is a graph showing a haploid sex chromosome X from the same male sample shown with an average coverage depth of 2X-2.5X (roughly half of the depth of diploid autosomes), demonstrating the quantitative measurement using the methods and platform according to some embodiments herein.
Figure 8:
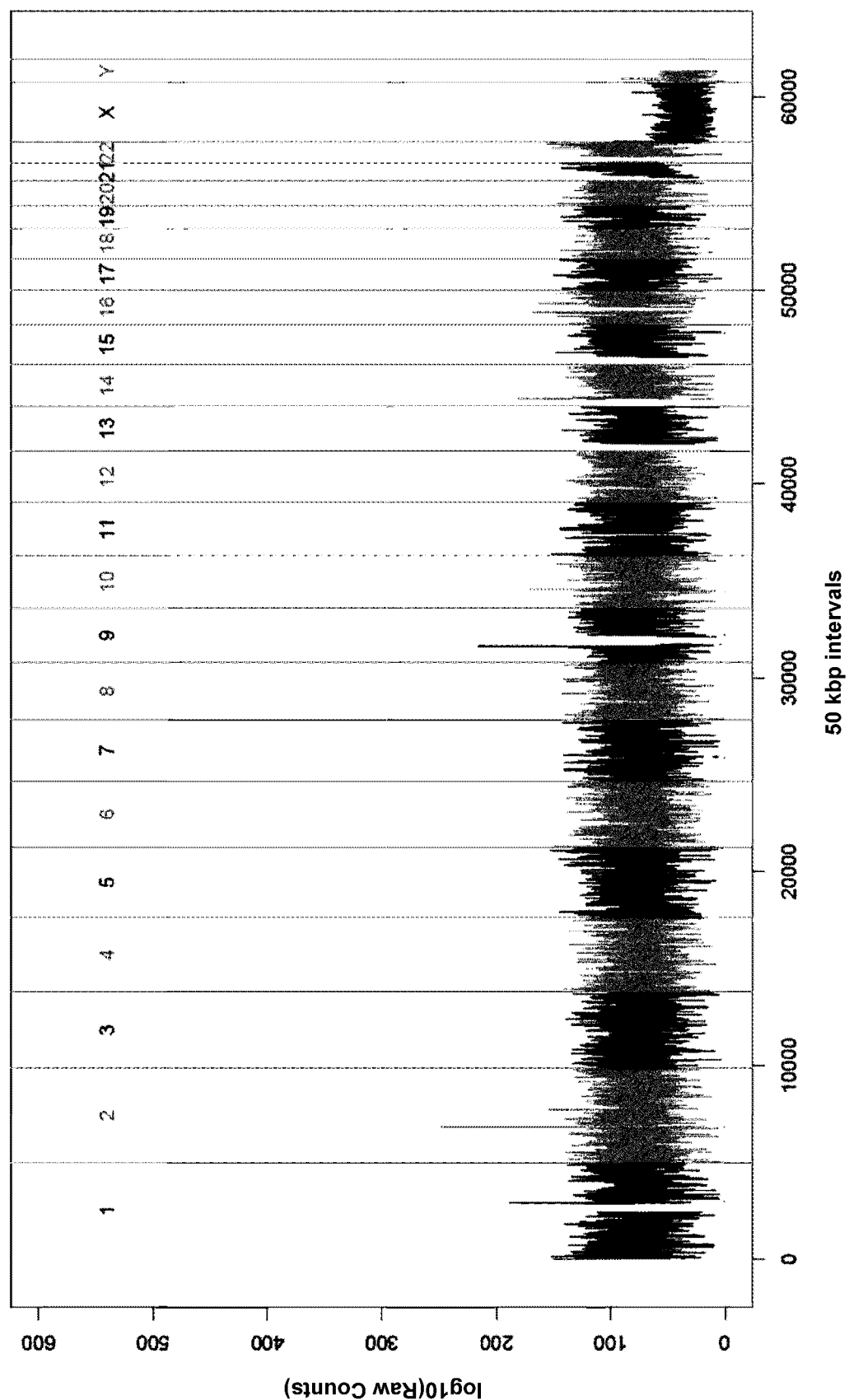
FIG. 8 is a graph illustrating an example of a raw read profile in a euploid male in accordance with some embodiments herein.
Figure 9:
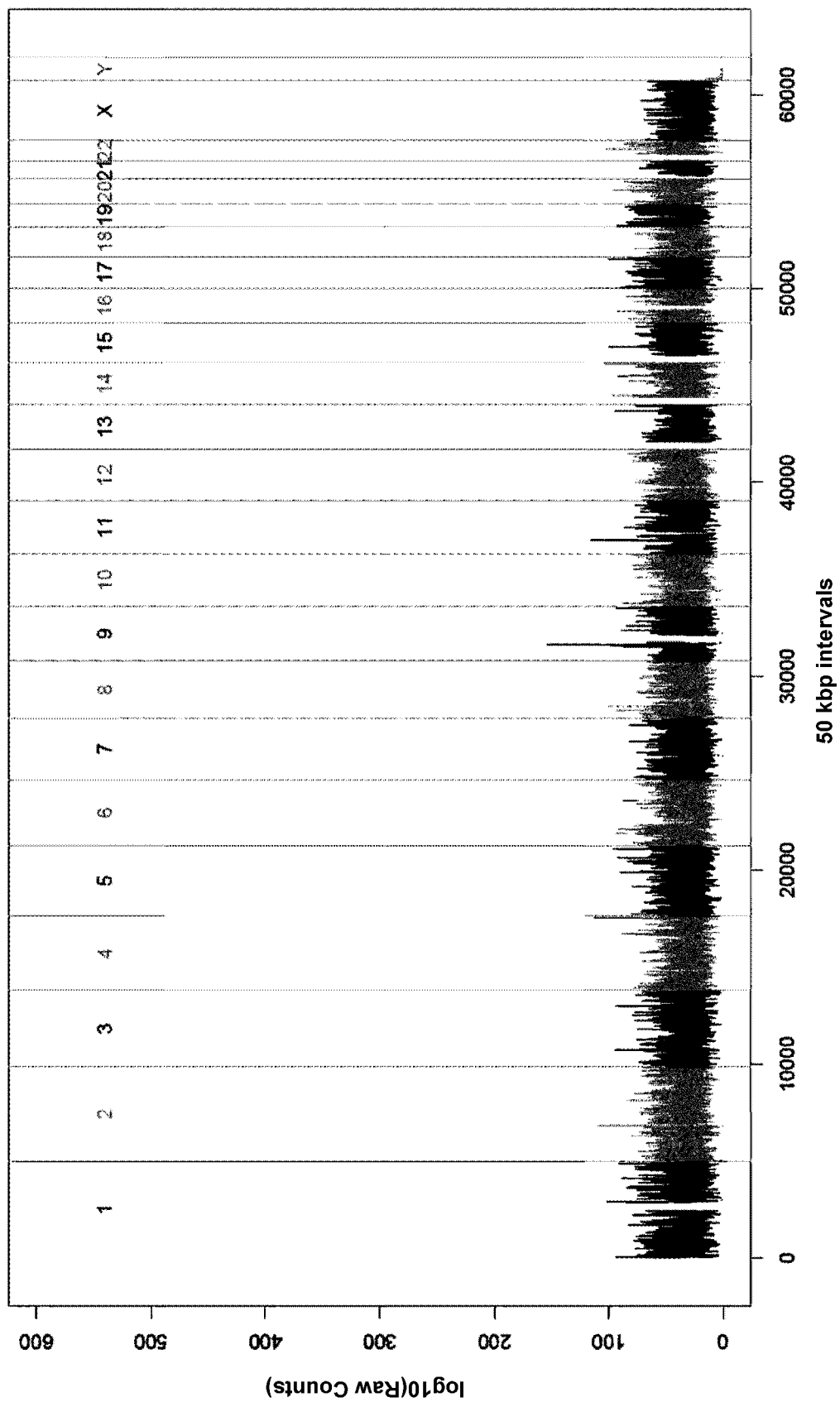
FIG. 9 is a graph illustrating an example of a raw read profile in a euploid female in accordance with some embodiments herein.
Figure 10:
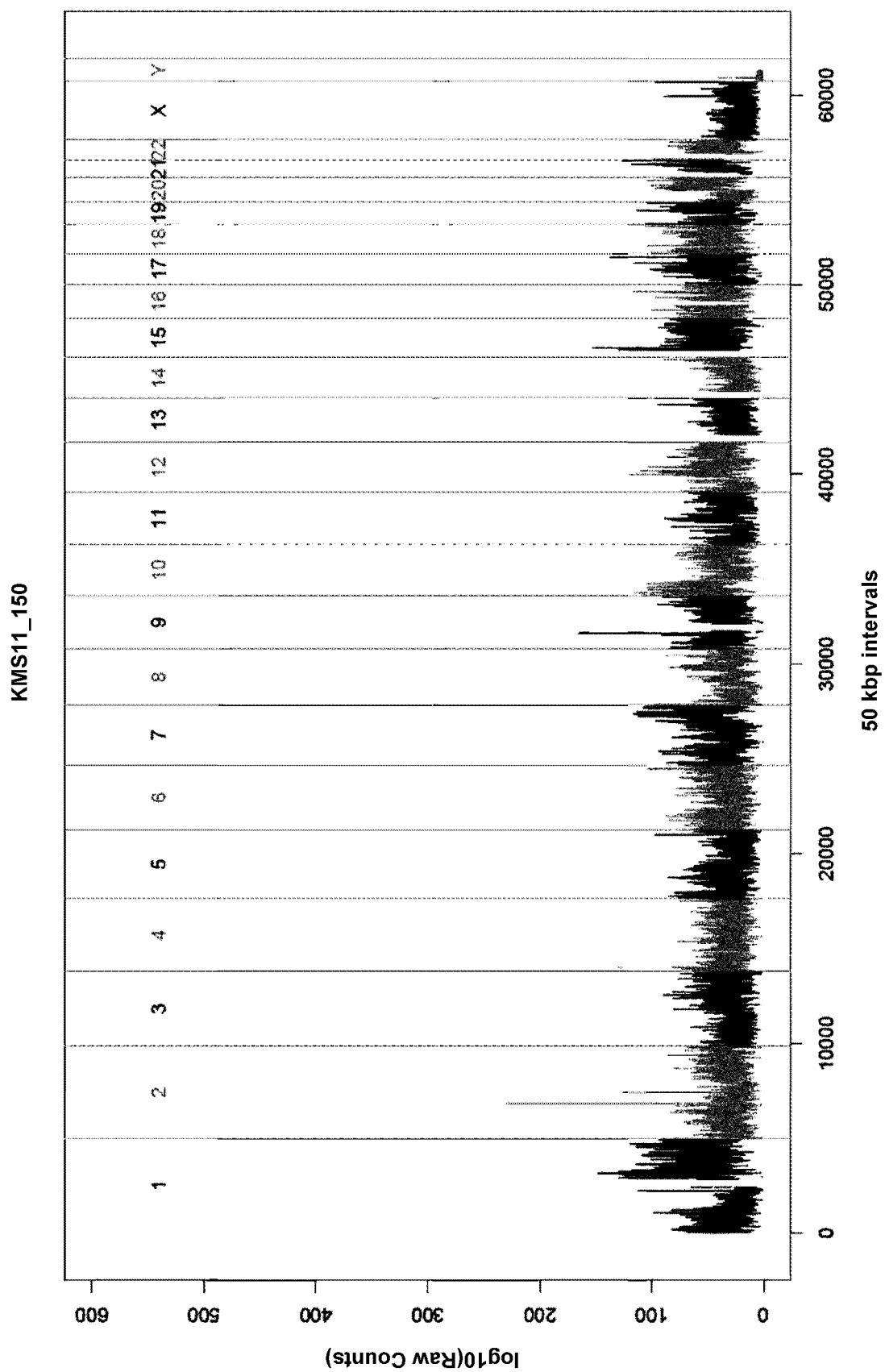
FIG. 10 is a graph illustrating an example of a raw read profile in a cancer sample in accordance with some embodiments herein.
Figure 11:
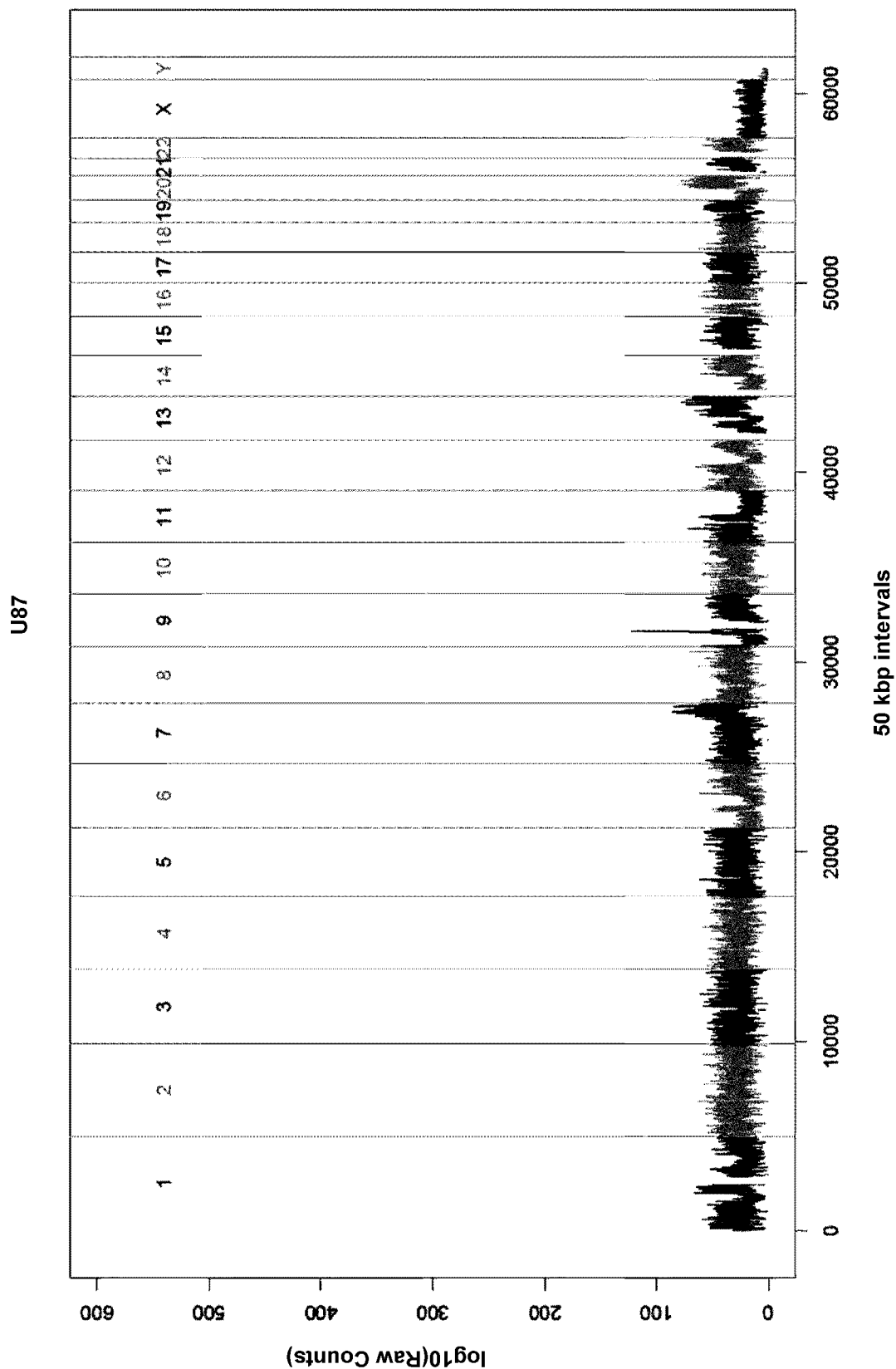
FIG. 11 is a graph illustrating an example of a raw read profile in another cancer sample in accordance with some embodiments herein.

As shown in FIG. 7B, the average coverage depth observed for a haploid sex chromosome (chromosome X) from the same male sample was 2X-2.5X (roughly half the depth of diploid autosomes), and was also evenly distributed across the chromosome. This example demonstrates the quantitative measurements that can be achieved using the methods and platform described herein.

Example 2

Figure 22:
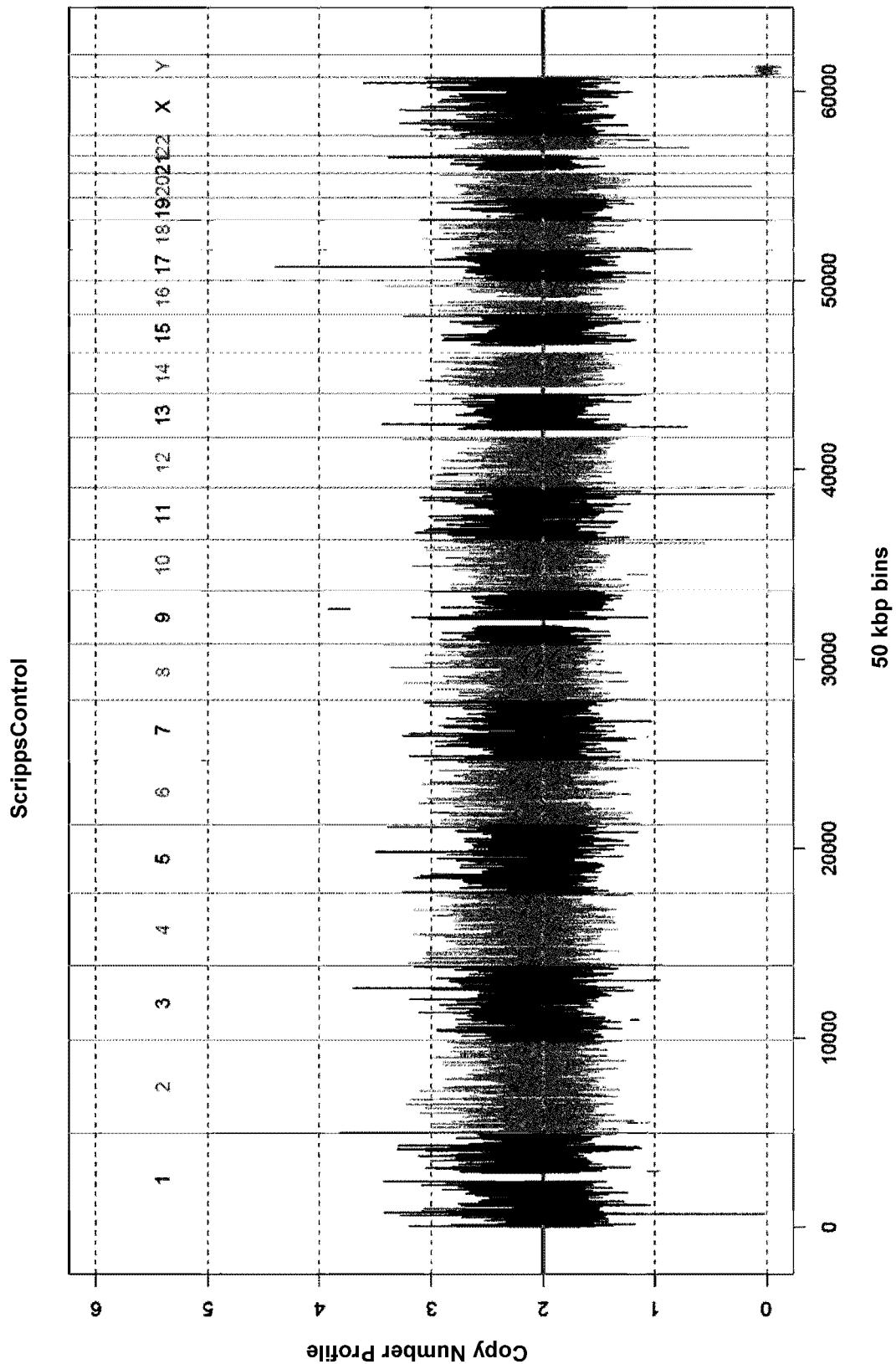
FIG. 22 is a graph illustrating an example of a copy-number profile in a euploid female in accordance with some embodiments herein. The presence of both X chromosomes and the absence of ChrY are evident.
Figure 23:
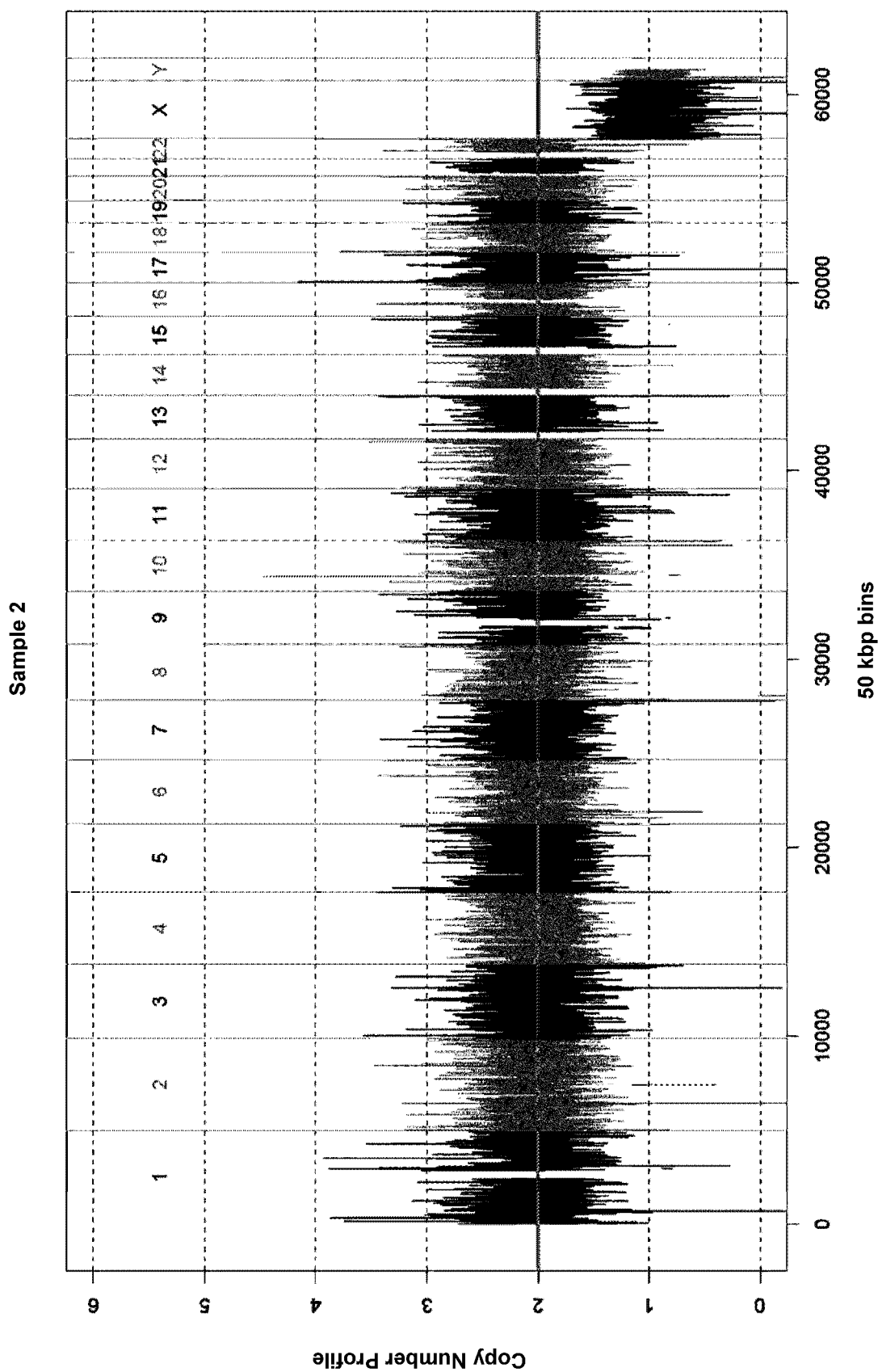
FIG. 23 is a graph illustrating an example of a copy number profile in a euploid male in accordance with some embodiments herein. The graph shows single copies of ChrX and ChrY.

The following values apply to an initial implementation of GROM, as applied to optical genome maps of human genomic polynucleotides optically labeled and analyzed using an Irys™ system (Bionano genomics). The initial implementation of GROM partitioned hg19 into 50,000 base pair intervals. Other reference genomes and other interval partitioning schemes can generate different numerical ranges. The total number of intervals is 61,927. The number of intervals per chromosome are as follows: Chr1: 4986, Chr2: 4864, Chr3: 3961, Chr4: 3824, Chr5: 3619, Chr6: 3423, Chr3: 3183, Chr8: 2928, Chr9: 2825, Chr10: 2711, Chr11: 2701, Chr12: 2678, Chr13: 2304, Chr14: 2147, Chr15: 2051, Chr16: 1808, Chr17: 1624, Chr18: 1562, Chr19: 1183, Chr20: 1261, Chr21: 963, Chr22: 1027, ChrX: 3106, ChrY: 1188. The number of intervals that survive interval filtering with relative error cutoff of 25% is 56,383. The number of labels per interval ranges from 0 to 26. The median number of labels per interval is 6, 4,803 intervals have no labels. The coverage values range from 10× to 600×. The observed LBDC values range from 0.0001 to 0.04. Interval parameter values: zero-order coefficients range from −0.07 to 4.3, gradients range from −30.8 to 77.0. Copy number profiles for euploid samples are centered at 2 (autosomes and ChrX in females; see, e.g. FIG. 22) or 1 (ChrX and ChrY in males, see, e.g. FIG. 23). The relative error in final copy number profiles ranged from 11% to ~20% for euploid samples (depending on coverage) (see FIG. 12). The relative error in copy number profiles generated for euploid samples decays with the coverage as reciprocal square root of the coverage, as expected. Cancer samples exhibit much higher relative error (observed up to 80%). Without being limited to any theory, the higher relative error rate in cancer sample is contemplated to result from biological variability.

Figure 12:
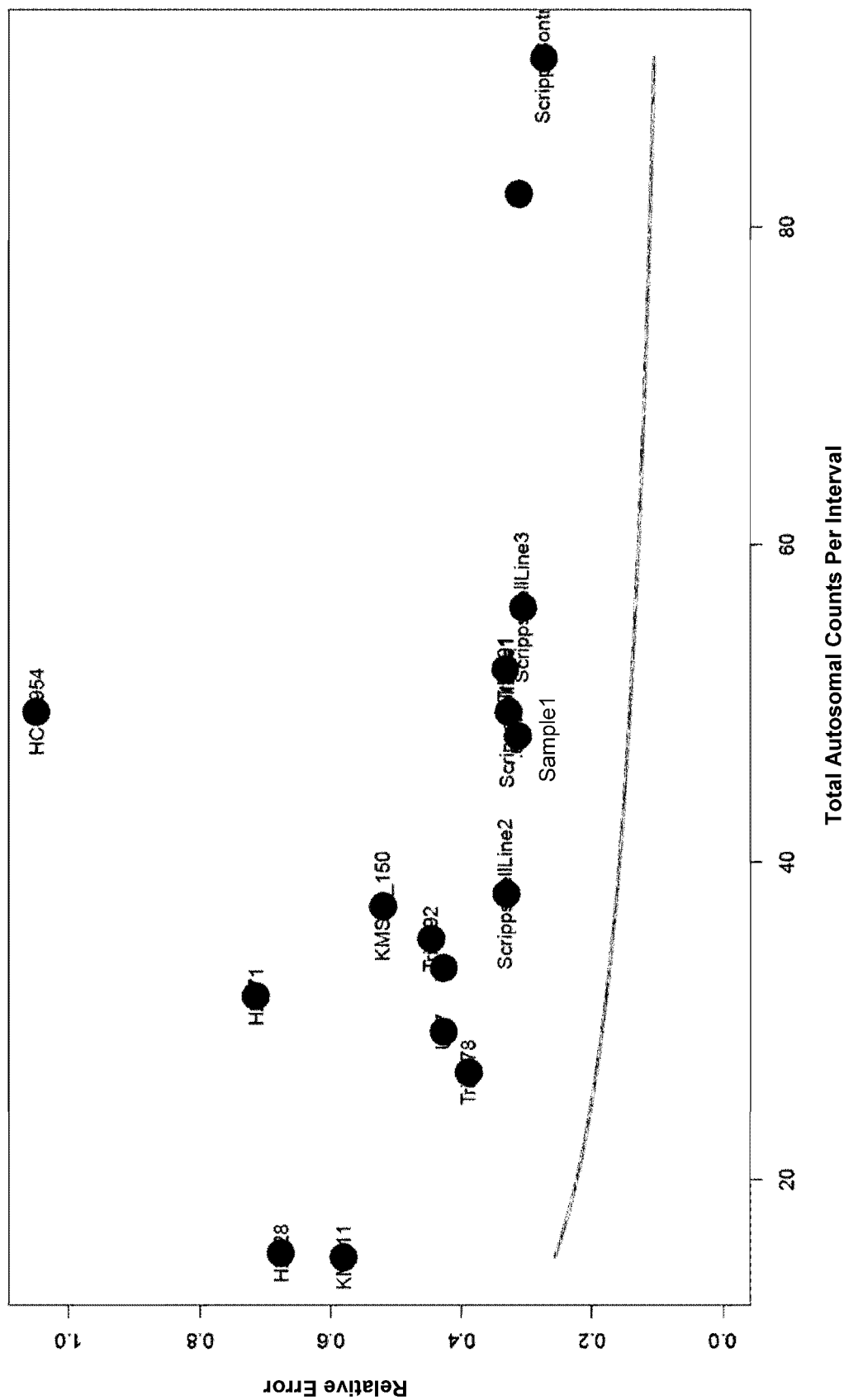
FIG. 12. is a graph illustrating the variance of raw coverage depth profiles (data points) and the expectation based on coverage (continuous line) in accordance with some embodiments herein. It is noted that the variance far exceeds the expectation based on coverage.
Figure 13:
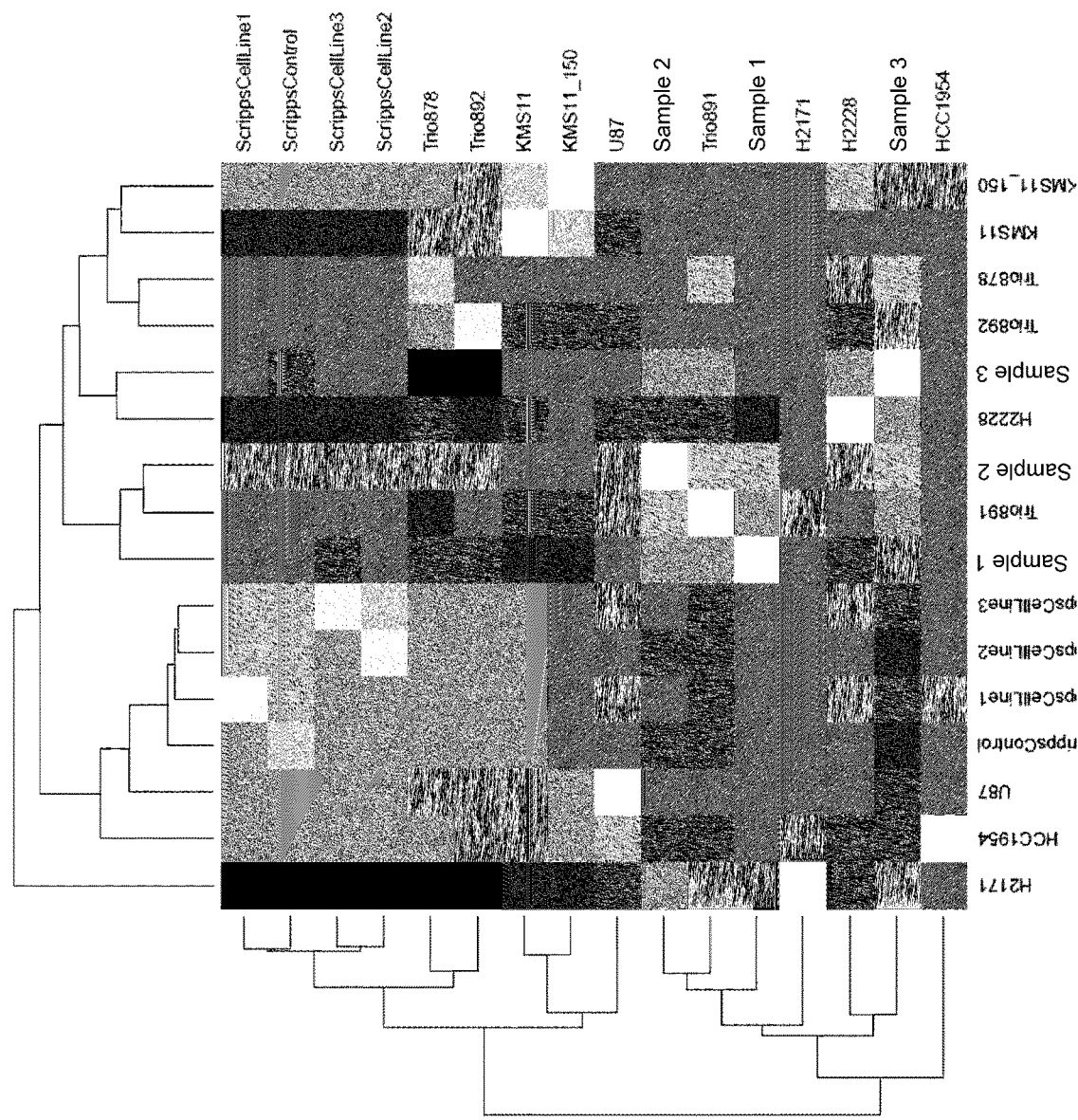
FIG. 13 is a heat map of quantized correlation coefficients derived from several raw coverage depth profiles in accordance with some embodiments herein. Hierarchical clustering of the correlation coefficients distinguishes male samples from female samples. Also shown is clustering, which groups together all technical replicates obtained on the biological material of the same origin. Cancer samples are clearly separated from all other samples.
Figure 14:
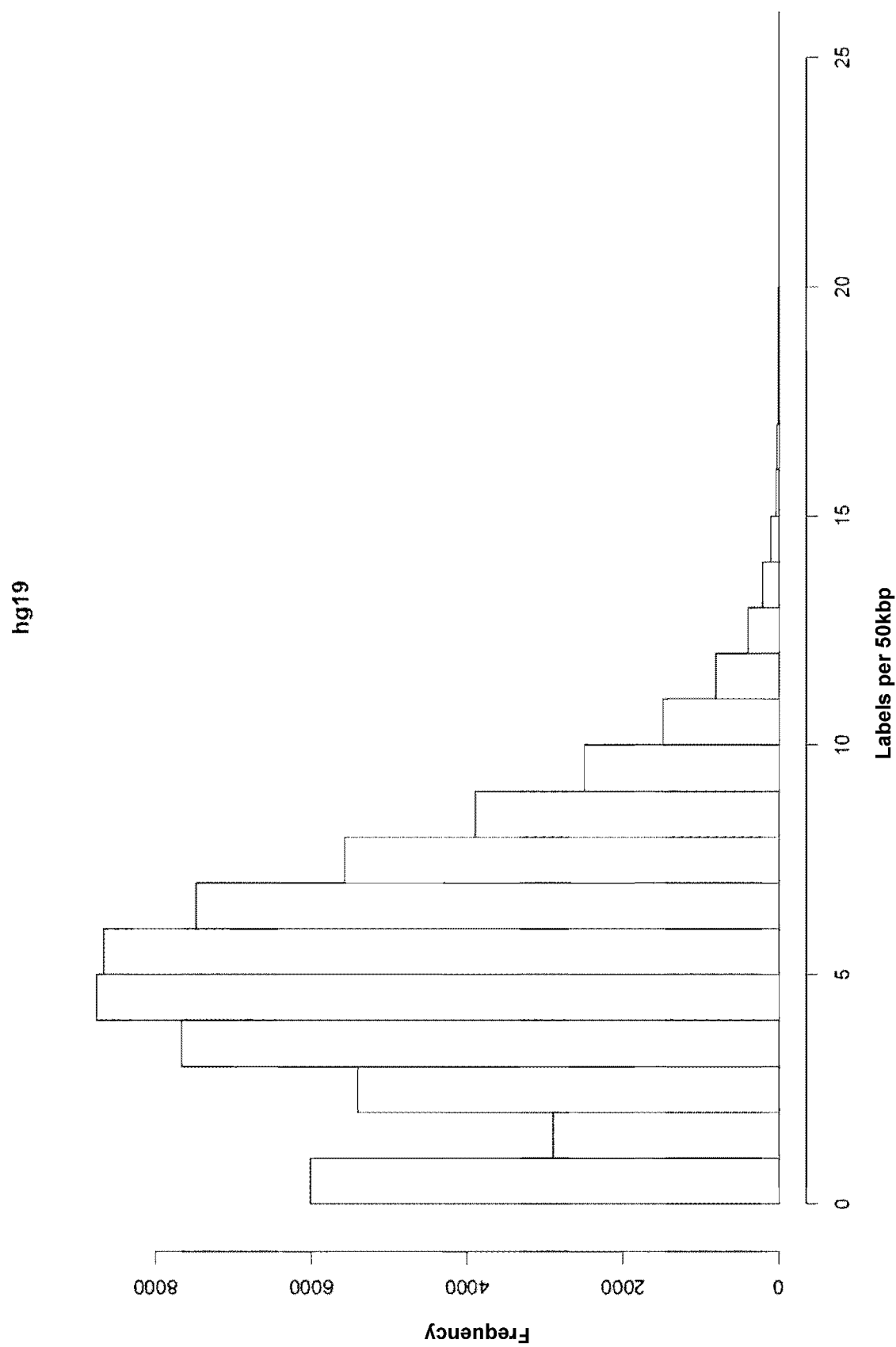
FIG. 14 is a bar graph depicting the number of labels per 50 kbp interval ranges from 0 to 26, with the median of 6, in accordance with some embodiments herein.
Figure 15:
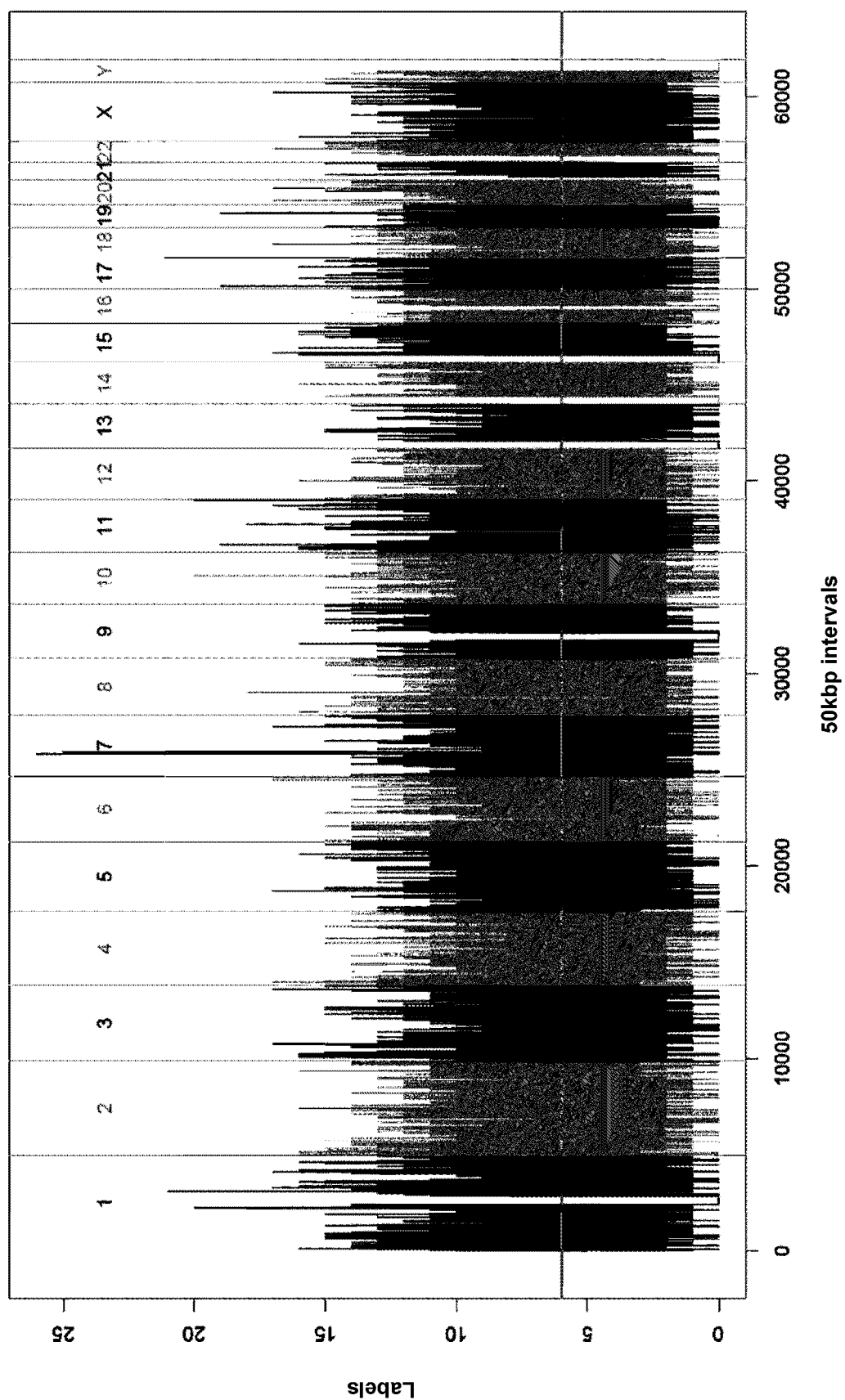
FIG. 15 is a graph illustrating the number of labels per interval as a function of the genomic location, in accordance with some embodiments herein.
Figure 16:
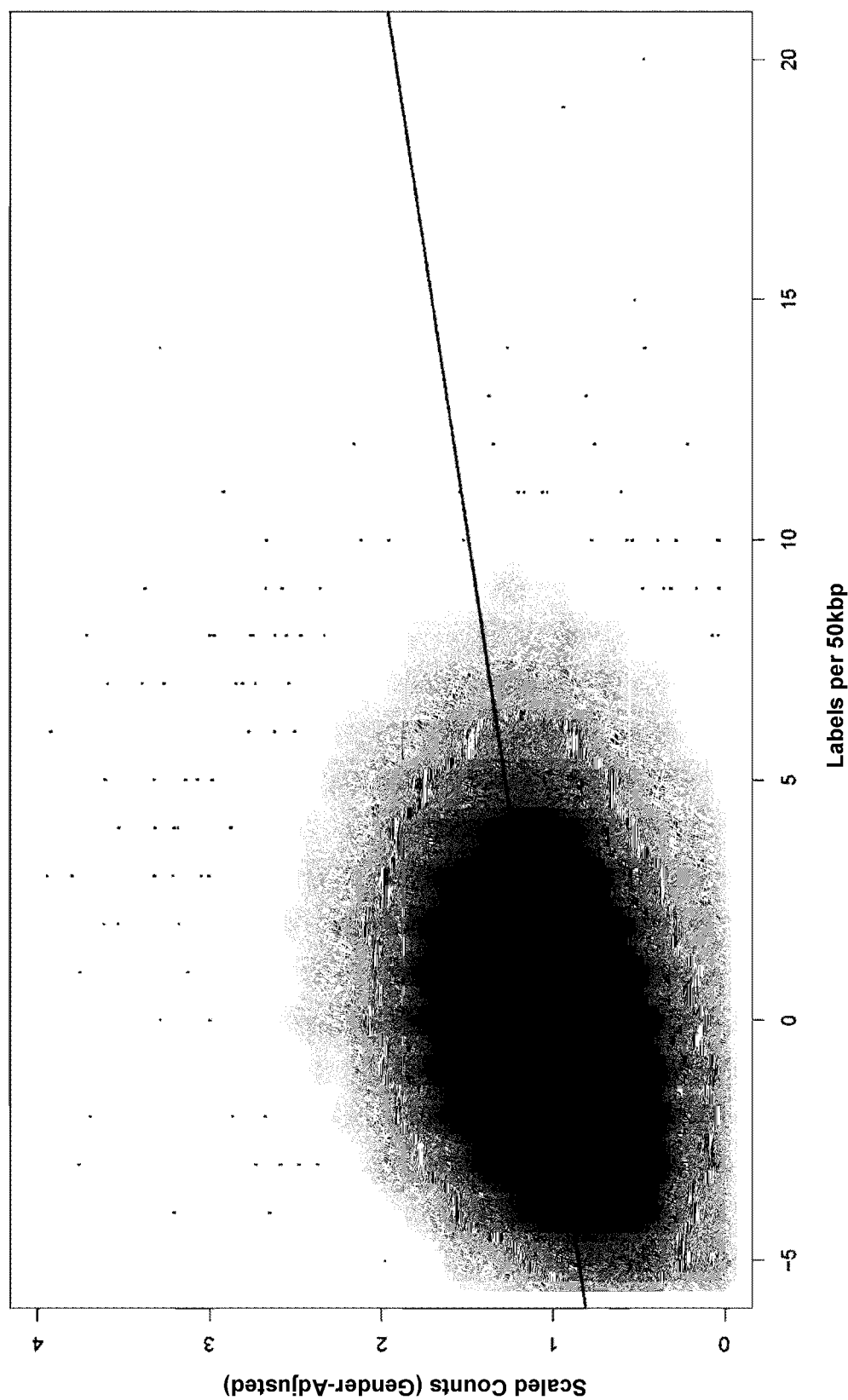
FIG. 16 is a graph illustrating a regression of scaled coverage depth vs. number of labels per interval yields Label Density Bias Coefficient (LBDC), evaluated as the gradient of the regression line in accordance with some embodiments herein. The number of labels per interval is shifted to the left by the median number of labels per interval (6).
Figure 17:
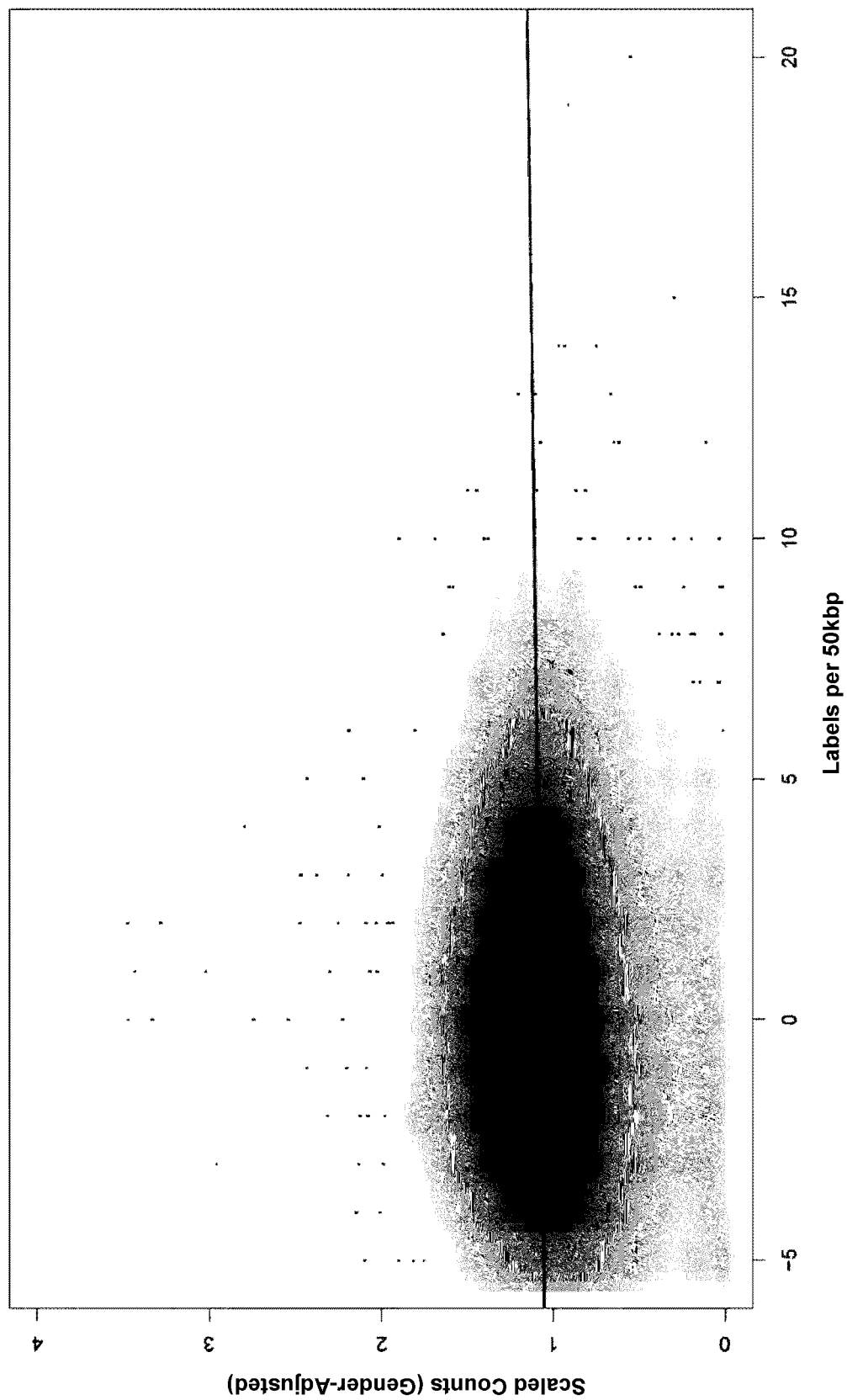
FIG. 17 is a graph illustrating that Label Density Bias Coefficient is sample-dependent in accordance with some embodiments herein. While the example in FIG. 9 shows a highly biased sample, this figure illustrates a bias-free sample.
Figure 18:
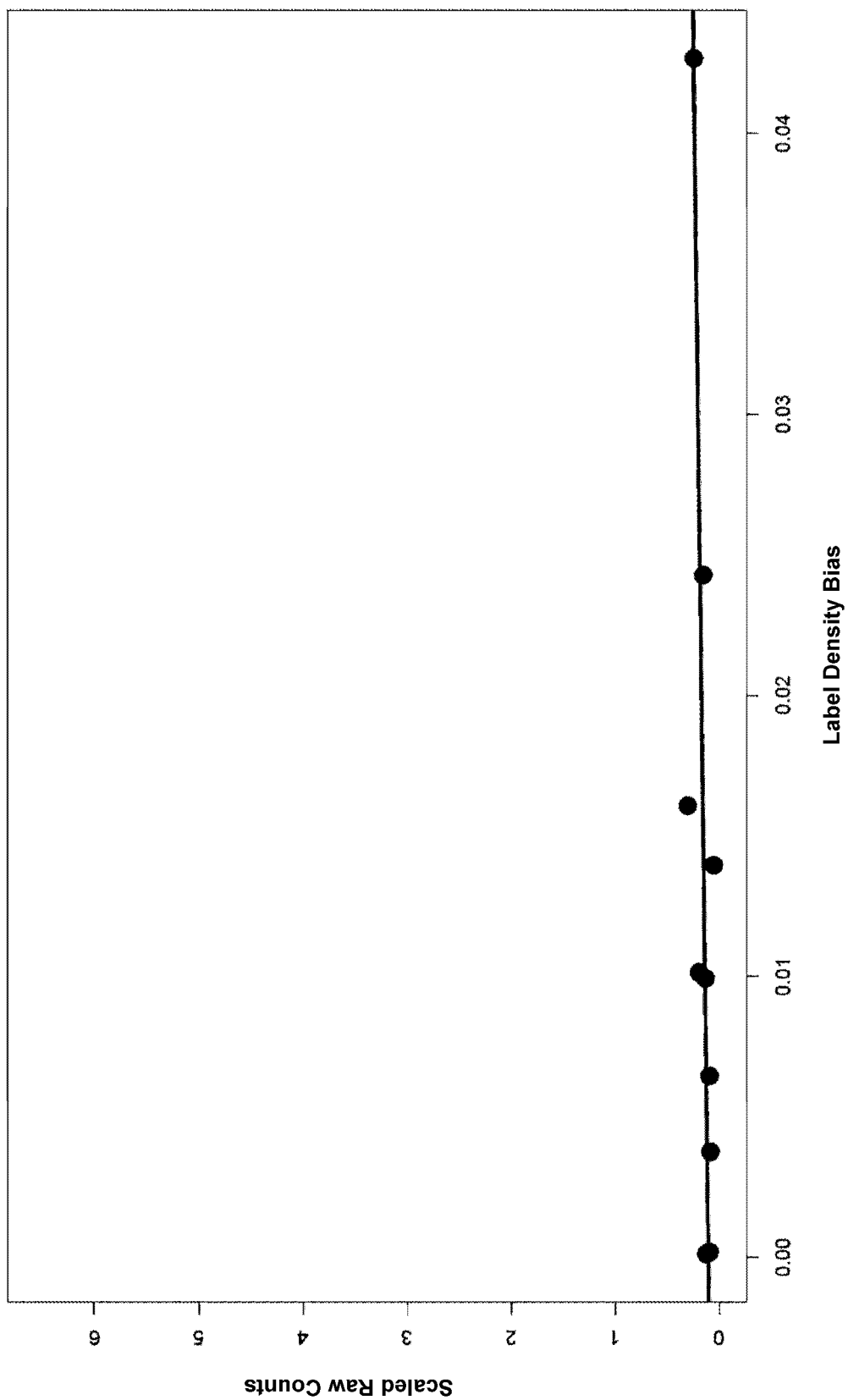
FIG. 18 is a graph illustrating the regression of scaled coverage depths within an interval versus sample-specific LDBC values for multiple samples yields two interval parameters (zero-order coefficient and gradient), as well as error measures (such as relative error).
Figure 19:
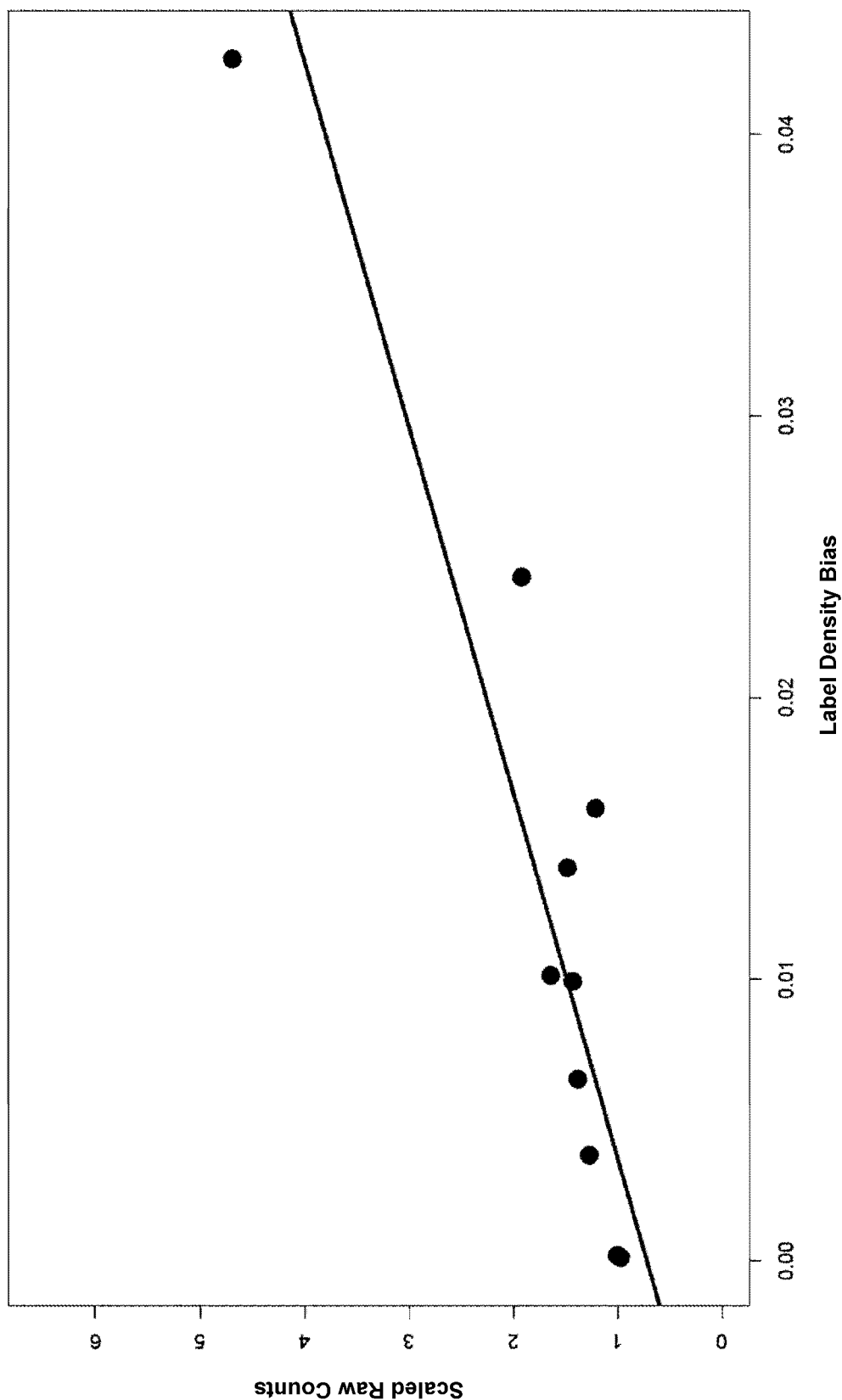
FIG. 19 is a graph illustrating that scaled coverage depths in some intervals, such as chr3_2697, show strong dependence on the sample-specific LDBC value, in accordance with some embodiments herein. As a rule, when the number of labels in an interval exceeds the median number of labels per interval, the associated gradient is high and positive.
Figure 20:
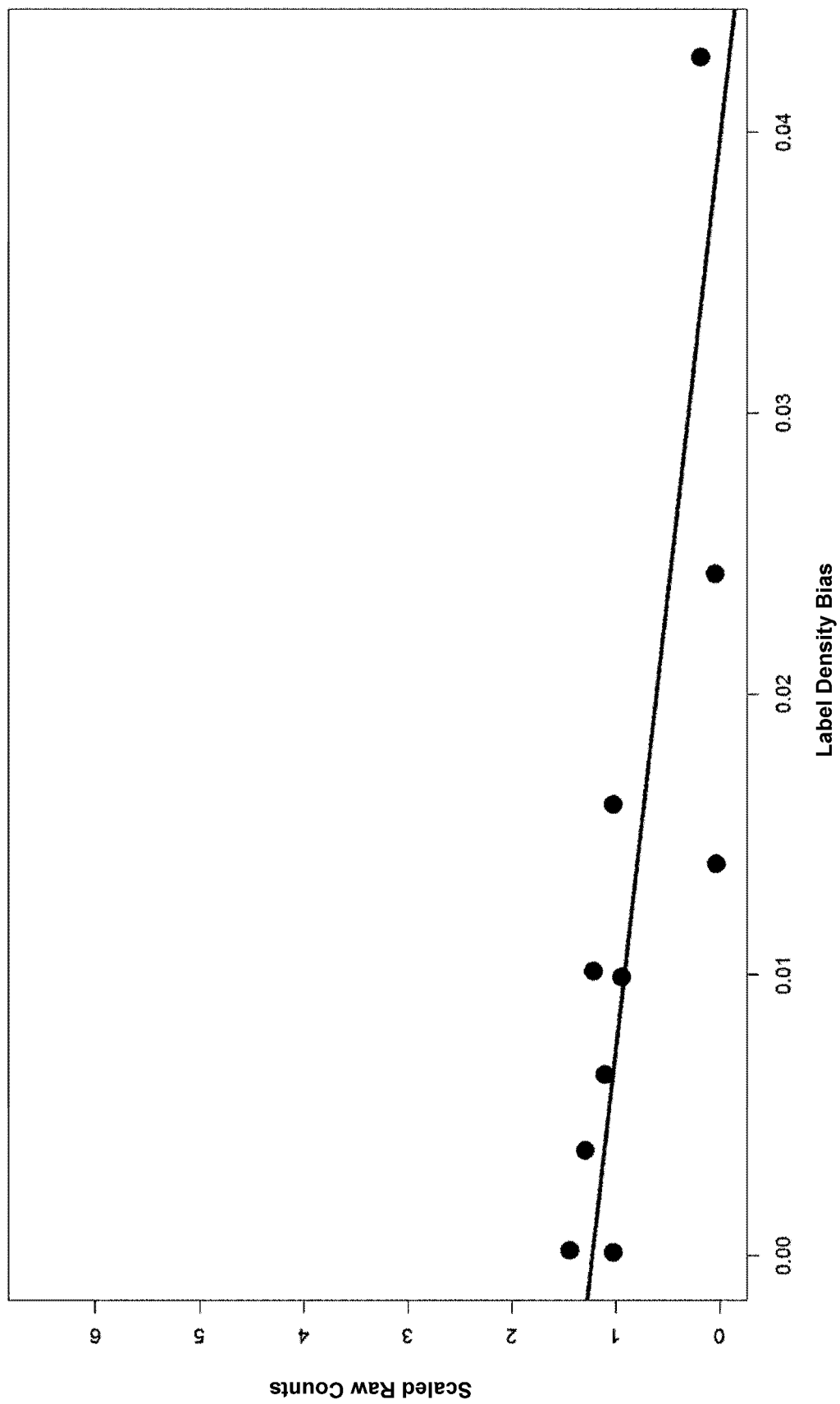
FIG. 20 is a graph illustrating that negative gradient is characteristic for intervals with few labels, in accordance with some embodiments herein.
Figure 21:
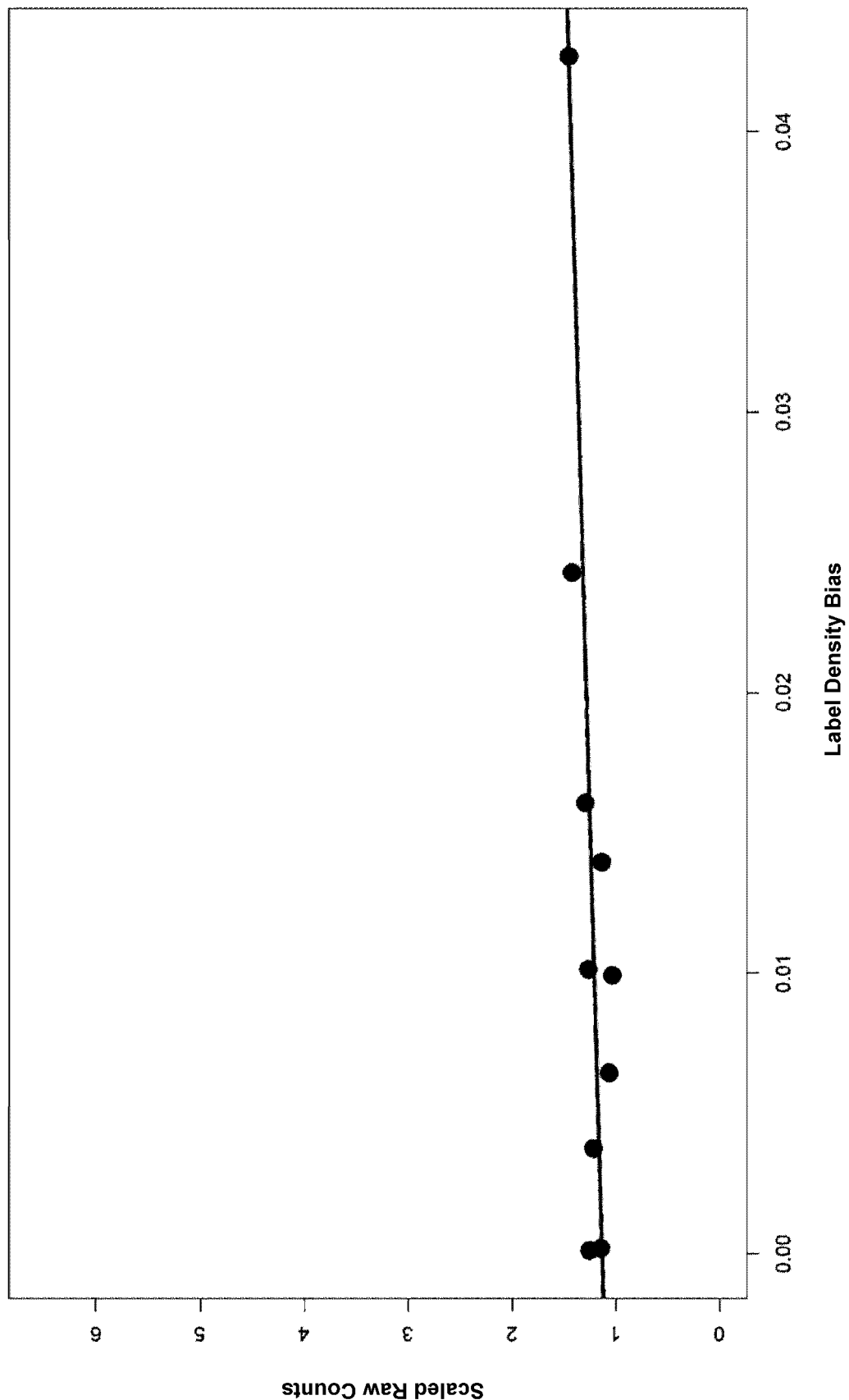
FIG. 21 is a graph illustrating that interval-specific gradient is close to zero when the number of labels is close to the median number of labels per interval, in accordance with some embodiments herein.
Figure 24:
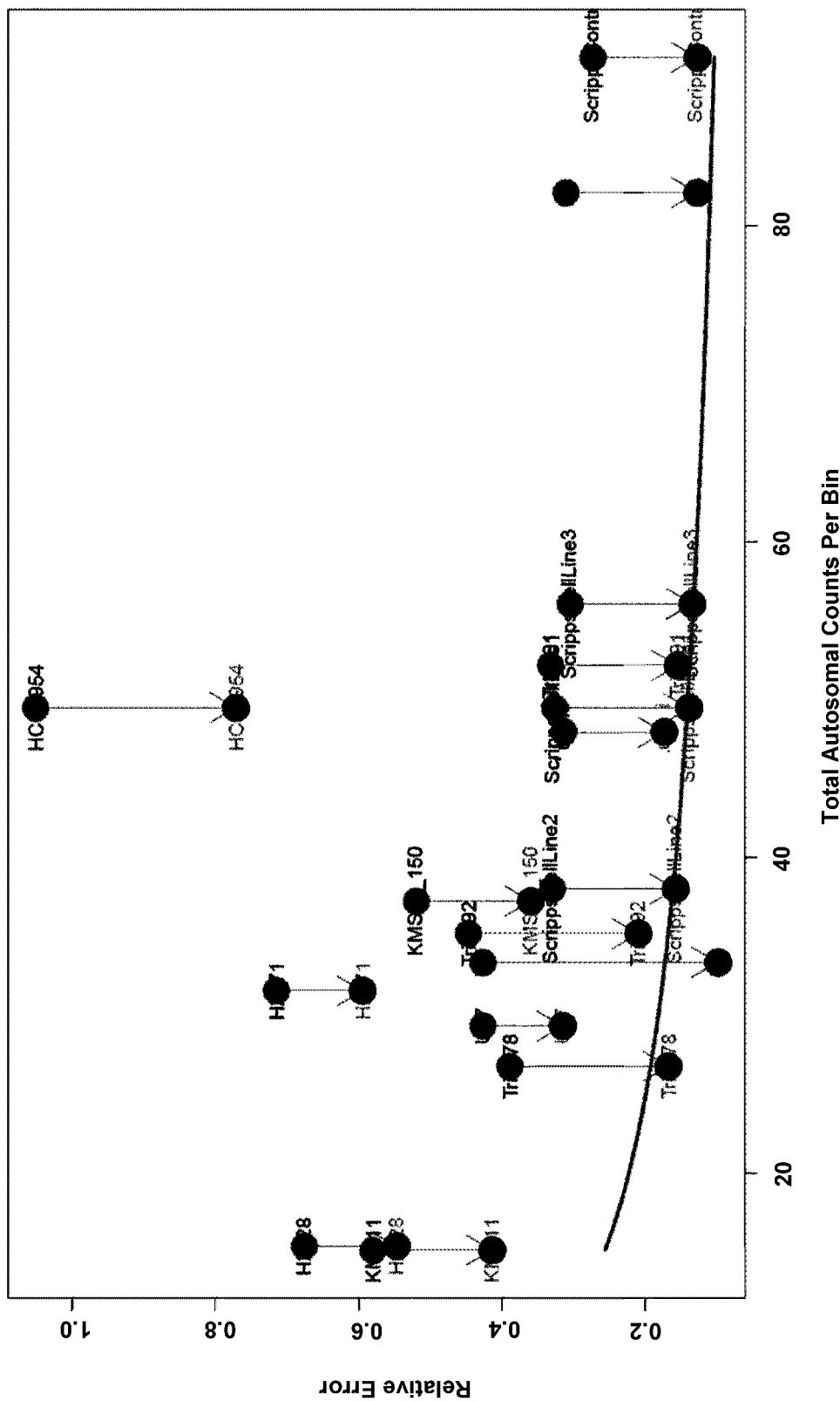
FIG. 24 is a graph illustrating that GROM reduces relative errors in euploid copy number profiles to approximately reciprocal square root of the coverage, in accordance with some embodiments herein. Cancer samples show high relative error due to biological variability.
Figure 25:
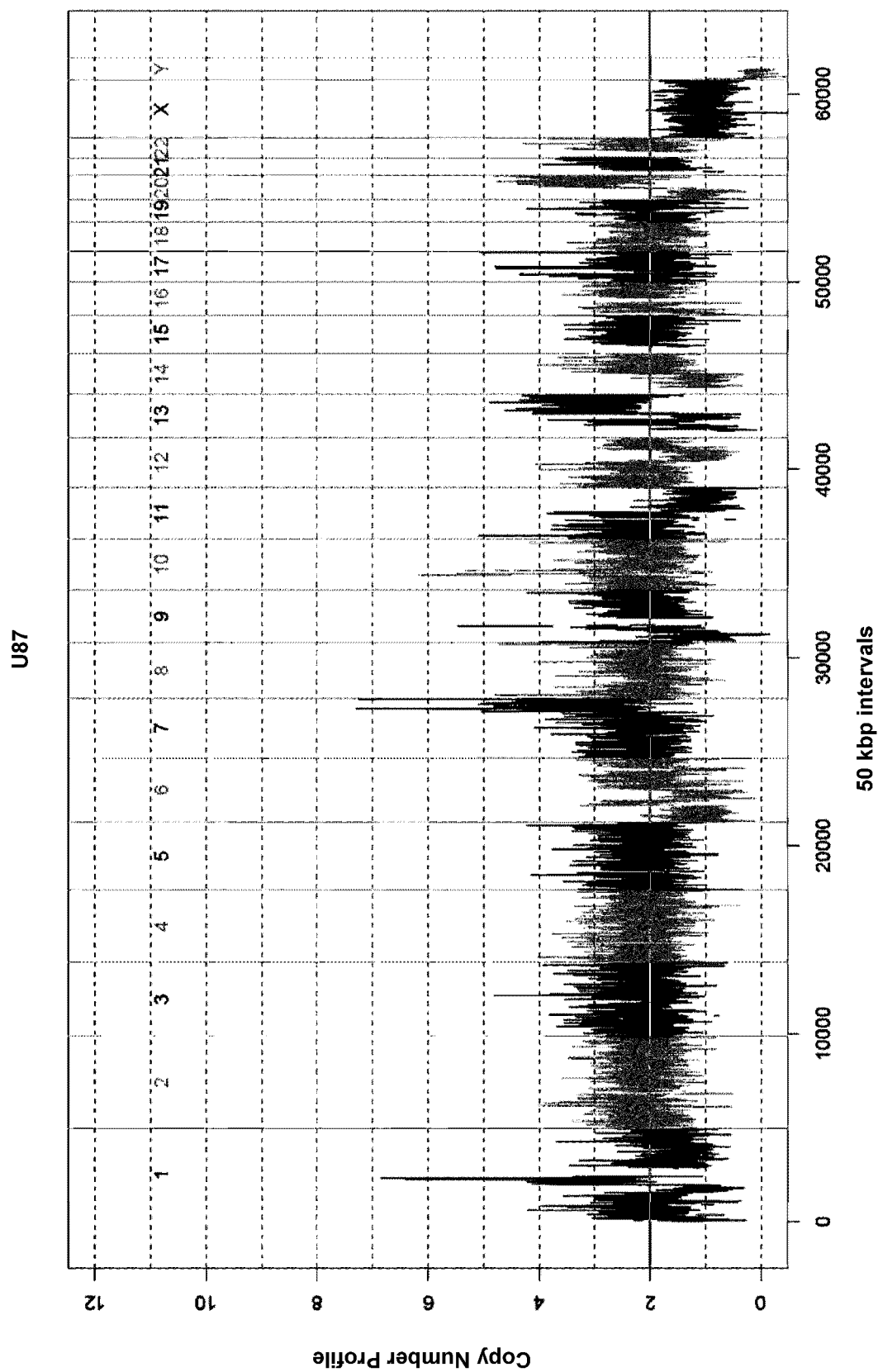
FIG. 25. is a graph illustrating an example of a copy number profile in a cancer sample in accordance with some embodiments herein.
Figure 26:
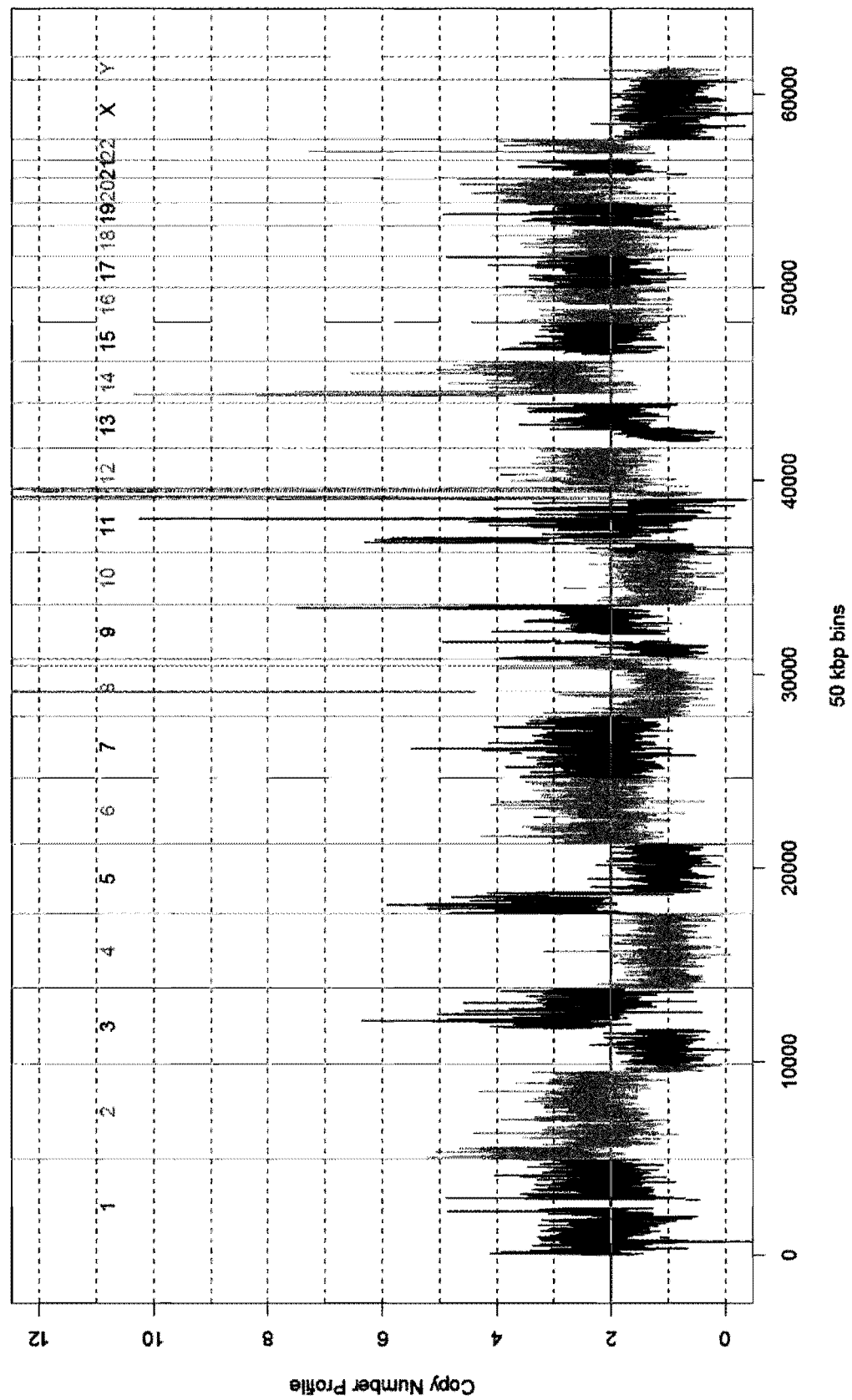
FIG. 26. is a graph illustrating an example of a copy number profile in a cancer sample in accordance with some embodiments herein.
Figure 27:
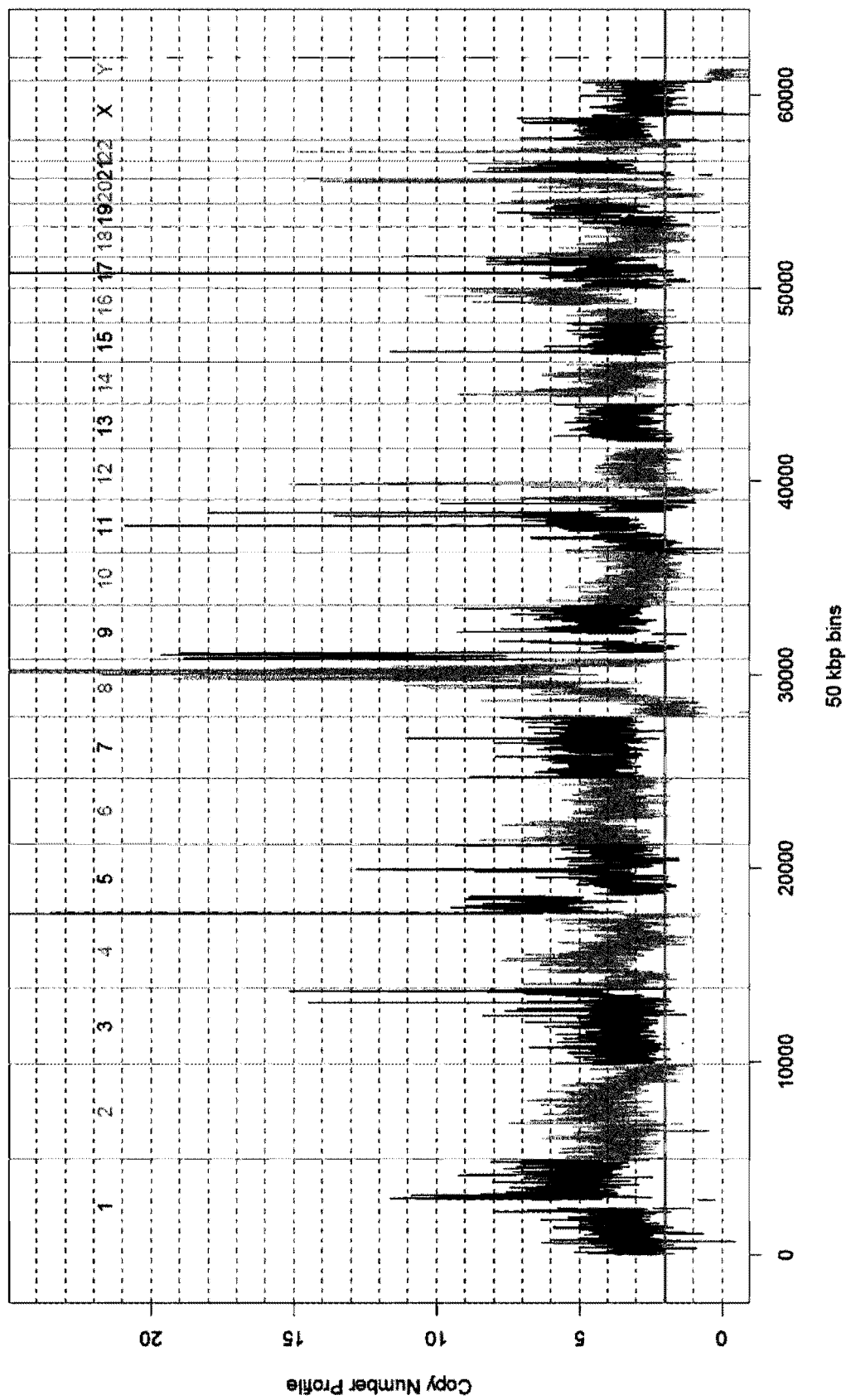
FIG. 27 is a graph illustrating an example of a copy number profile in a cancer sample in accordance with some embodiments herein.
Figure 28:
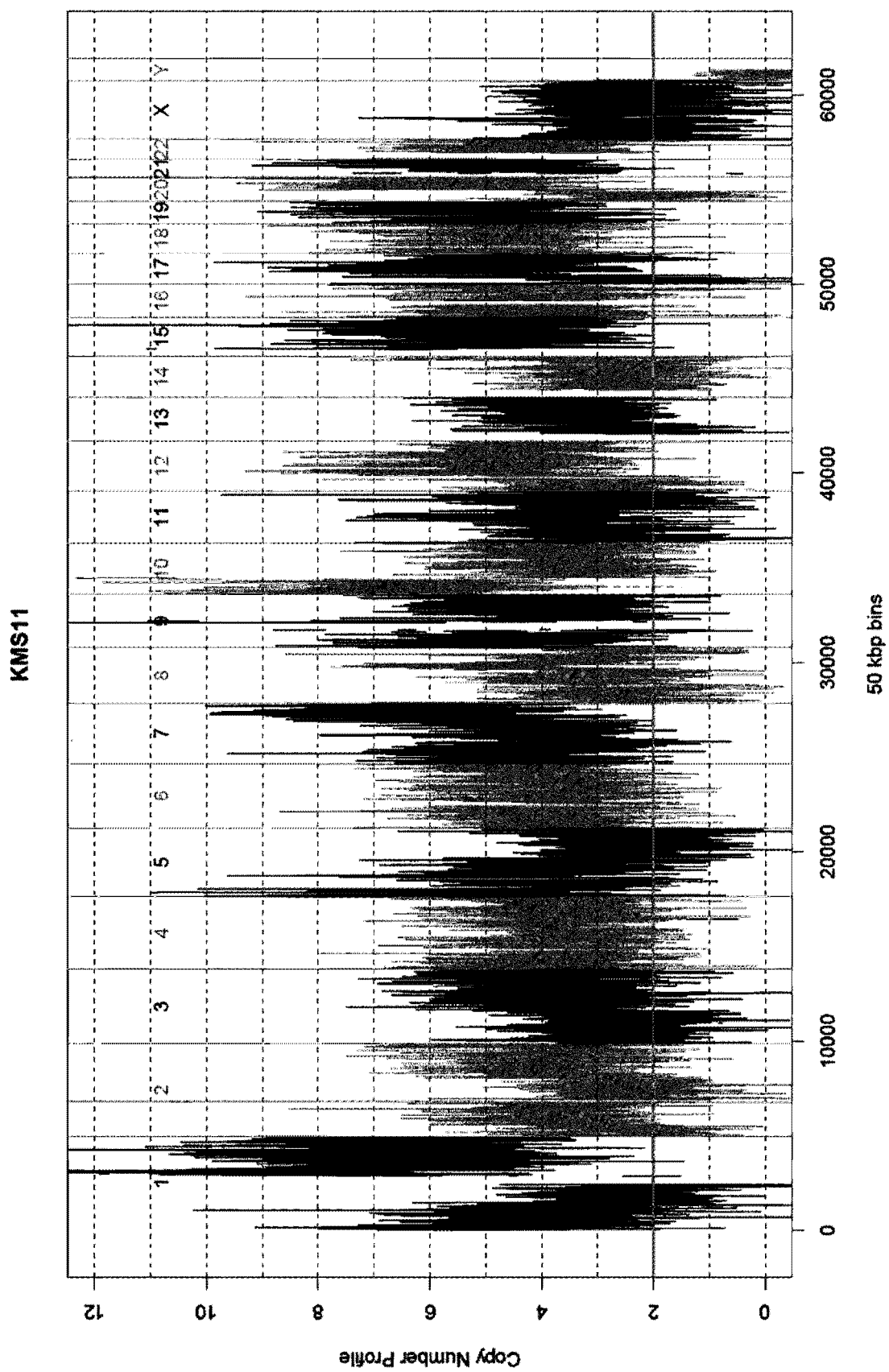
FIG. 28 is a graph illustrating an example of a copy number profile in a cancer sample in accordance with some embodiments herein.

Data from the implementation of GROM is shown in FIGS. 8-29. Raw reads were obtained (see, e.g. FIGS. 8-11). As shown in FIG. 12, the variance of raw coverage depth profiles (data points) far exceeded the expectation based on coverage (continuous line). Interval-wise correlation coefficients derived from several raw coverage depth profiles were compared, as shown in FIG. 13. Hierarchical clustering of the correlation coefficients distinguishes male samples from female samples. The clustering groups together all technical replicates obtained on the biological material of the same origin. Cancer samples are clearly separated from all other samples. The number of labels per interval are illustrated in FIGS. 14-15. Regressions were generated of scaled coverage depth vs. number of labels per interval yields Label Density Bias Coefficient (LBDC), evaluated as the gradient of the regression line. The number of labels per interval was shifted to the left by the median number of labels per interval. As shown in FIGS. 16-17, the Label Density Bias Coefficient is sample-dependent. While the example in FIG. 16 shows a highly biased sample, FIG. 17 illustrates a bias-free sample. The regression of scaled coverage depths within an interval vs. sample-specific LDBC values for multiple samples yielded two interval parameters (zero-order coefficient and gradient), as well as error measures (such as relative error; see FIG. 18). Scaled coverage depth in some intervals, such as chr3_2697, show strong dependence on the sample-specific LDBC value. Typically, when the number of labels in an interval exceeds the median number of labels per interval, the associated gradient is high and positive (see, e.g. FIG. 19). On the other hand, negative gradient is characteristic for intervals with few labels (see, e.g. FIG. 20). As shown in FIG. 21, interval-specific gradient is close to zero when the number of labels is close to the median number of labels per interval. GROM was implemented using the steps described in Table 1. As shown in FIG. 24, GROM reduces relative errors in euploid copy number profiles to approximately reciprocal square root of the coverage. Cancer samples show high relative error due to biological variability.

Figure 29:
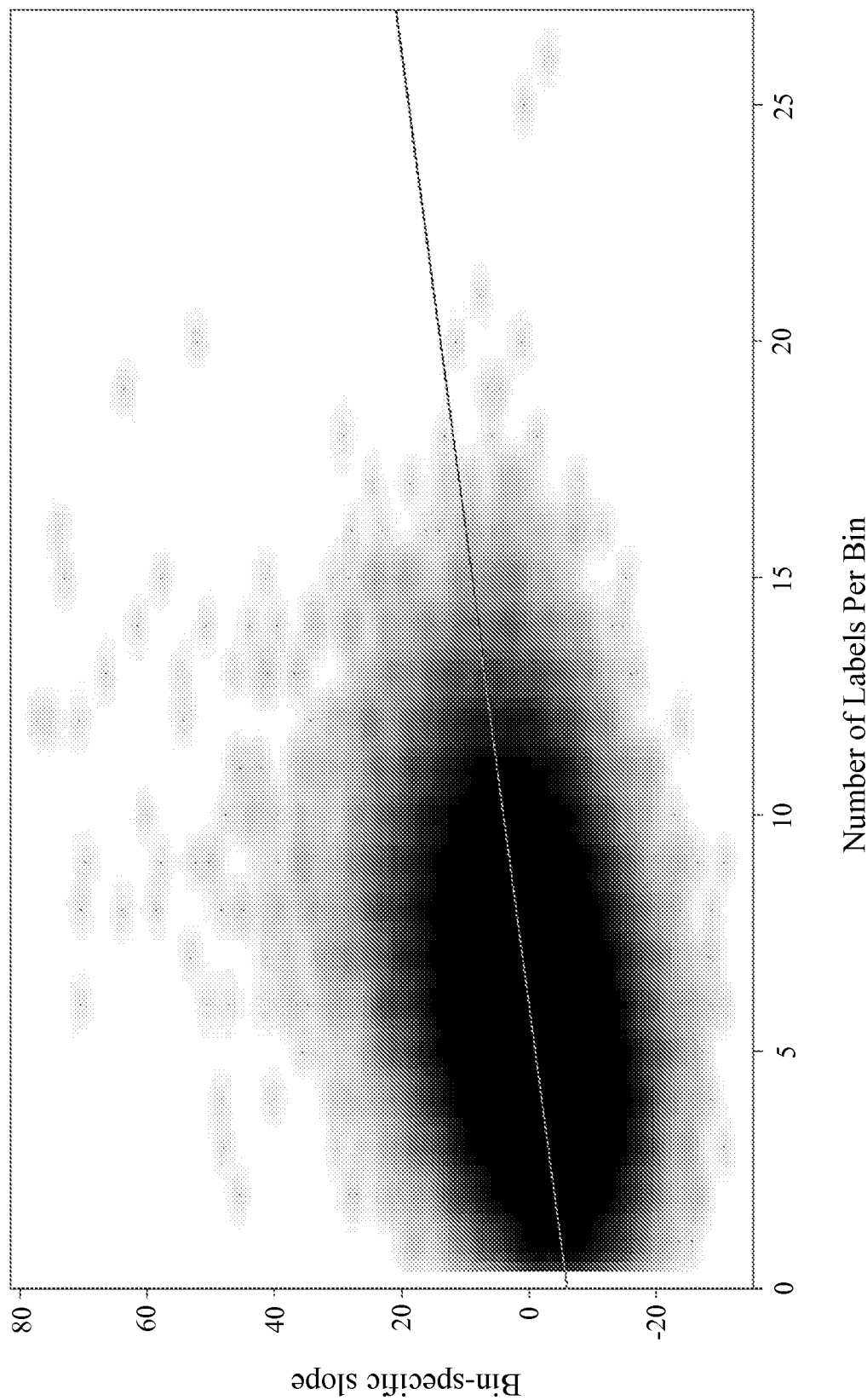
FIG. 29 is a graph illustrating that in accordance with some embodiments herein, gradient per interval varies linearly with the number of labels per interval, with a slope of 1 and the intercept equal to the median number of labels per interval. The regression line is almost indistinguishable from the ideally expected linear trend.

Exemplary copy number profiles obtained from cancer samples are shown in FIGS. 25-28. As shown in FIG. 29, gradient per interval varies linearly with the number of labels per interval, with a gradient of 1 and the zero-order coefficient equal to the median number of labels per interval. The regression line is almost indistinguishable from the ideally expected linear trend.

Example 3

Figure 31:
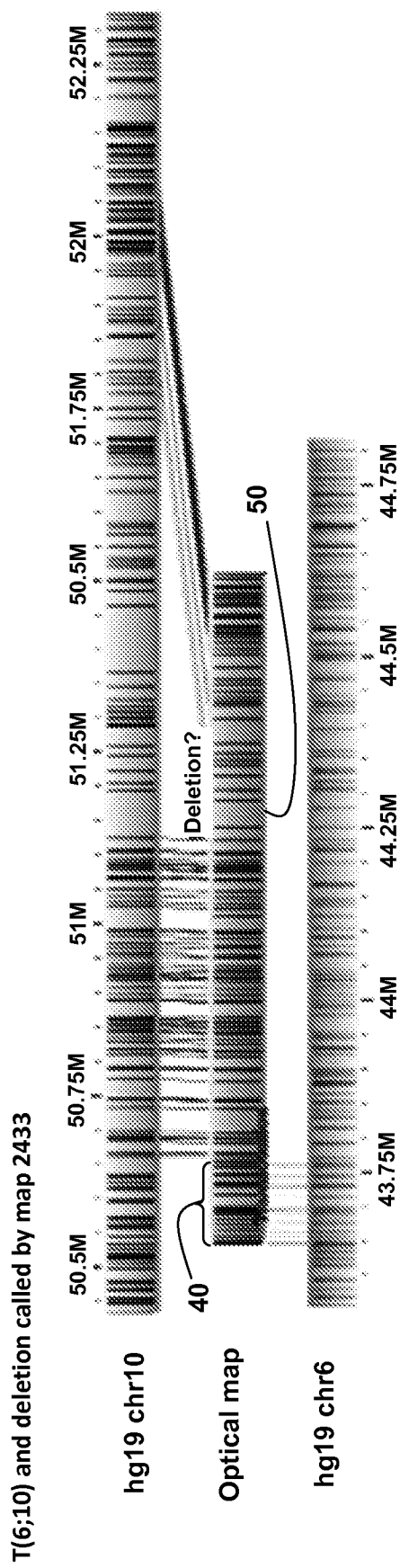
FIG. 31 is a schematic diagram illustrating a translocation 40 involving chromosomes 6 and 10, corresponding to vertical line 21 from FIG. 30B in accordance with some embodiments herein. Also shown is an apparent deletion 50 of a region of chromosome 10.
Figure 32:
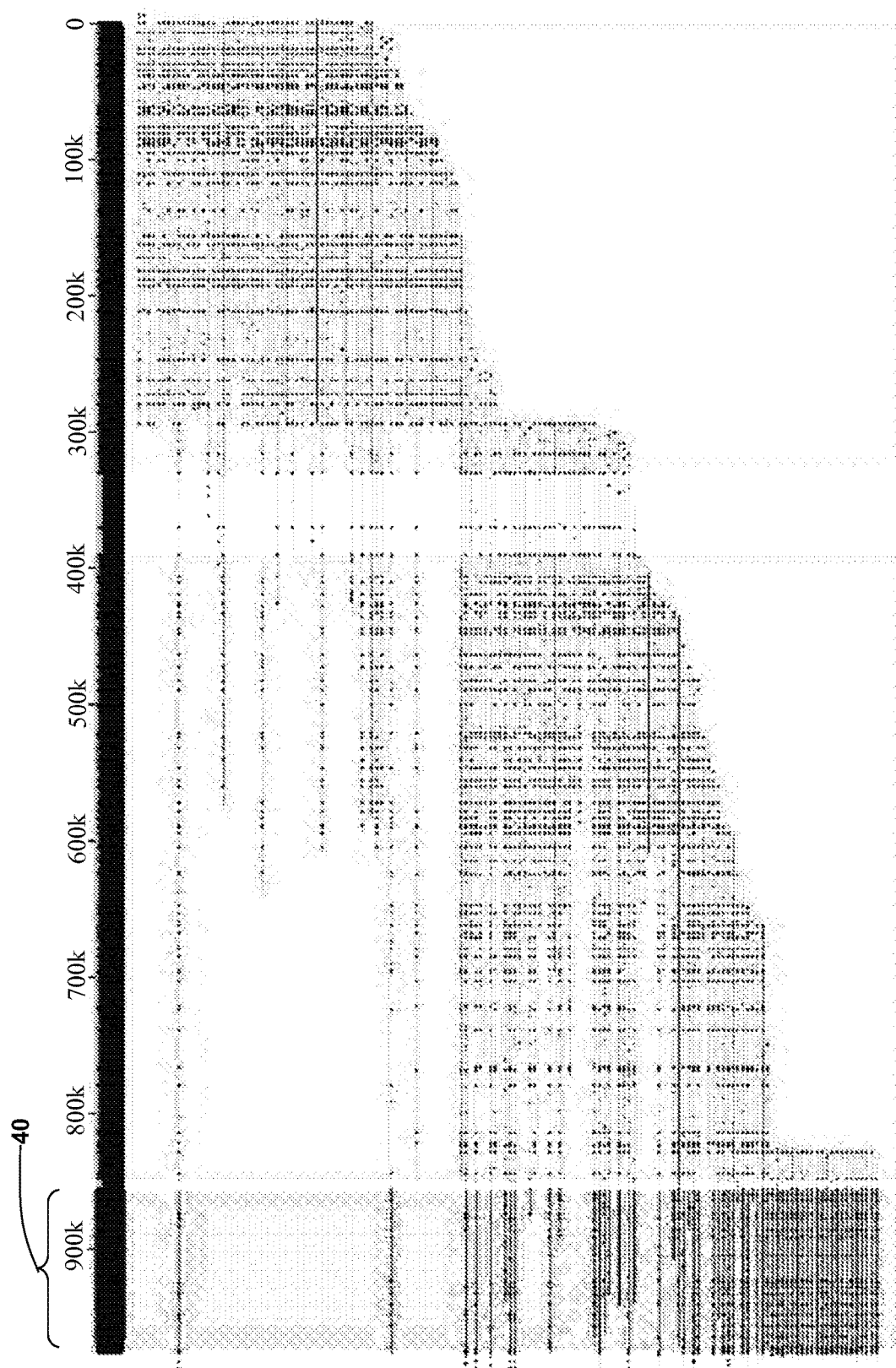
FIG. 32 is a schematic diagram illustrating single molecule data for the translocation 40 depicted in FIG. 31 in accordance with some embodiments herein.
Figure 33:
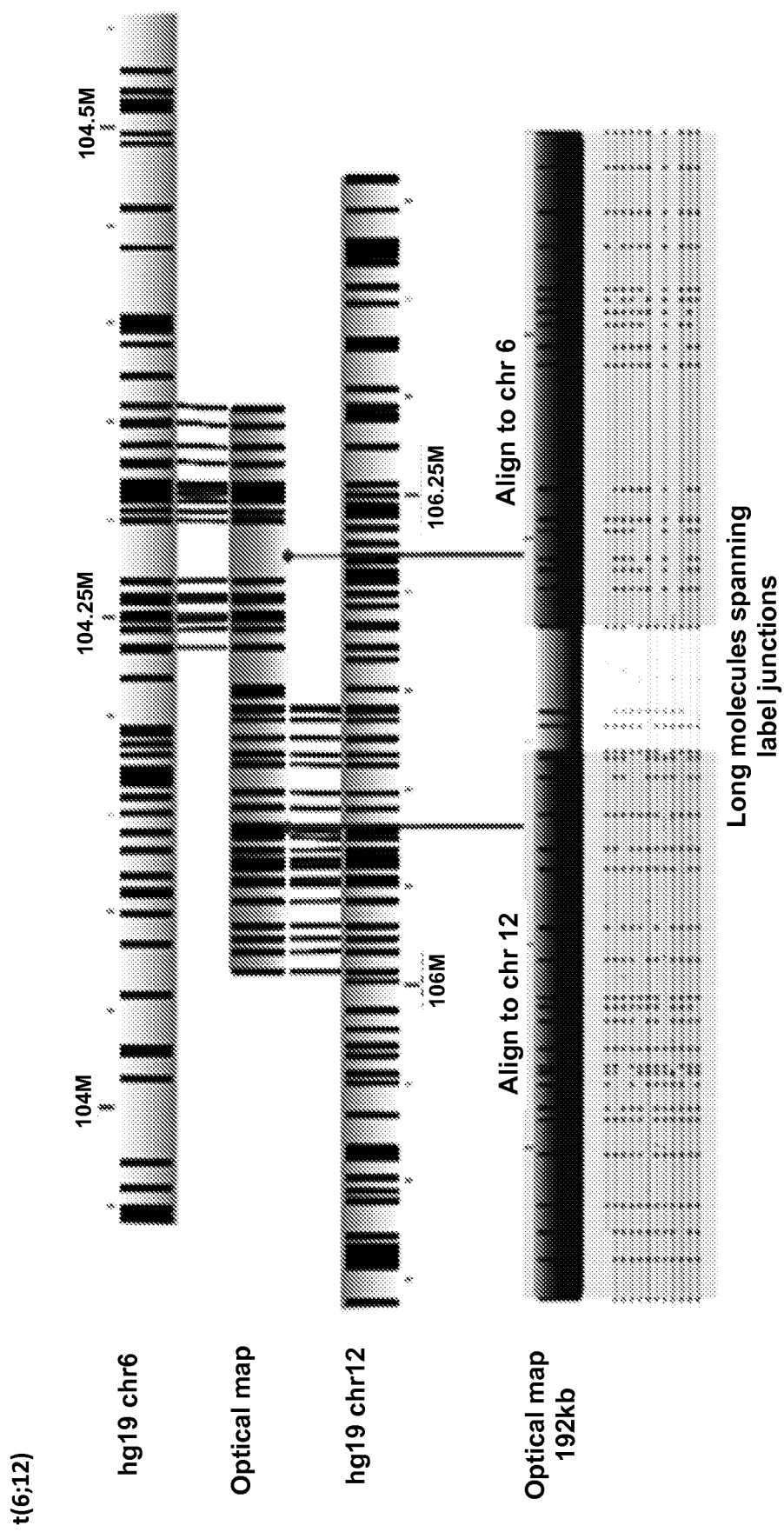
FIG. 33 is a schematic diagram illustrating identification of a translocation involving chromosomes 6 and 12 in accordance with some embodiments herein. The breakpoint to vertical line 22 from FIG. 30B. Some long molecules spanned the translocation junctions.

Automatic detection of genomic structural variation was performed. Human samples were labeled, and genome maps were generated using an Irys™ system (Bionano genomics). The GROM copy number profile was generated as described herein. Breakpoints were automatically identified using the GROM copy number profile. P-values of $10^{-10}$ were used to identify significant changes in absolute copy numbers. RPSA complex structural variant calls were also generated using the RPSA algorithm. As shown in FIG. 30A, GROM copy number profile of human Chromosome 6 (black trace) overlapped with automated RPSA complex SV calls (vertical lines 10). The horizontal lines indicate the expected (integer) copy-number elevations. As shown in FIG. 30B, the negative logarithm (base 10) of p-values associated with changes in copy number profiles is charted (black trace). Vertical lines represent RPSA complex SV calls that do not overlap (10) or do overlap (20, 21, 22) with p-value peaks (i.e. GROM copy number breakpoints) exceeding the cutoff of 10. A translocation involving chromosomes 6 and 10 was identified at the position of vertical line 21 from FIG. 30B. The translocation is schematically mapped in FIG. 31, which illustrated the translocated region 40, and a possible deletion 50, based on a lack of mapping to a portion of chromosome 10. FIG. 32 illustrates an alignment of single molecules from the translocation region of FIG. 31. FIG. 33 schematically illustrates a translocation corresponding to vertical line 22 from FIG. 30B.

Example 4

An implementation of SIMONIDA was performed for a plurality of samples, including euploid males and females, a subject with a known subchromosomal aberration in Chr22 (22q11, di George syndrome), a COLO829 cancer sample, and an additional cancer sample (a multiple myeloma patient-derived CDC138 cell line).

The following values were applied to the implementation of the copy number per label normalization. The procedure applied condensation to hg19 using mres=2.9 and yielding 343,409 condensed labels. It is contemplated that other reference genomes and other label condensation schemes in accordance with some embodiments herein will generate different numerical ranges. The total number of labels is 343,409. The number of autosomal labels is 323,149. A convenient value for the multiplier C is 105. The number of labels per chromosome are as follows: Chr1: 28.177, Chr2: 28,823, Chr3: 23,054, Chr4: 20,952, Chr5: 20,943, Chr6: 19,985, Chr3: 18,094, Chr8: 17,109, Chr9: 14,618, Chr10: 16,233. Chr11: 16,519, Chr12: 15,511, Chr13: 10,634, Chr14: 10,466, Chr15: 10,478, Chr16: 9,785, Chr17: 9,984, Chr18: 8.956, Chr19: 6,132, Chr20: 7,869. Chr21: 4,163, Chr22: 4,664, ChrX: 17,406. ChrY: 2,854. The number of labels that survive interval filtering with relative error cutoff of 25% is ~250,000. The raw coverage values range from 1 to 700. The observed lambda values range from 50 kb to 210 kb. Label parameter values: zero-order coefficients range from 0.02 to 3.4 with a median of 1.000 and mean of 0.976, gradients range from −2.2 to 2.4 with vanishing median and mean values. Copy number profiles for euploid samples are centered at 2 (autosomes and ChrX in females) or 1 (ChrX and ChrY in males). The relative error in final copy number profiles (filtered labels) ranged from 10% to ~30% for euploid samples (depending on coverage). The relative error in copy number profiles generated for euploid samples decays with the coverage as reciprocal square root of the coverage, as expected. Cancer samples exhibit much higher relative error (observed up to 80%) due to biological variability.

Figure 34:
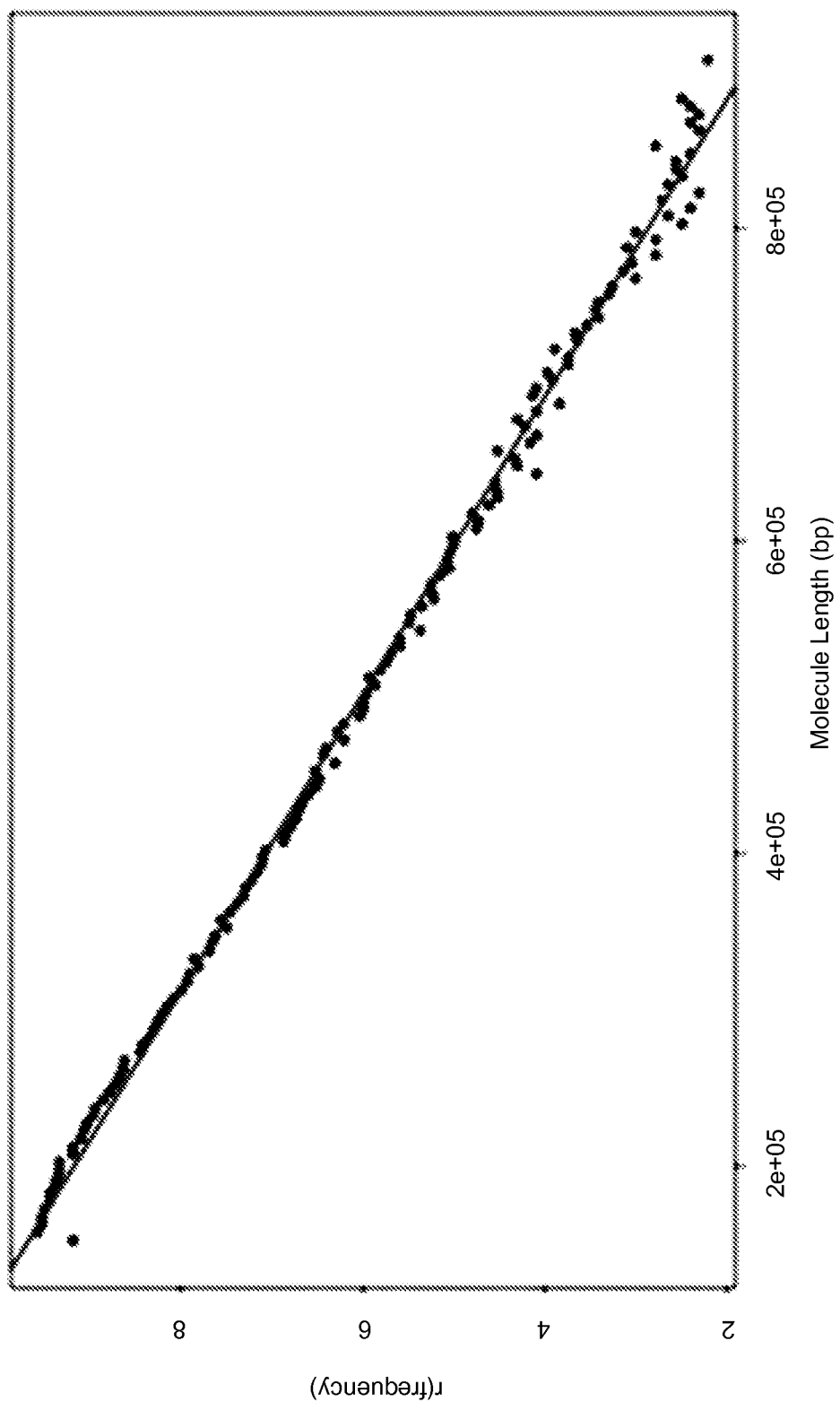
FIG. 34 is a graph of a determination of characteristic molecular length in accordance with some embodiments herein. It is noted that determination of characteristic molecular length can be useful for SIngle MOlecule Normalization to Detect Aberrations (SIMONIDA).

As shown in FIG. 34, the characteristic molecule length was determined.

Figure 35:
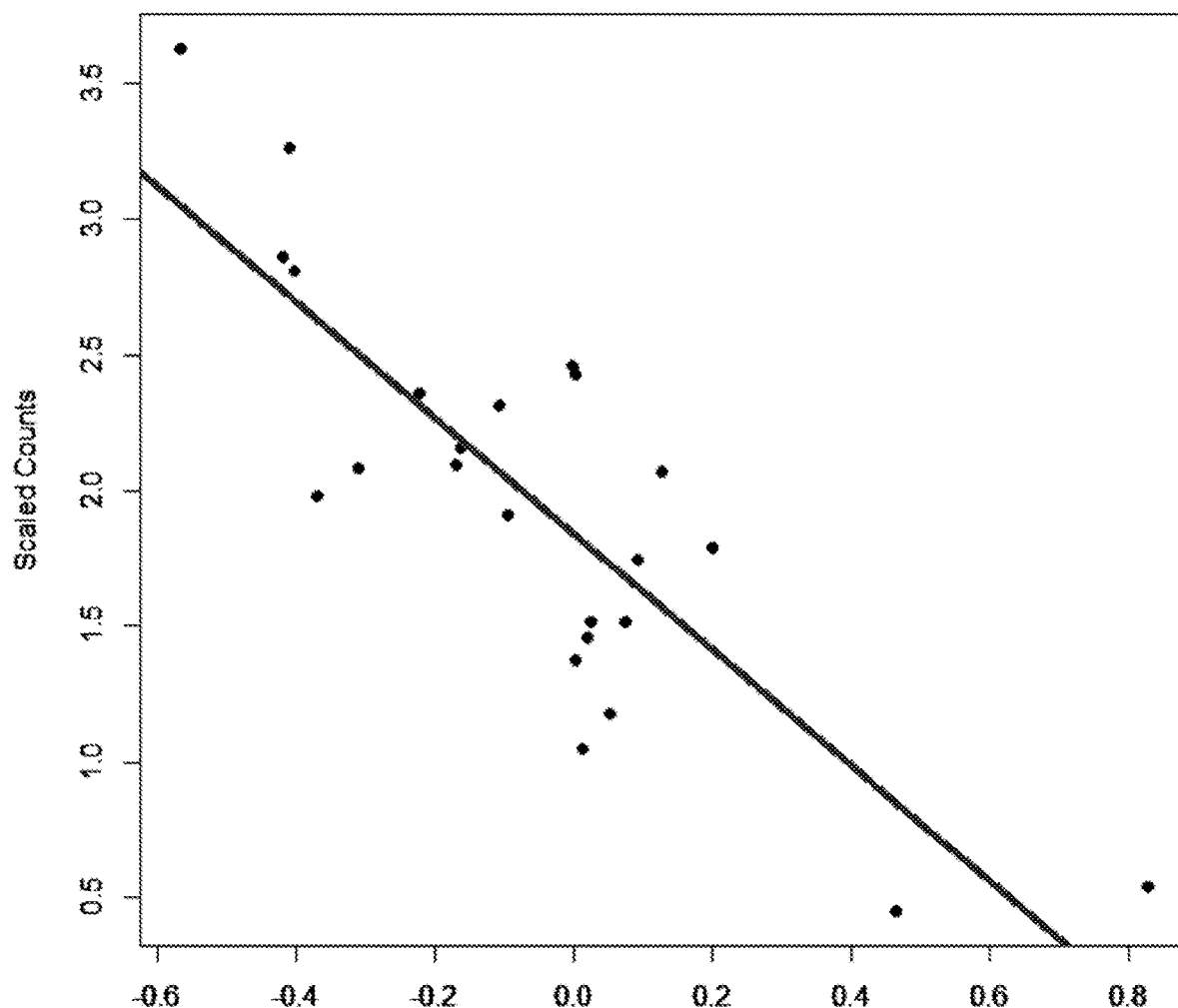
FIG. 35 is a graph illustrating determination of the zero-order coefficient (E) and gradient (G) per label in accordance with some embodiments herein. For label 4,756 in Chr9 (located at 41,651,803 bp), E=1.84±0.09 and G=−2.13±0.30.

As shown in FIG. 35, the zero-order coefficient (E) and gradient (G) per label were determined.

Figure 36A:
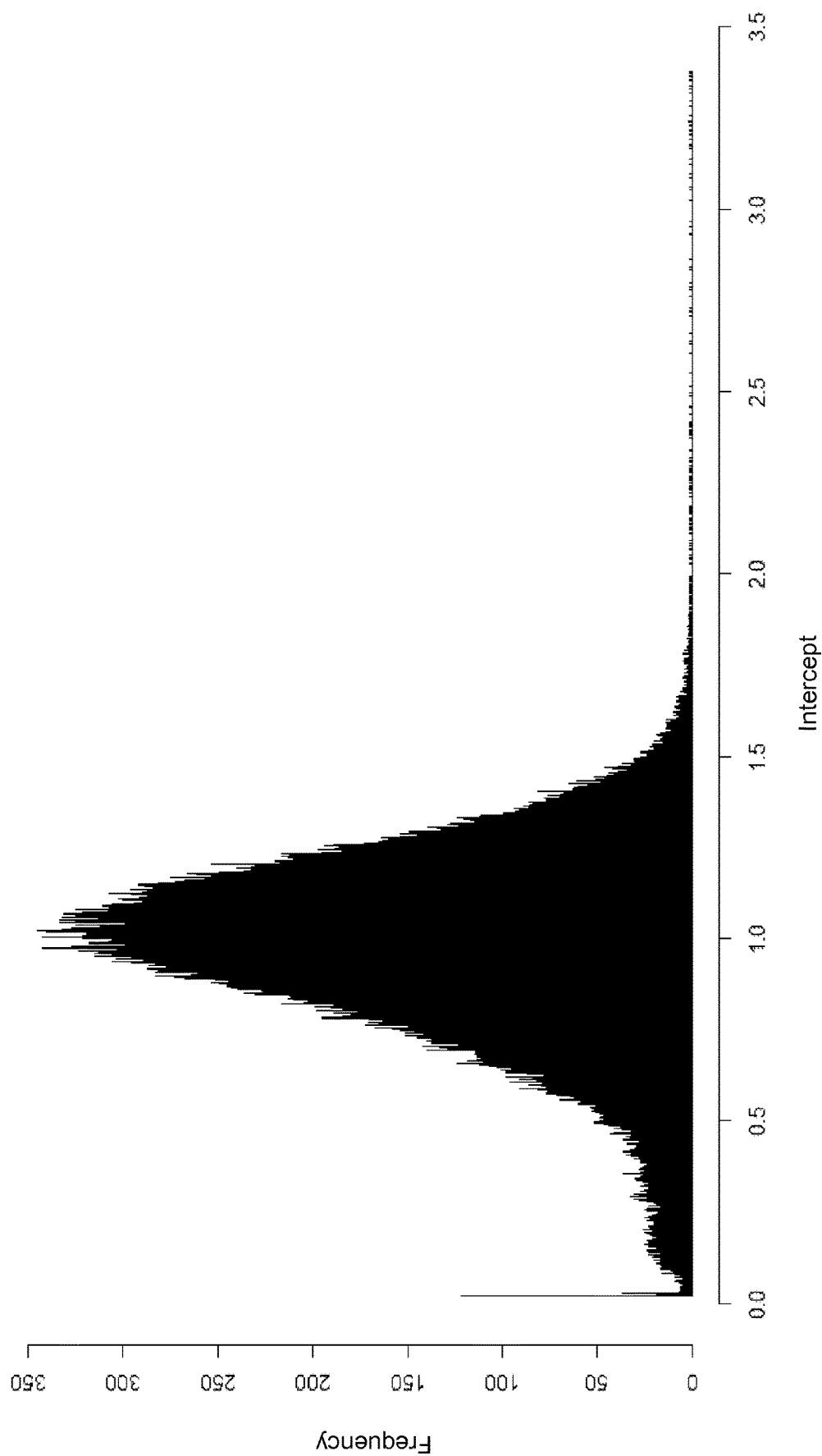
FIG. 36A is a graph illustrating distribution of zero-order coefficient values per label in accordance with some embodiments herein.
Figure 36B:
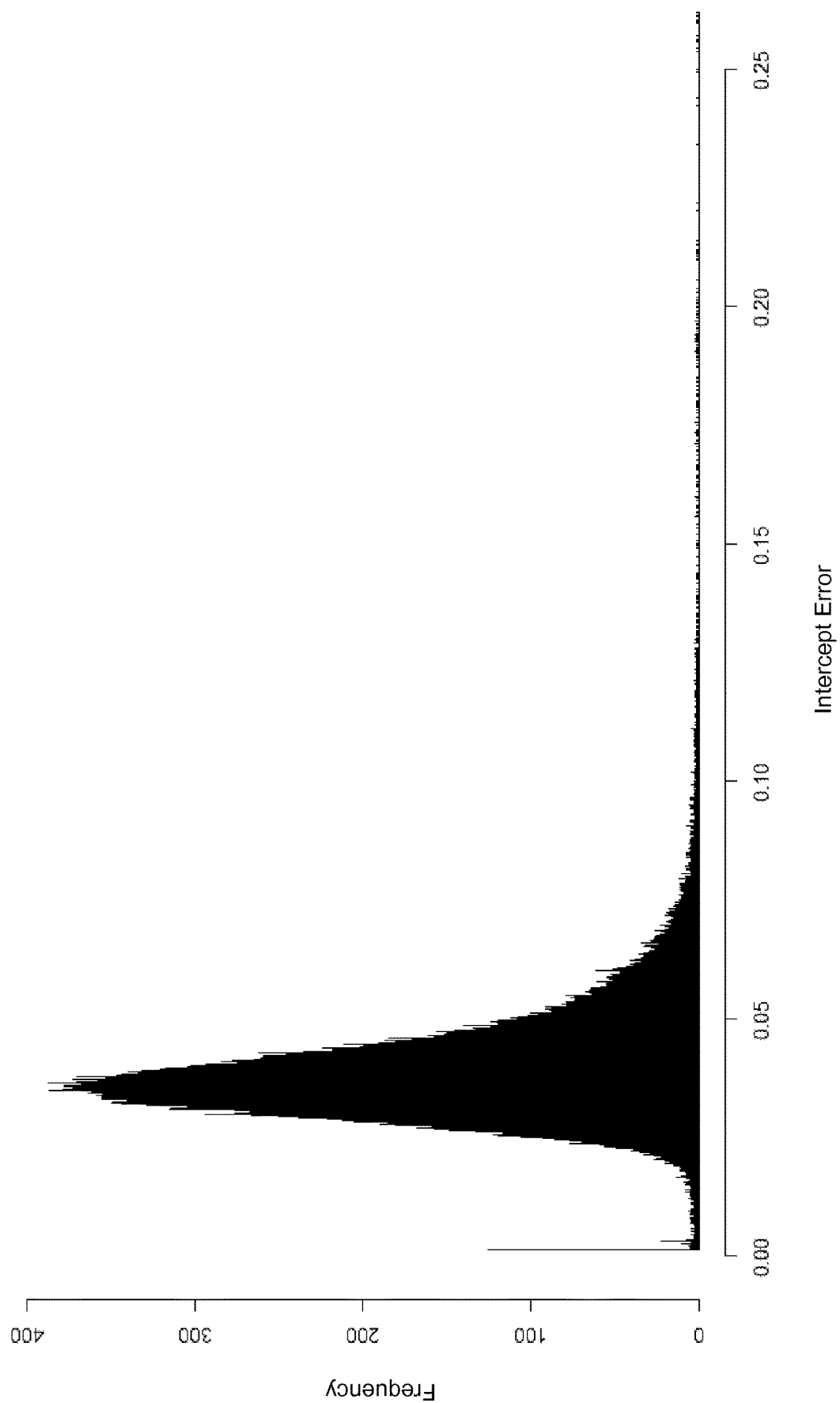
FIG. 36B is a graph illustrating distribution of zero-order coefficient errors per label in accordance with some embodiments herein.
Figure 37B:
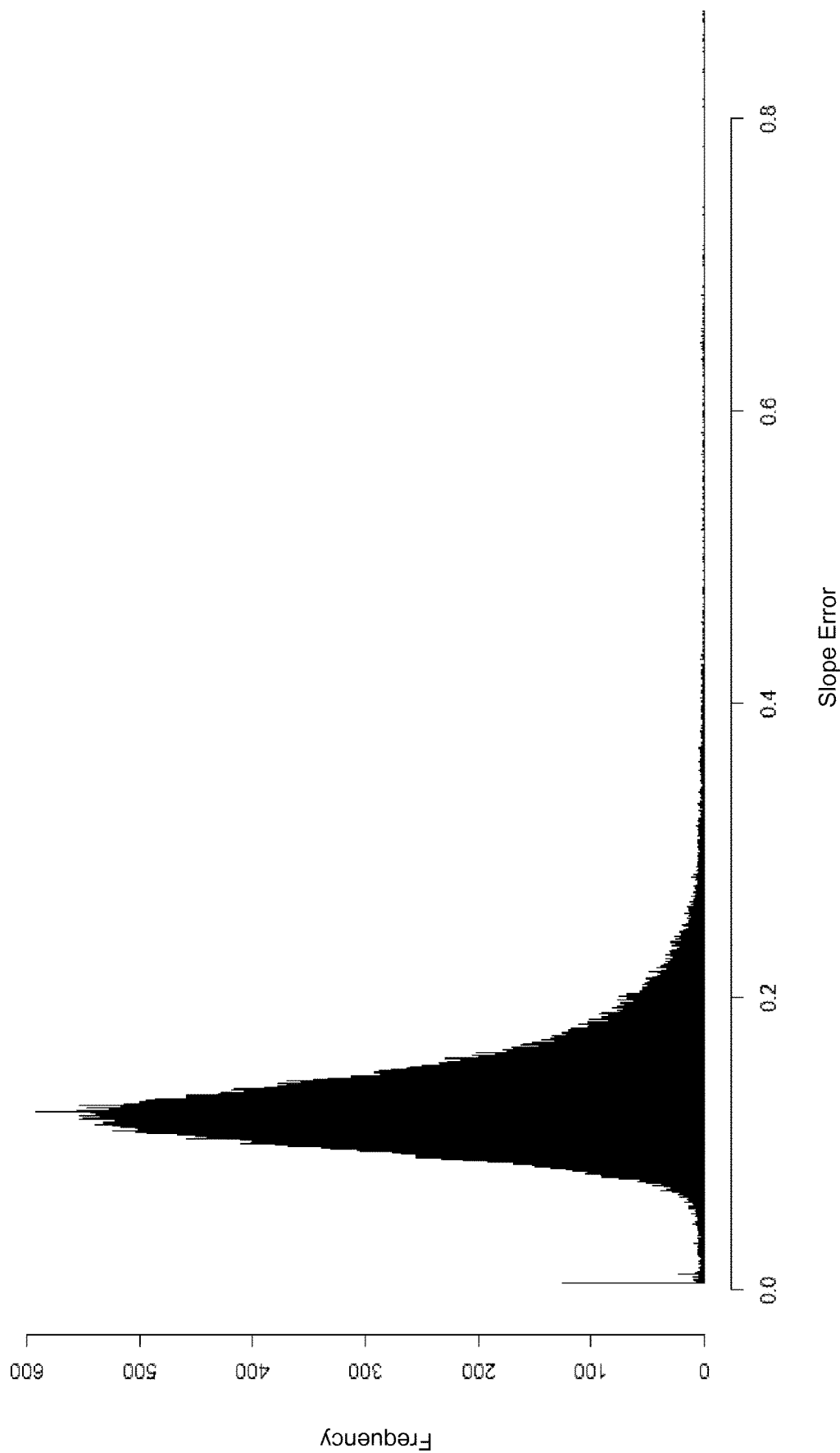
FIG. 37B is a graph illustrating distribution of gradient errors per label in accordance with some embodiments herein.
Figure 38A:
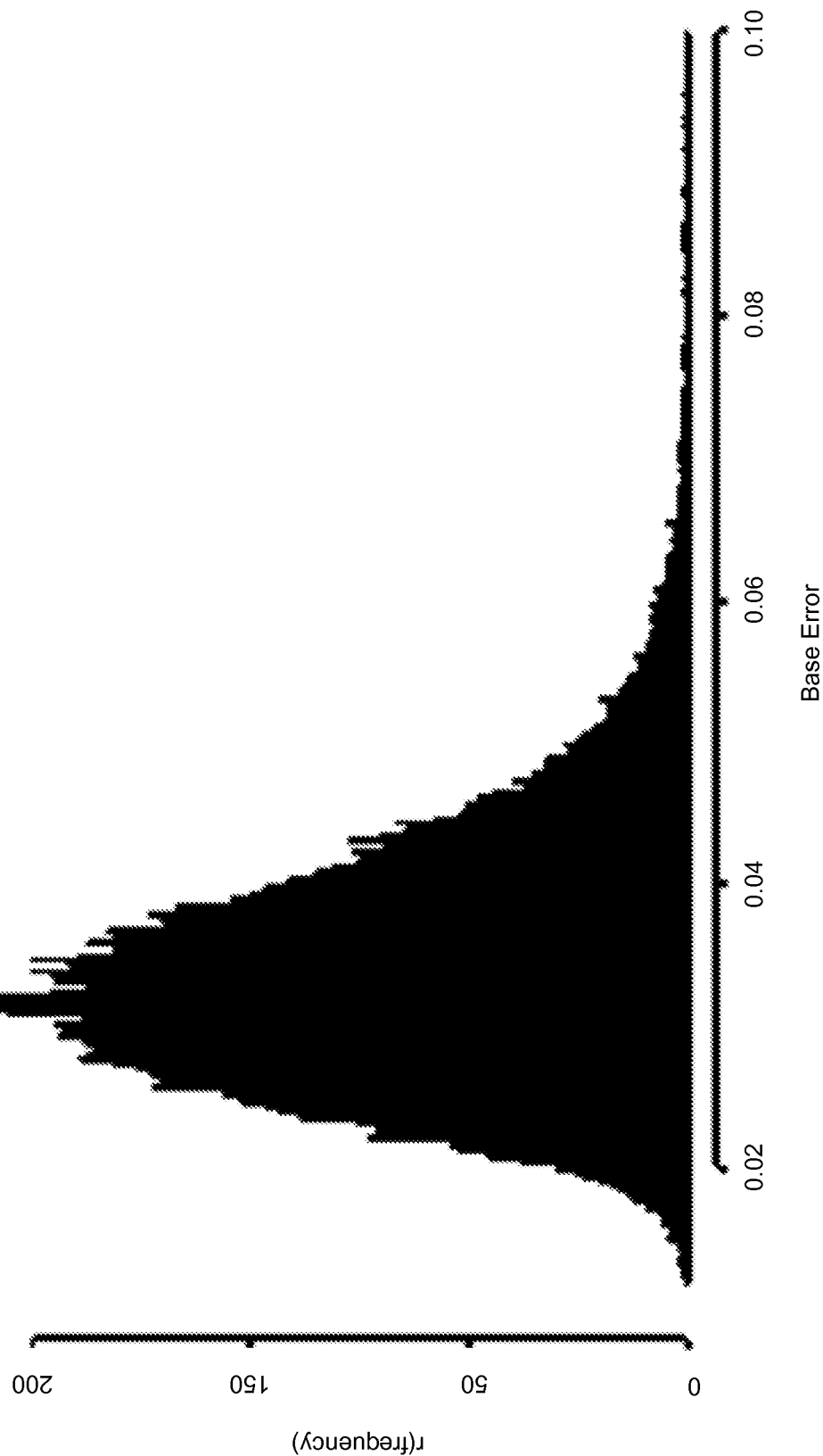
FIG. 38A is a graph illustrating distribution of base error estimates per label in accordance with some embodiments herein.
Figure 38B:
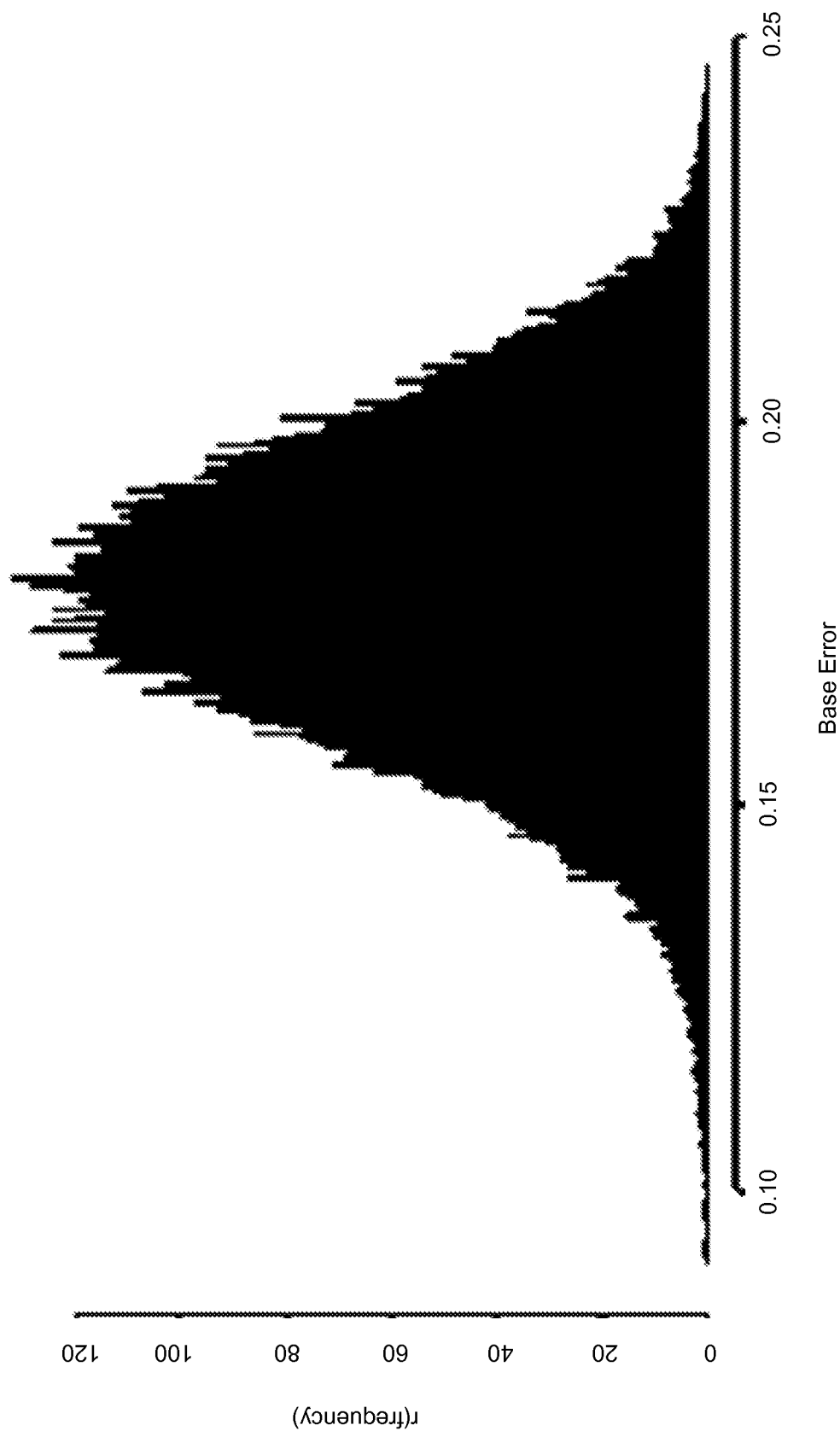
FIG. 38B is a graph illustrating distribution of total error estimates per label in accordance with some embodiments herein.

As shown in FIG. 36A, distribution of zero-order coefficient values per label was determined. As shown in FIG. 36B, distribution of zero-order coefficient errors per label was determined. As shown in FIG. 37A, distribution of gradient values per label was determined. As shown in FIG. 37B, distribution of gradient errors per label was determined. As shown in FIG. 38A, distribution of base error estimated per label for a selected euploid sample was determined. As shown in FIG. 38B, distribution of total error estimates for a selected euploid sample was determined.

Figure 39:
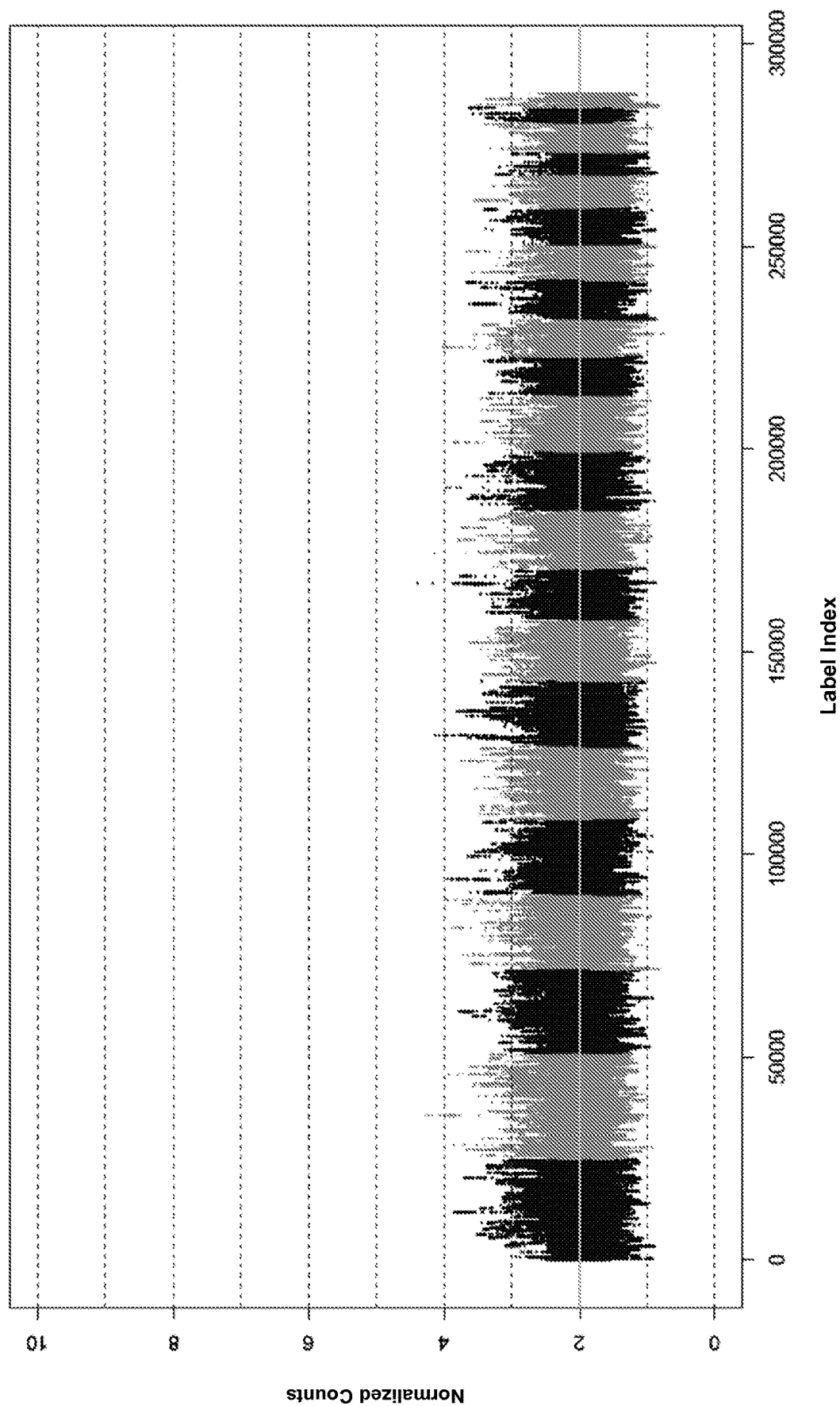
FIG. 39 is a graph showing an example of a copy number per label profile as determined using SIMONIDA in accordance with some embodiments herein. The copy number per label profile is for a subject with a known subchromosomal aberration in Chr22 (22q11, di George syndrome). All autosomal chromosomes are shown.
Figure 40:
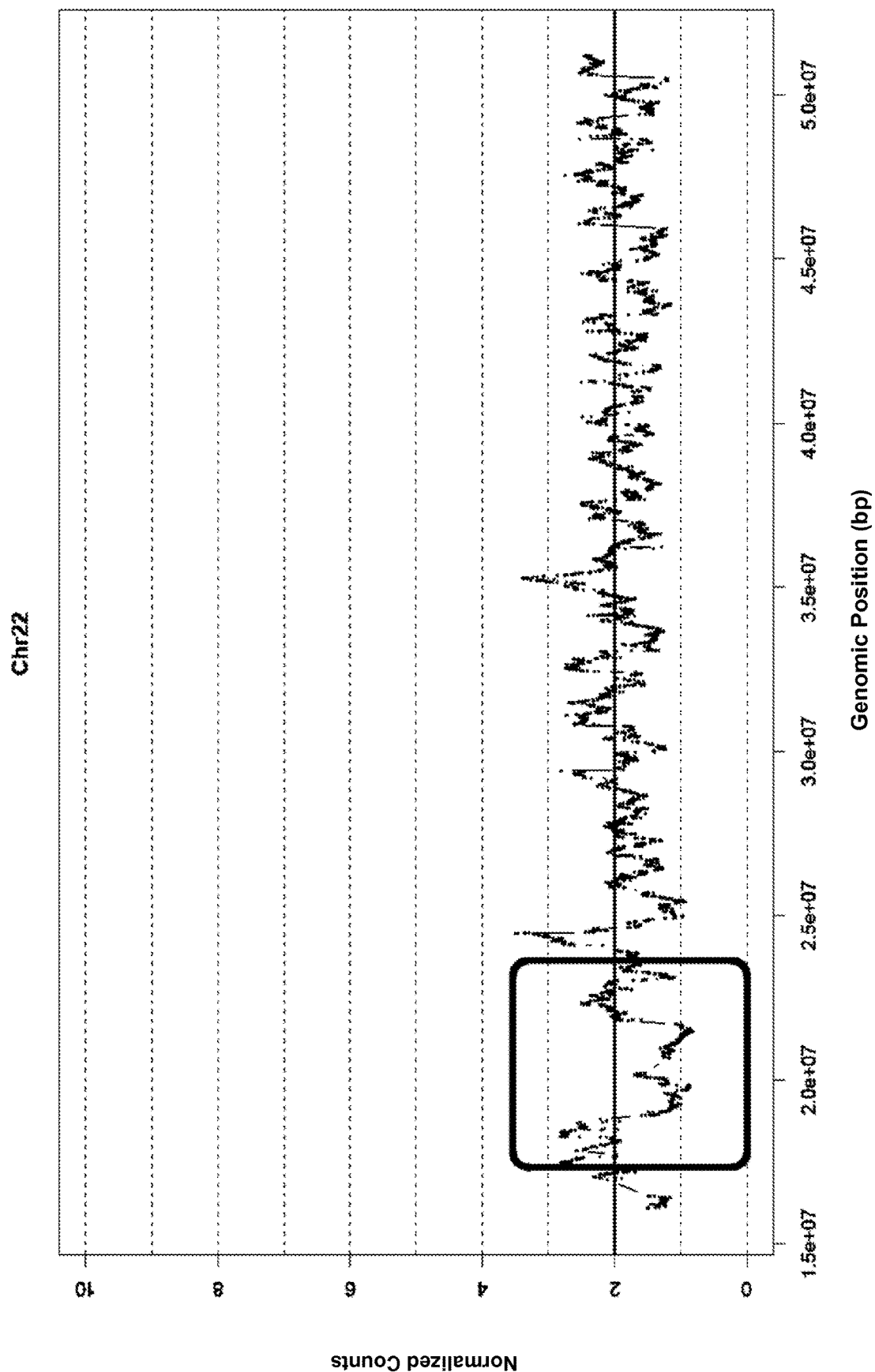
FIG. 40 is a graph showing an example of a copy number per label profile as determined using SIMONIDA in accordance with some embodiments herein. The copy number per label profile is for a subject with a known subchromosomal aberration in Chr22 (22q11, di George syndrome). Chr22 is shown, with the affected area (18-22 Mbp) highlighted.

As shown in FIG. 39, an example copy number per label profile in a subject with a known subchromosomal aberration in Chr22 (22q11, di George syndrome) was generated. FIG. 40 shows Chr22 of the subject, with the affected area (18-22 Mbp) highlighted. As such, it is contemplated that methods and systems in accordance with some embodiments herein can generate a copy number profile in which bias is reduced or eliminated, and which can be used to identify chromosomal abnormalities (e.g., di George syndrome).

Figure 41:
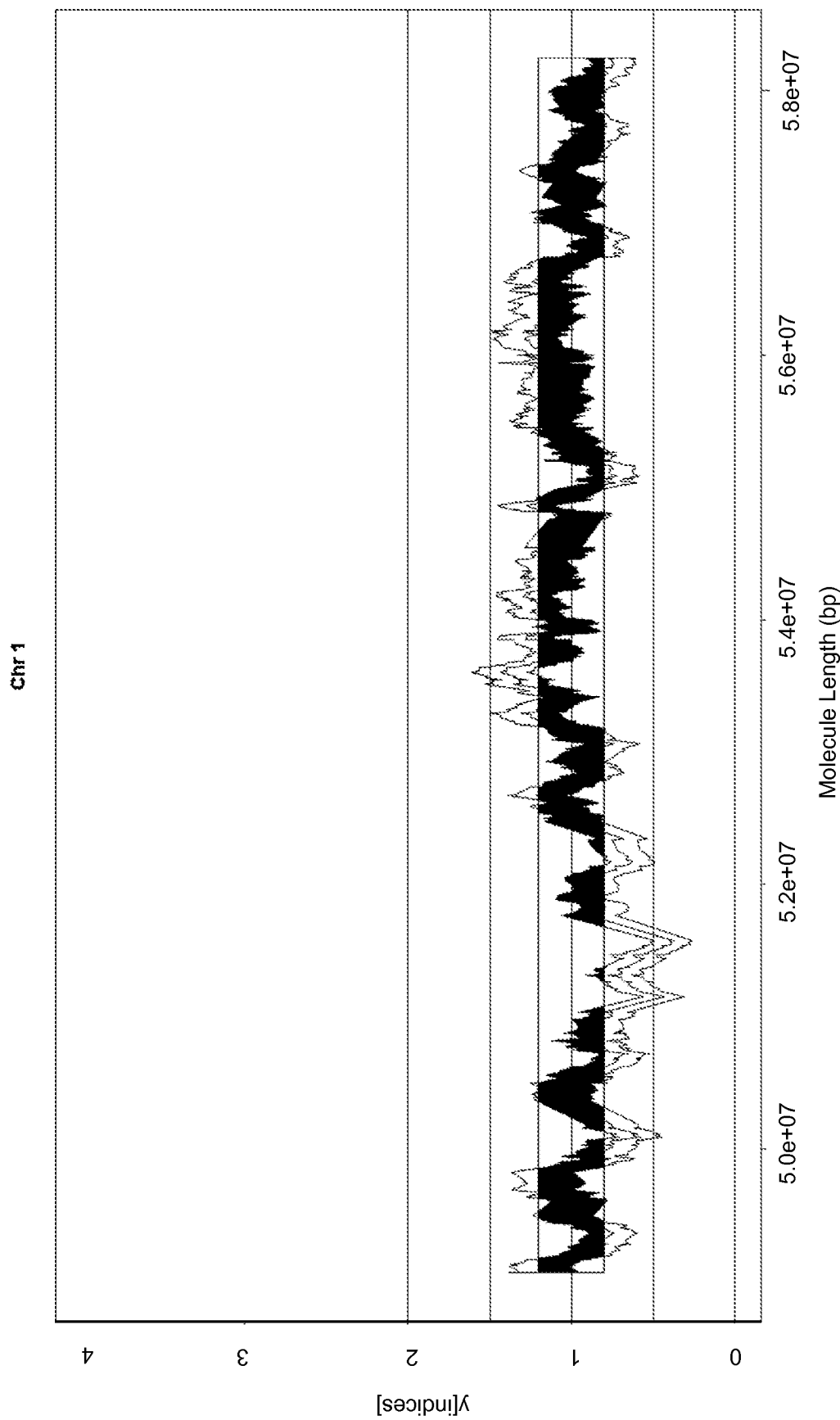
FIG. 41 is a graph illustrating a calculation of uncertainty in copy number per label values (before scaling to two chromosome copies), which can be calculated in accordance with some embodiments herein.

As shown in FIG. 41, uncertainty in copy number per label values (before scaling to two chromosome copies) was determined.

Figure 42:
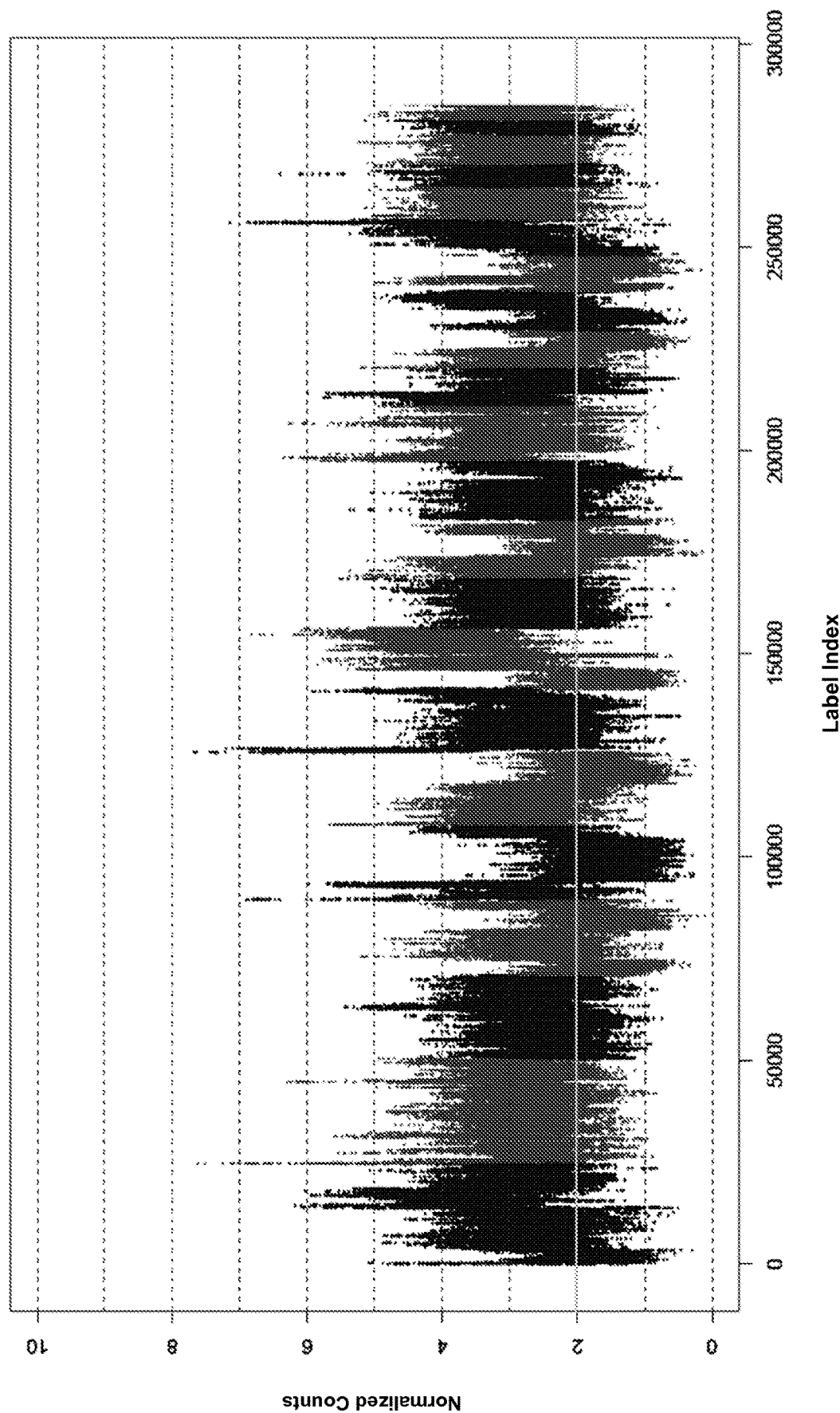
FIG. 42 is a graph illustrating an example of a copy number profile per label as determined using SIMONIDA for a cancer sample (COLO829) in accordance with some embodiments herein. The standard deviations for Chr2 and Chr5 are 0.608 (25,903 labels) and 0.450 (18,715 labels), respectively. For comparison, the standard deviations of the GROM profile for the same sample are 0.804 for Chr2 (4,864 intervals, interval size 50 kb) and 0.589 (3,619 intervals). As such, in comparison to GROM, the normalization procedure using SIMONIDA achieves an improvement of ~25% in relative error, with the simultaneous 4-7-fold improvement in resolution.

An example copy number profile as calculated by SIMONIDA for a cancer sample (COLO829) is shown in FIG. 42. It is noted that the standard deviations for Chr2 and Chr5 were 0.608 (25,903 labels) and 0.450 (18,715 labels), respectively. For comparison, the standard deviations of the GROM profile for the same sample were 0.804 for Chr2

(4,864 intervals, interval size 50 kb) and 0.589 (3,619 intervals). As such, SIMONIDA achieved an improvement of ~25% in relative error, with the simultaneous 4-7-fold improvement in resolution, in comparison to GROM.

Figure 43:
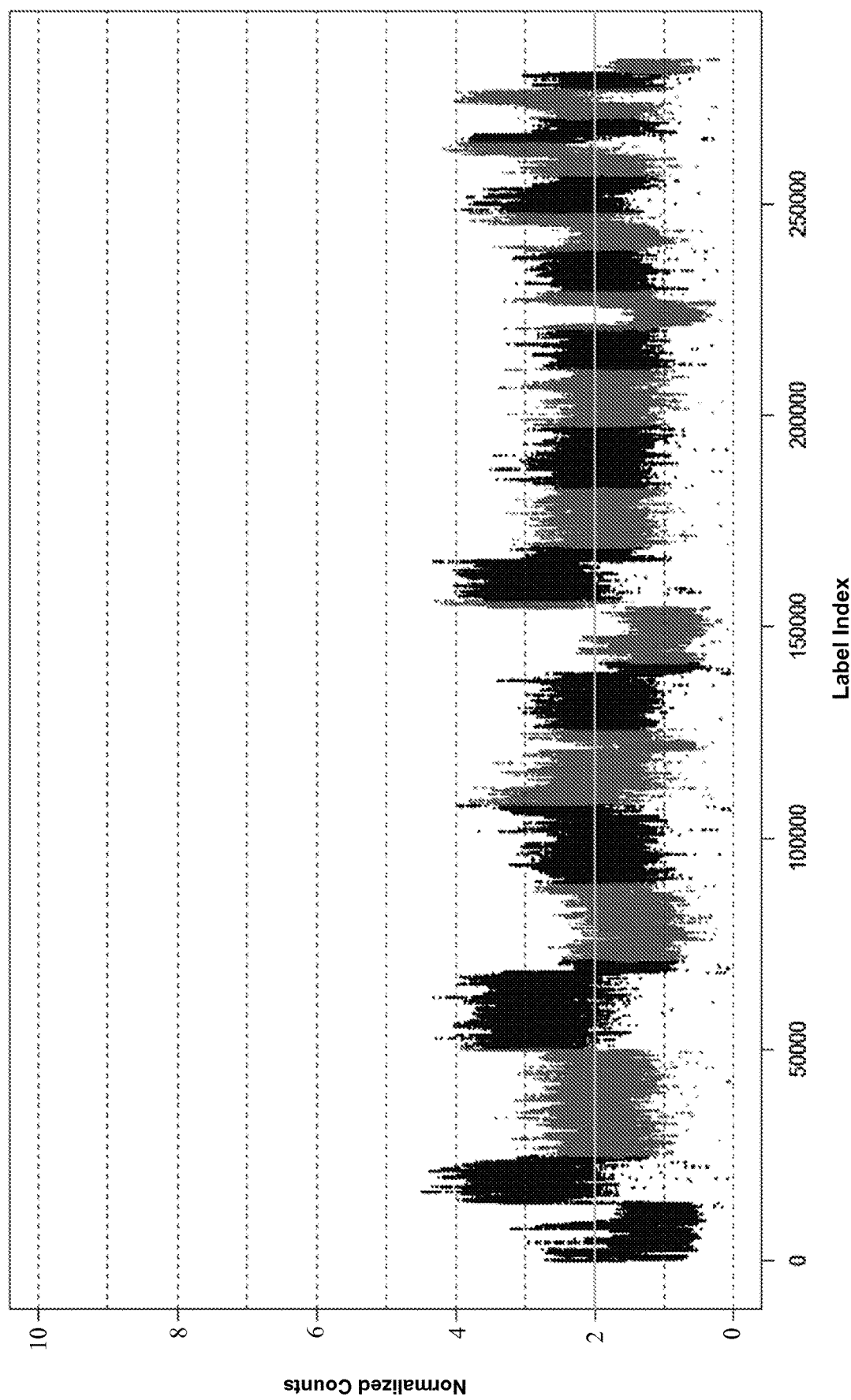
FIG. 43 is a graph illustrating an example of a copy number profile per label (autosomes only) as determined using SIMONIDA for a different cancer sample that FIG. 42 in accordance with some embodiments herein.

An example copy number profile as calculated by SIMONIDA for an additional cancer sample is shown in FIG. 43.

Unexpectedly, SIMONIDA also yielded high precision of ChrY coverage depth profiles, in spite of a small number of available male training sample. The high precision ChrY coverage depth profiles are also noteworthy in view of the known sequential similarity between ChrY and the rest of the genome, in particular ChrX.

Moreover, in comparison to quantized copy number profiles (e.g. GROM copy number profiles), SIMONIDA yielded higher precision than the quantized copy number profile, in addition to 5-7 fold increase in resolution.

Example 5

An implementation of Sex Chromosome Normalization was performed for a plurality of samples. SIMONIDA scaled coverage depths were obtained for a training set. ChrX scaled coverage depths were divided by a scaling factor of (number of X chromosomes −1) for each sample of the training set. ChrY scaled coverage depths were divided by a scaling factor of (number of Y chromosomes) for each sample of the training set. Robust linear regression against SIMONIDA abscissa was performed. Error propagation for ChrX was estimated using Taylor expansion. Error propagation for ChrY was estimated using MAD. For a CEPH trio (NA12878, female, and NA12891, male), SIMONIDA copy number profiles comprising Sex Chromosome Normalization were obtained. For each sample, a Second Normalization was performed, in which normalized coverage depths for ChrX were divided by median normalized coverage depths obtained across all female training samples, and in which normalized coverage depths for ChrY were divided by median normalized coverage depths obtained across all male training samples, and in which normalized coverage depths for ChrY were also divided by 2.

Figure 46A:
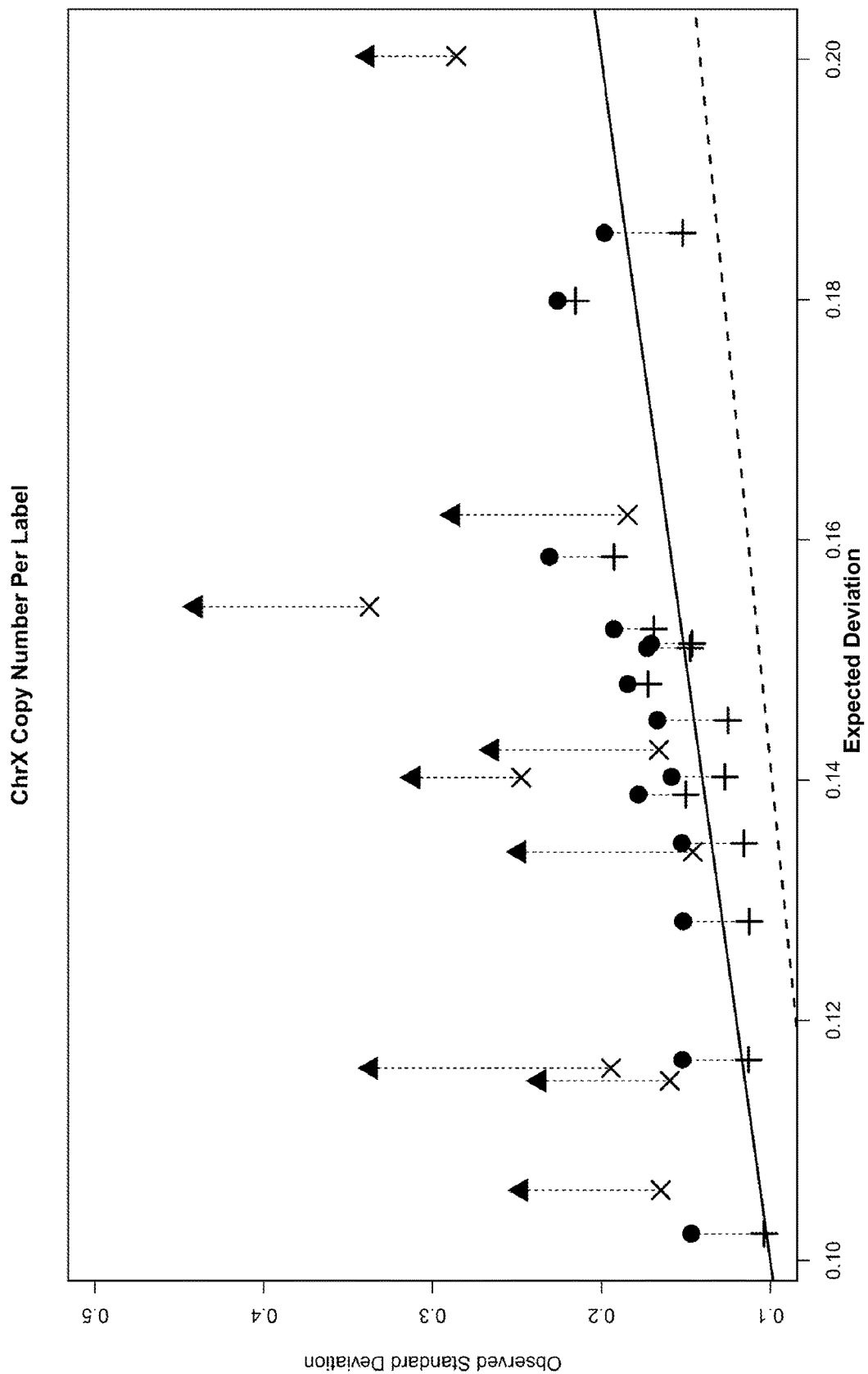
FIG. 46A is a graph illustrating observed standard deviation for ChrX copy number per label comprising normalized copy number per label and comprising Sex Chromosome Normalization in accordance with some embodiments herein.
Figure 46B:
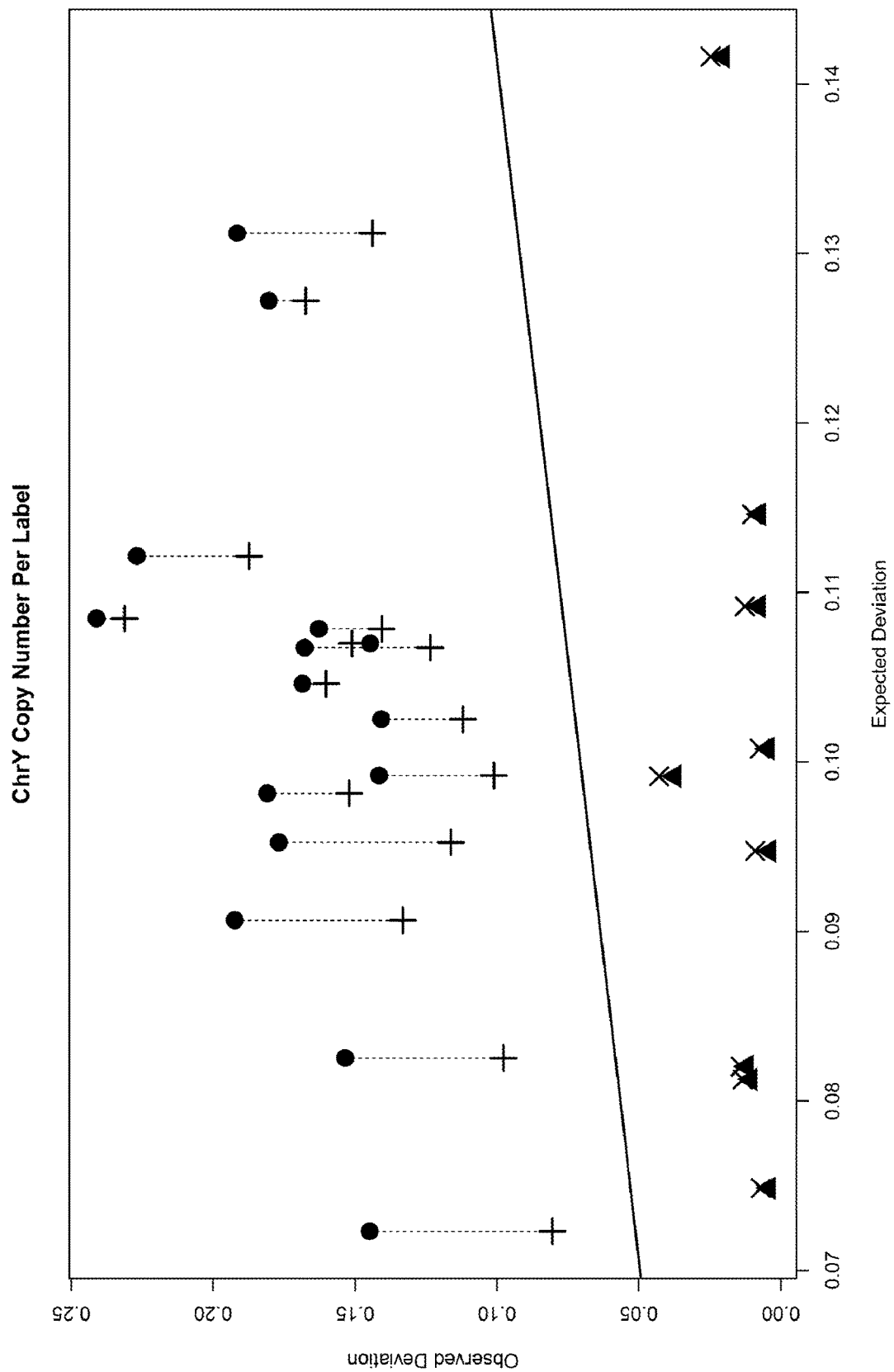
FIG. 46B is a graph illustrating observed standard deviation for ChrY copy number per label comprising normalized copy number per label and comprising Sex Chromosome Normalization in accordance with some embodiments herein.

As shown in FIGS. 46A and 46B, the Sex Chromosome Normalization including Second Normalization substantially improved standard deviations compared to profiles that did not undergo second normalization.

In each of FIGS. 46A and 46B, Triangles: standard deviation of normalized ChrX/Y profiles in females before division by median normalized coverage depths. X: standard deviation of normalized ChrX/Y profiles in females after division by median normalized coverage depths. Filled circles: standard deviation of normalized ChrX/Y profiles in males before division by median normalized coverage depths. Crosses: standard deviation of normalized ChrX/Y profiles in males after division by median normalized coverage depths. Vertical dashed lines: improvement (before vs. after division by normalized median coverage depths). Tilted dashed line in FIG. 46A: expected standard deviation for ChrX in males based on a simple Poisson model, equal to $1/\sqrt{2N}$, where N stands for total autosomal coverage depths. This is the theoretical limit in the absence of any biases. Tilted full line in FIG. 46A: expected standard deviation for ChrX in females based on the same Poisson model, equal to $1/\sqrt{N}$. Tilted line in FIG. 46B: expected standard deviation for ChrY in males, based on the same model, equal to $1/\sqrt{2N}$.

Figure 47B:
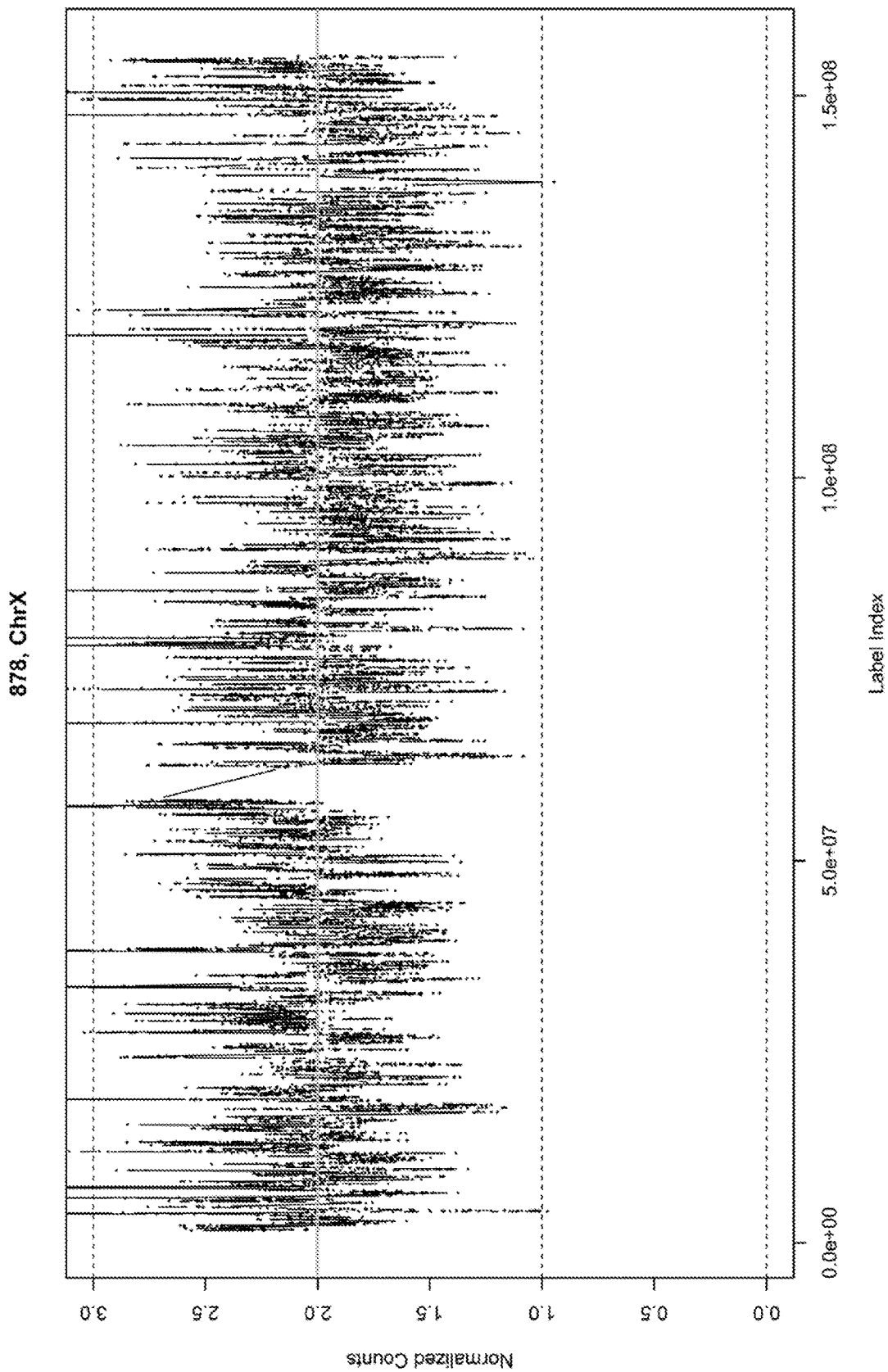
FIG. 47B illustrating an example of a copy number profile per label for an X chromosome of a NA12878 (female) cell line as determined using SIMONIDA and comprising Sex Chromosome Normalization in accordance with some embodiments herein.
Figure 47C:
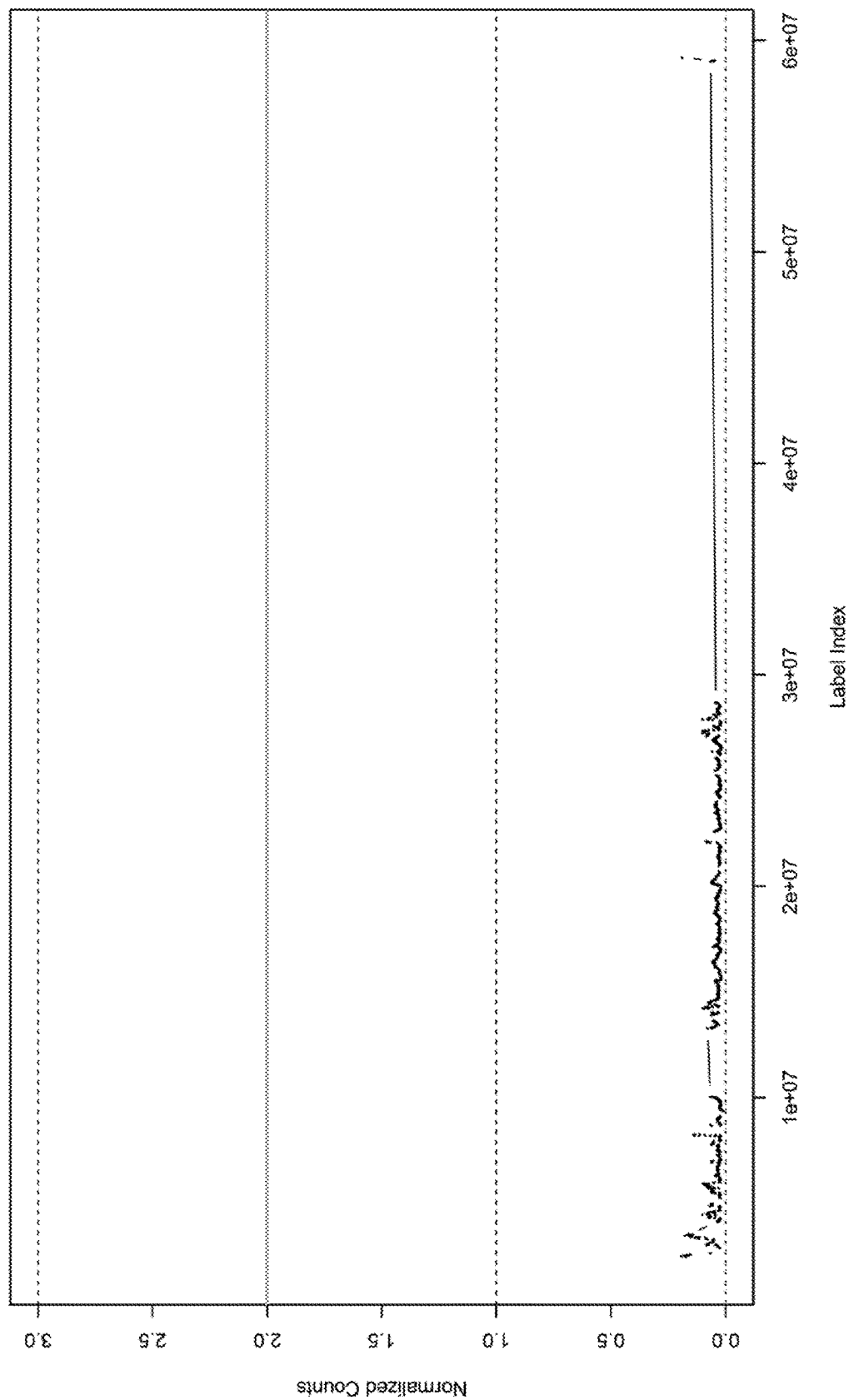
FIG. 47C illustrating an example of a copy number profile per label for any Y chromosome labels identified in NA12878 (female) cell line as determined using SIMONIDA and comprising Sex Chromosome Normalization in accordance with some embodiments herein. The results are consistent with the absence of a Y chromosome.
Figure 48A:
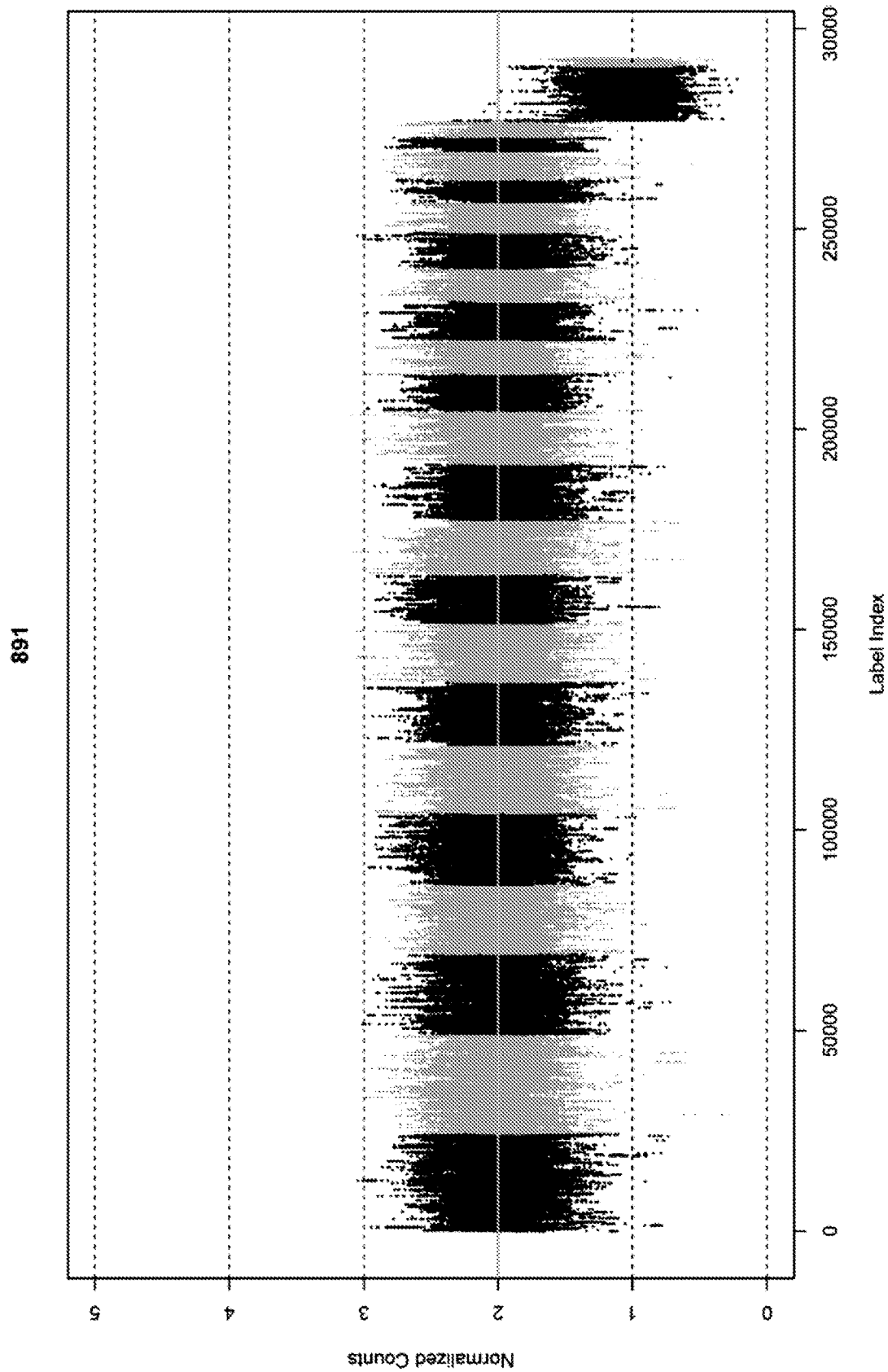
FIG. 48A is a graph illustrating an example of a copy number profile per label for a NA12891 (male) cell line as determined using SIMONIDA and comprising Sex Chromosome Normalization in accordance with some embodiments herein.
Figure 48B:
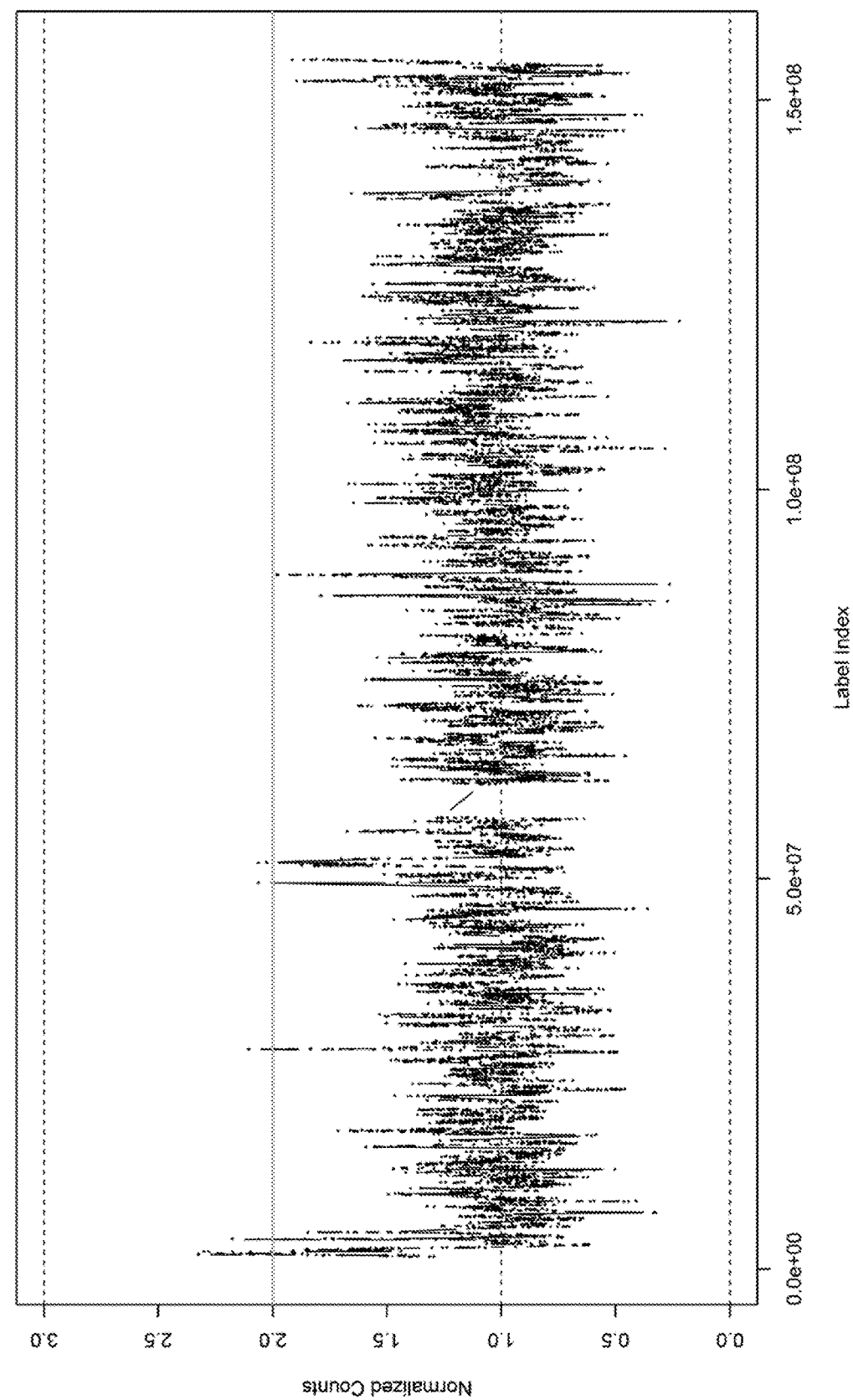
FIG. 48B is a graph illustrating an example of a copy number profile per label for an X chromosome of a NA12891 (male) cell line as determined using SIMONIDA and comprising Sex Chromosome Normalization in accordance with some embodiments herein.
Figure 48C:
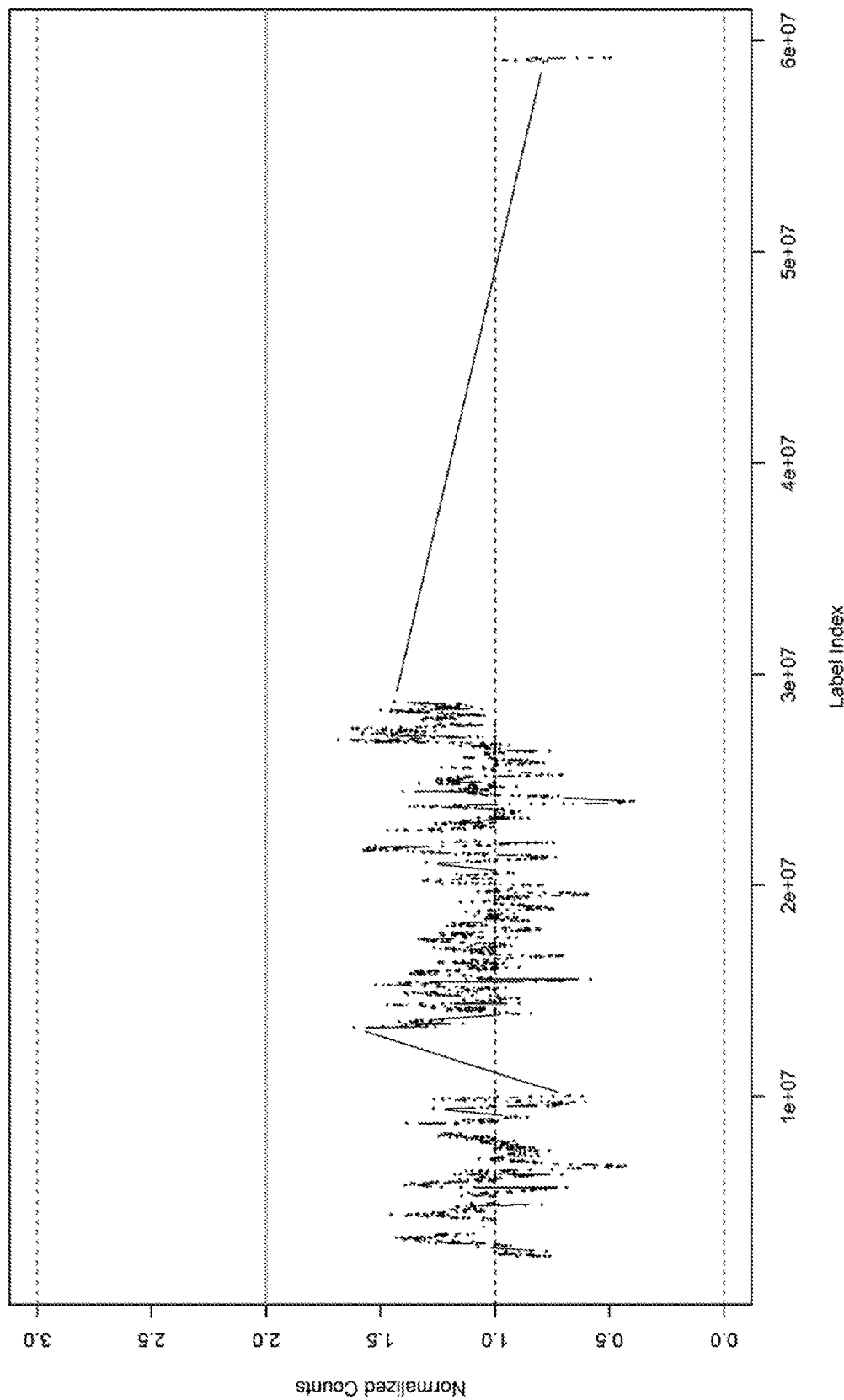
FIG. 48C is a graph illustrating an example of a copy number profile per label for a Y chromosome of a NA12891 (male) cell line as determined using SIMONIDA and comprising Sex Chromosome Normalization in accordance with some embodiments herein.

As shown in the copy numbers profiles for NA12878 female cells (FIGS. 47A-C), the copy number profile robustly and consistently indicated a copy number of 2 for the autosomes and ChrX. FIG. 47B illustrates that the copy number profile of the X chromosome is consistent with diploidy throughout the X chromosome. FIG. 47C illustrates that the copy number profile of the female genome is consistent with the absence of the Y chromosome. As shown in the copy numbers profiles for NA12891 male cells (FIGS. 48A-C), the copy number profile reliably indicated a copy number of 2 for the autosomes, and a copy number of 1 for ChrX and ChrY. FIG. 48B illustrates that the copy number profile of the X chromosome for the male genome depicts a single copy throughout the X chromosome. FIG. 48C illustrates that the copy number profile for the male genome depicts a single copy of the Y chromosome throughout the Y chromosome.

Example 6

Normalization by Number of Labels is performed as follows. A training set comprising 20 male genomes and 20 female genomes is provided. Samples are nick-labeled, and labeling is analyzed on an Irys™ system (BioNano genomics). Quality filters are applied based on signal-to-noise ratio and molecular length. Labeling patterns of the samples are aligned to an hg19 reference genome. A histogram of number of labels per a segment of predetermined length of 100 kb in each molecule is generated. Linear regression analysis of descriptors of number of labels per molecule is performed to determine a characteristic number of labels per molecule. A scaled label coverage depth profile is obtained based on the ratio of raw label coverage for all chromosomes to the sum of raw label coverage depths for autosomes. The scaled label coverage depths for sex chromosomes are divided by an appropriate scaling factor (for ChrX, number of ChrX in sample minus 1; for ChrY, number of ChrY in sample). Robust linear regressions are performed to define the abscissa for the sex chromosomes and a second normalization is performed for the sex chromosomes. For a newly obtained sample, the sample is nick-labeled and analyzed on an Irys™ system. Quality filters are applied based on signal-to-noise ratio and molecular length. Labeling patterns of the samples are aligned to an hg19 reference genome. A scaled label coverage depth is obtained for the newly obtained sample by dividing raw label coverage by the sum of all autosomal label coverage depths. Abscissa values are obtained for the newly-obtained data set (using regular linear regression for the autosomes and robust linear regression of the sex chromosomes), and normalized label coverage depths for the newly-obtained data set are generated, based on the characteristic number of labels per molecule as determined in the training set. A second normalization is performed for the sex chromosome labels, based on the median and MAD for all of the female samples in the training set, and the median and MAD for all of the male samples in the training set. Label quality filters are applied to the ChrY and ChrX labels. A copy number profile based on the normalized label coverage depths for autosomal labels, and the second-normalized, label-quality-filtered label coverage depths for sex chromosomes.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of characterizing a sample, the method comprising:
  labeling a plurality of sample molecules with a first label, wherein the sample molecules comprise a genome or genomic fragment;
  translocating the plurality of labeled sample molecules though a fluidic channel;
  detecting counts of signals from the labeled sample molecules so as to ascertain a pattern or plurality of patterns characteristic of the genome or genomic fragment;
  correlating signals from the labeled sample molecules to a reference to ascertain a coverage depth of signals of one or more regions of the genome or genomic fragment by the sample molecules;
  scaling the coverage depths of signals to a subset of coverage depths of signals corresponding to regions of the genome or genomic fragment that does not comprise a sex chromosome or a fragment thereof, thereby providing scaled coverage depths; and
  normalizing the scaled coverage depths by one, two, or three of:
    characteristic molecular length of the plurality of labeled sample molecules; or
    characteristic number of labels per interval for a plurality of intervals of the reference, wherein the reference comprises a plurality of intervals; or
    characteristic number of labels per molecule or characteristic number of labels within a segment of predetermined length per molecule,
  thereby generating a copy number profile of the sample molecules in which bias due to label density and bias due to factors other than label density in the copy number profile are minimized or eliminated;

wherein normalizing the scaled coverage depths comprises obtaining normalized label coverage depths as provided by the formula: $n=Q/[E+GC(1/\lambda-1/\lambda_0)]$, wherein n represents normalized label coverage depths, Q represents scaled label coverage depths, G and E respectively represent gradient and zero-order coefficient of a linear regression of scaled label coverage depths versus abscissa for a plurality of samples in a training set, lambda represents characteristic sample-specific molecule length, and $\lambda_0$ represents median characteristic molecule length for the plurality of samples of the training set.

2. The method of claim 1, wherein the plurality of intervals of the reference are of equal size.

3. The method of claim 1, further comprising automatically determining a presence or absence of possible structural variation in of the genome or genomic fragment,
wherein automatically determining a presence or absence of possible regional structural variation comprises identifying possible breakpoints in the copy number profile, wherein an interval in the copy number profile with a significantly different copy number than a neighboring interval comprises a possible breakpoint.

4. The method of claim 3, wherein automatically determining a presence or absence of possible regional structural variation comprises determining GROM copy number breakpoints.

5. The method of claim 4, further comprising, for each of the copy number breakpoints:
identifying a first region of a reference sequence on a first side of the breakpoint, and masking a second region of the reference sequence on a second side of the breakpoint, wherein the second side is opposite the first side; and
scoring only single molecule alignments that align with the reference in the first region.

6. The method of claim 1, wherein the copy number profile is generated in less than five minutes after the signals are detected.

7. A method of characterizing a sample, the method comprising:
labeling a plurality of sample molecules with a first label, wherein the sample molecules comprise a genome or genomic fragment;
translocating the plurality of labeled sample molecules though a fluidic channel;
detecting counts of signals from the labeled sample molecules so as to ascertain a pattern or plurality of patterns characteristic of the genome or genomic fragment;
correlating signals from the labeled sample molecules to a reference to ascertain a coverage depth of signals of one or more regions of the genome or genomic fragment by the sample molecules;
scaling the coverage depths of signals to a subset of coverage depths of signals corresponding to regions of the genome or genomic fragment that does not comprise a sex chromosome or a fragment thereof, thereby providing scaled coverage depths; and
normalizing the scaled coverage depths by one, two, or three of:
characteristic molecular length of the plurality of labeled sample molecules; or
characteristic number of labels per interval for a plurality of intervals of the reference, wherein the reference comprises a plurality of intervals; or
characteristic number of labels per molecule or characteristic number of labels within a segment of predetermined length per molecule,
thereby generating a copy number profile of the sample molecules in which bias due to label density and bias due to factors other than label density in the copy number profile are minimized or eliminated;
wherein normalizing the scaled coverage depths comprises Sex Chromosome Normalization, comprising:
scaling the scaled label coverage depths for a training sample based on the number of sex chromosomes in the training sample; and
normalizing scaled label coverage depths with respect to characteristic molecular length of the plurality of labeled sample molecules, and further comprises dividing normalized label coverage depths by a median of normalized coverage depths for a plurality of sex chromosomes of a training set.

8. The method of claim 7, wherein normalized label coverage depths for an X chromosome are divided by the median normalized coverage depths for a plurality of female samples of a training set.

9. The method of claim 7, wherein normalized label coverage depths for a Y chromosome are divided by the median normalized coverage depths for a plurality of male samples of a training set and are further divided by two.

10. The method of claim 7, wherein the plurality of intervals of the reference are of equal size.

11. The method of claim 7, wherein the copy number profile is generated in less than five minutes after the signals are detected.

12. The method of claim 7, further comprising automatically determining a presence or absence of possible structural variation in of the genome or genomic fragment,
wherein automatically determining a presence or absence of possible regional structural variation comprises identifying possible breakpoints in the copy number profile, wherein an interval in the copy number profile with a significantly different copy number than a neighboring interval comprises a possible breakpoint.

13. The method of claim 12, wherein automatically determining a presence or absence of possible regional structural variation comprises determining GROM copy number breakpoints.

14. The method of claim 13, further comprising, for each of the copy number breakpoints:
identifying a first region of a reference sequence on a first side of the breakpoint, and masking a second region of the reference sequence on a second side of the breakpoint, wherein the second side is opposite the first side; and
scoring only single molecule alignments that align with the reference in the first region.

15. A method of characterizing a sample, the method comprising:
labeling a plurality of sample molecules with a first label, wherein the sample molecules comprise a genome or genomic fragment;
translocating the plurality of labeled sample molecules though a fluidic channel;
detecting counts of signals from the labeled sample molecules so as to ascertain a pattern or plurality of patterns characteristic of the genome or genomic fragment;
correlating signals from the labeled sample molecules to a reference to ascertain a coverage depth of signals of one or more regions of the genome or genomic fragment by the sample molecules;

scaling the coverage depths of signals to a subset of coverage depths of signals corresponding to regions of the genome or genomic fragment that does not comprise a sex chromosome or a fragment thereof, thereby providing scaled coverage depths; and normalizing the scaled coverage depths by one, two, or three of:
- characteristic molecular length of the plurality of labeled sample molecules; or
- characteristic number of labels per interval for a plurality of intervals of the reference, wherein the reference comprises a plurality of intervals; or
- characteristic number of labels per molecule or characteristic number of labels within a segment of predetermined length per molecule, thereby generating a copy number profile of the sample molecules in which bias due to label density and bias due to factors other than label density in the copy number profile are minimized or eliminated;

wherein normalizing the scaled coverage depths per interval comprises obtaining normalized label coverage depths as provided by the formula $n=(c-GL)/E$, wherein n represents normalized label coverage depths, c represents scaled coverage depth, L represents gradient of a linear regression of scaled coverage depth vs. the number of labels per interval for a plurality of samples in a training set, and G and E respectively represent gradient and zero-order coefficient of a linear regression of scaled coverage depth versus abscissa for a plurality of samples in a training set.

16. The method of claim 15, wherein the plurality of intervals of the reference are of equal size.

17. The method of claim 15, wherein the copy number profile is generated in less than five minutes after the signals are detected.

18. The method of claim 15, further comprising automatically determining a presence or absence of possible structural variation in of the genome or genomic fragment,
wherein automatically determining a presence or absence of possible regional structural variation comprises identifying possible breakpoints in the copy number profile, wherein an interval in the copy number profile with a significantly different copy number than a neighboring interval comprises a possible breakpoint.

19. The method of claim 18, wherein automatically determining a presence or absence of possible regional structural variation comprises determining GROM copy number breakpoints.

20. The method of claim 19, further comprising, for each of the copy number breakpoints:
identifying a first region of a reference sequence on a first side of the breakpoint, and masking a second region of the reference sequence on a second side of the breakpoint, wherein the second side is opposite the first side; and
scoring only single molecule alignments that align with the reference in the first region.

* * * * *